(12) United States Patent
Kikitsu et al.

(10) Patent No.: US 10,809,321 B2
(45) Date of Patent: Oct. 20, 2020

(54) MAGNETIC SENSOR AND TESTING DEVICE

(71) Applicant: KABUSHIKI KAISHA TOSHIBA, Tokyo (JP)

(72) Inventors: Akira Kikitsu, Kanagawa (JP); Satoshi Shirotori, Kanagawa (JP); Kenichiro Yamada, Tokyo (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 86 days.

(21) Appl. No.: 16/276,666

(22) Filed: Feb. 15, 2019

(65) Prior Publication Data
US 2019/0369172 A1 Dec. 5, 2019

(30) Foreign Application Priority Data

May 29, 2018 (JP) ................................ 2018-102781

(51) Int. Cl.
*G01R 33/09* (2006.01)
*A61B 5/04* (2006.01)

(52) U.S. Cl.
CPC ........ *G01R 33/093* (2013.01); *A61B 5/04008* (2013.01)

(58) Field of Classification Search
CPC .............. G01R 33/093; G01R 33/0023; G01R 33/0011; A61B 5/04008; A61B 2562/0223
(Continued)

(56) References Cited

U.S. PATENT DOCUMENTS 8,093,670 B2 * 1/2012 Taylor .................... G01R 33/07
257/427
2007/0063695 A1 * 3/2007 Ruhrig ................... G01R 33/09
324/207.21
(Continued)

FOREIGN PATENT DOCUMENTS

JP H11-83966 A 3/1999
JP 2017-3336 A 1/2017
(Continued)

OTHER PUBLICATIONS

Fujiwara et al., "Magnetocardiography and magnetoencephalography measurements at room temperature using tunnel magneto-resistance sensors." Applied Physics Express (Jan. 18, 2018), 11:023001-1 to 023001-4.
(Continued)

*Primary Examiner* — Giovanni Astacio-Oquendo
(74) *Attorney, Agent, or Firm* — Finnegan, Henderson, Farabow, Garrett & Dunner, L.L.P.

(57) ABSTRACT

According to one embodiment, a magnetic sensor includes first and second elements, first and second interconnects, a first circuit portion electrically connected to the first and second interconnects and a second circuit portion electrically connected to the first and second elements. The first circuit portion supplies a first alternating current to the first interconnect and supplies a second alternating current to the second interconnect. The second circuit portion supplies a first element current to the first element and supplies a second element current to the second element. At a first time, the first alternating current has a first alternating current orientation, and the second alternating current has a second alternating current orientation. At a second time, the first alternating current has an opposite orientation to the first alternating current orientation, and the second alternating
(Continued)

current has an opposite orientation to the second alternating current orientation.

20 Claims, 35 Drawing Sheets

(58) Field of Classification Search
USPC .................................... 324/252, 244, 200
See application file for complete search history.

(56) References Cited

U.S. PATENT DOCUMENTS

| 2018/0081001 A1 | 3/2018 | Iwasaki et al. |
| 2018/0252780 A1 | 9/2018 | Iwasaki et al. |
| 2018/0271395 A1* | 9/2018 | Iwasaki .................. G01N 27/72 |

FOREIGN PATENT DOCUMENTS

| JP | 2018-48832 A | 3/2018 |
| JP | 2018-146314 A | 9/2018 |
| JP | 2018-155719 A | 10/2018 |

OTHER PUBLICATIONS

Fujiwara et al., "Detection of Sub-Nano-Tesla Magnetic Field by Integrated Magnetic Tunnel Junctions with Bottom Synthetic Antiferro-Coupled Free Layer," Japanese Journal of Applied Physics (Apr. 22, 2013), 11:04CM07-1 to 04CM07-3.

Majima et al., "AC modulation method of a TMR magnetic sensor," The 40$^{th}$ Annual Meeting of The Magnetic Society of Japan (2016), p. 93.

Lamberton et al., "Current-in-Plane GMR Trilayer Head Design for Hard-Disk Drives: Characterization and Extendibility," IEEE Transactions on Magnetics (Feb. 2007), 43:645-650.

Seigler "Current in-Plane Giant Magnetoresistance Sensor Using a Thin Cu Spacer and Dual Nano-Oxide Layers With a DR Greater Than 20 Ohms/sq.," IEEE Transactions on Magnetics (Feb. 2007), 43:651-656.

* cited by examiner

MAGNETIC SENSOR AND TESTING DEVICE

CROSS-REFERENCE TO RELATED APPLICATIONS

This application is based upon and claims the benefit of priority from Japanese Patent Application No. 2018-102781, filed on May 29, 2018; the entire contents of which are incorporated herein by reference.

FIELD

Embodiments described herein relate generally to a magnetic sensor and a testing device.

BACKGROUND

There is a magnetic sensor using a magnetic layer. There is a testing device using the magnetic sensor. It is desirable to increase the detection sensitivity of the magnetic sensor.

DETAILED DESCRIPTION

Figure 1A:
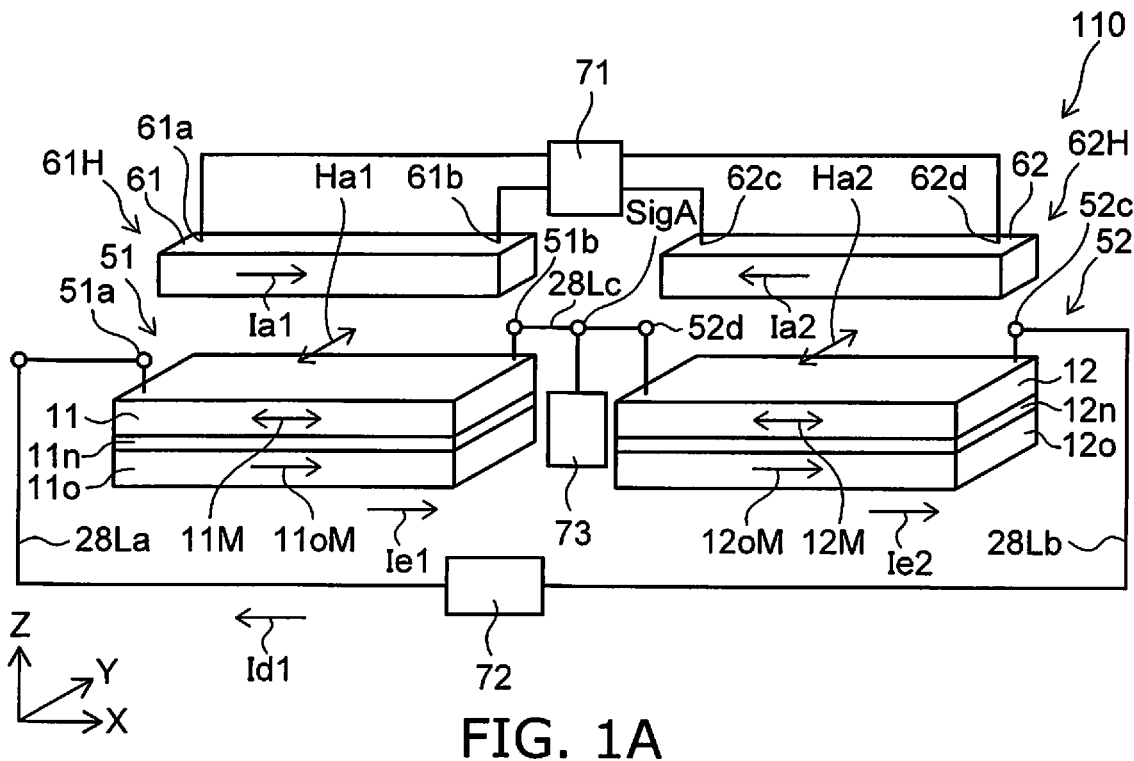
FIG. 1A to FIG. 1C are schematic perspective views illustrating a magnetic sensor according to a first embodiment.

According to one embodiment, a magnetic sensor includes a first element including a first magnetic layer, a second element including a second magnetic layer, a first interconnect, a second interconnect, a first circuit portion electrically connected to the first interconnect and the second interconnect, and a second circuit portion electrically connected to the first element and the second element. The first circuit portion is configured to supply a first alternating current to the first interconnect and to supply a second alternating current to the second interconnect. The second circuit portion is configured to supply a first element current to the first element and to supply a second element current to the second element. At a first time, the first alternating current has a first alternating current orientation, and the second alternating current has a second alternating current orientation. At a second time, the first alternating current has an opposite orientation to the first alternating current orientation, and the second alternating current has an opposite orientation to the second alternating current orientation. At the first time, the first element current has a first element current orientation, and the second element current has a second element current orientation. At the second time, the first element current has the first element current orientation, and the second element current has the second element current orientation. The first alternating current orientation has a component in an orientation of the first element current. The second alternating current orientation has a component in an opposite orientation to an orientation of the second element current.

According to one embodiment, a magnetic sensor includes a first element including a first magnetic layer, a second element including a second magnetic layer, a first interconnect, a second interconnect, a first circuit portion electrically connected to the first interconnect and the second interconnect, and a second circuit portion electrically connected to the first element and the second element. The first circuit portion is configured to supply a first alternating current to the first interconnect and to supply a second alternating current to the second interconnect. The second circuit portion is configured to supply a first element current to the first element and to supply a second element current to the second element. At least for some time, a phase of the first alternating current is opposite to a phase of the second alternating current with respect to an orientation of an external magnetic field applied to the first element and the second element.

According to one embodiment, a magnetic sensor includes a first element including a first magnetic layer, a second element including a second magnetic layer, a third element including a third magnetic layer, a fourth element including a fourth magnetic layer, first to fourth interconnects, a first circuit portion electrically connected to the first to fourth interconnects, and a second circuit portion electrically connected to the first to fourth elements. The first circuit portion is configured to supply first to fourth alternating currents respectively to the first to fourth interconnects. The second circuit portion is configured to supply first to fourth element currents respectively to the first to fourth elements. At a first time, the first to fourth alternating currents respectively have first to fourth alternating current orientations. At a second time, the first to fourth alternating currents respectively have opposite orientations to the first to fourth alternating current orientations. At the first time, the first to fourth element currents have first to fourth element current-alternating current orientations. At the second time, the first to fourth element currents have the first to fourth element current-alternating current orientations. The first alternating current orientation has a component in an orientation of the first element current. The second alternating current orientation has a component in an opposite orientation to an orientation of the second element current. The third alternating current orientation has a component in an orientation of the third element current. The fourth alternating current orientation has a component in an opposite orientation to an orientation of the fourth element current.

Various embodiments are described below with reference to the accompanying drawings.

The drawings are schematic and conceptual; and the relationships between the thickness and width of portions, the proportions of sizes among portions, etc., are not necessarily the same as the actual values. The dimensions and proportions may be illustrated differently among drawings, even for identical portions.

In the specification and drawings, components similar to those described previously or illustrated in an antecedent drawing are marked with like reference numerals, and a detailed description is omitted as appropriate.

First Embodiment

Figures 1B, 1C:
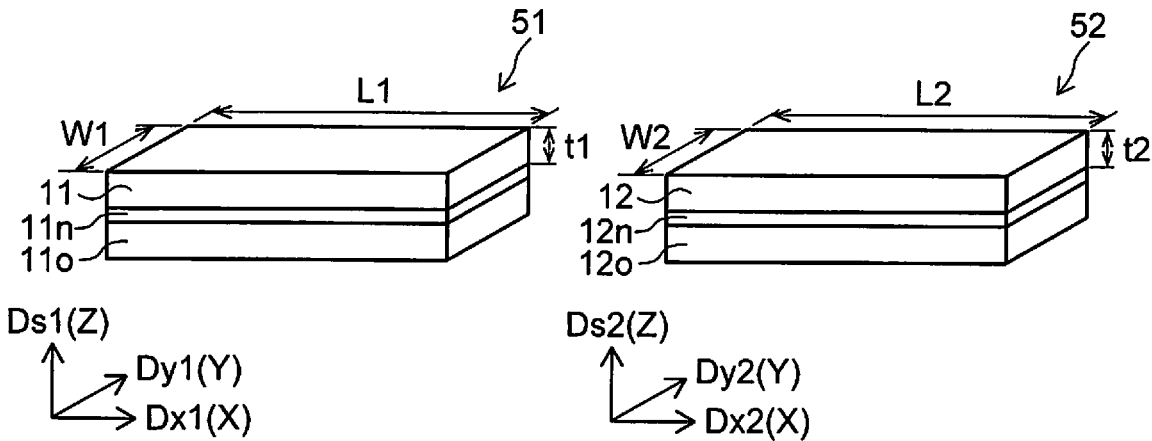

FIG. 1A to FIG. 1C are schematic perspective views illustrating a magnetic sensor according to a first embodiment.

FIG. 1B and FIG. 1C are perspective views illustrating portions of the magnetic sensor.

As shown in FIG. 1A, the magnetic sensor 110 according to the embodiment includes a first element 51, a second element 52, a first interconnect 61, a second interconnect 62, and a first circuit portion 71. In the example, the magnetic sensor 110 further includes a second circuit portion 72.

The first element 51 includes a first magnetic layer 11, a first opposing magnetic layer 11o, and a first nonmagnetic layer 11n. The first nonmagnetic layer 11n is provided between the first magnetic layer 11 and the first opposing magnetic layer 11o. The first magnetic layer 11 and the first opposing magnetic layer 11o are, for example, ferromagnetic. In one example, the first nonmagnetic layer 11n includes a nonmagnetic metal. The first element 51 is, for example, a current-in-plane GMR (Giant Magneto-Resistance) element.

As shown in FIG. 1B, a first stacking direction Ds1 from the first opposing magnetic layer 11o toward the first magnetic layer 11 is taken as a Z-axis direction. One direction perpendicular to the Z-axis direction is taken as an X-axis direction. A direction perpendicular to the Z-axis direction and the X-axis direction is taken as a Y-axis direction.

One direction crossing the first stacking direction Ds1 recited above is taken as a first magnetic layer direction Dx1. A direction crossing a plane including the first stacking direction Ds1 and the first magnetic layer direction Dx1 is taken as a first magnetic layer cross direction Dy1. For example, the first magnetic layer direction Dx1 is aligned with the X-axis direction. For example, the first magnetic layer cross direction Dy1 is aligned with the Y-axis direction.

In one example, a length L1 of the first magnetic layer 11 along the first magnetic layer direction Dx1 is longer than a length W1 of the first magnetic layer 11 along the first magnetic layer cross direction Dy1. The length W1 is, for example, the width of the first magnetic layer 11. The length L1 of the first magnetic layer 11 along the first magnetic layer direction Dx1 is longer than a length t1 of the first magnetic layer 11 along the first stacking direction Ds1. The length t1 is, for example, the thickness of the first magnetic layer 11. The length W1 is longer than the length t1. The first magnetic layer direction Dx1 is, for example, the major-axis direction of the first magnetic layer 11. The first magnetic layer cross direction Dy1 is, for example, the minor-axis direction of the first magnetic layer 11. The first stacking direction Ds1 is, for example, the thickness direction of the first magnetic layer 11.

The lengths along the first magnetic layer direction Dx1 of the first opposing magnetic layer 11o and the first nonmagnetic layer 11n may be substantially the same as the length L1. The lengths along the first magnetic layer cross direction Dy1 of the first opposing magnetic layer 11o and the first nonmagnetic layer 11n may be substantially the same as the length W1. The length along the first stacking direction Ds1 of the first opposing magnetic layer 11o may be substantially the same as the length t1.

The second element 52 includes a second magnetic layer 12, a second opposing magnetic layer 12o, and a second nonmagnetic layer 12n. The second nonmagnetic layer 12n is provided between the second magnetic layer 12 and the second opposing magnetic layer 12o. The second magnetic layer 12 and the second opposing magnetic layer 12o are, for example, ferromagnetic. In one example, the second nonmagnetic layer 12n includes a nonmagnetic metal. The second element 52 is, for example, a current-in-plane GMR element.

As shown in FIG. 1C, a second stacking direction Ds2 from the second opposing magnetic layer 12o toward the second magnetic layer 12 is aligned with the Z-axis direction. One direction crossing the second stacking direction Ds2 is taken as a second magnetic layer direction Dx2. A direction crossing a plane including the second stacking direction Ds2 and the second magnetic layer direction Dx2 is taken as a second magnetic layer cross direction Dy2. In the example, the second magnetic layer direction Dx2 is aligned with the X-axis direction. The second magnetic layer cross direction Dy2 is aligned with the Y-axis direction.

In one example, a length L2 of the second magnetic layer 12 along the second magnetic layer direction Dx2 is longer than a length W2 of the second magnetic layer 12 along the second magnetic layer cross direction Dy2. The length W2 is, for example, the width of the second magnetic layer 12. The length L2 of the second magnetic layer 12 along the second magnetic layer direction Dx2 is longer than a length t2 of the second magnetic layer 12 along the second stacking direction Ds2. The length t2 is, for example, the thickness of the second magnetic layer 12. The length W2 is longer than the length t2. The second magnetic layer direction Dx2 is, for example, the major-axis direction of the second magnetic layer 12. The second magnetic layer cross direction Dy2 is, for example, the minor-axis direction of the second magnetic layer 12. The second stacking direction Ds2 is, for example, the thickness direction.

The lengths along the second magnetic layer direction Dx2 of the second opposing magnetic layer 12o and the second nonmagnetic layer 12n may be substantially the same as the length L2. The lengths along the second magnetic layer cross direction Dy2 of the second opposing magnetic layer 12o and the second nonmagnetic layer 12n may be substantially the same as the length W2. The length along the second stacking direction Ds2 of the second opposing magnetic layer 12o may be substantially the same as the length t2.

The configuration (including the material) of the first magnetic layer 11 is applicable to the second magnetic layer 12. The configuration (including the material) of the first opposing magnetic layer 11o is applicable to the second opposing magnetic layer 12o. The configuration (including the material) of the first nonmagnetic layer 11n is applicable to the second nonmagnetic layer 12n.

The first element 51 includes a first element end portion 51a and a second element end portion 51b. The direction from the first element end portion 51a toward the second element end portion 51b is aligned with the first magnetic layer direction Dx1 (e.g., the X-axis direction). The first element end portion 51a and the second element end portion 51b correspond to two terminal portions of the first element 51.

The second element 52 includes a third element end portion 52c and a fourth element end portion 52d. The direction from the third element end portion 52c toward the fourth element end portion 52d is aligned with the second magnetic layer direction Dx2 (e.g., the X-axis direction). The third element end portion 52c and the fourth element end portion 52d correspond to two terminal portions of the second element 52.

The first magnetic layer 11 has a first magnetic layer magnetization 11M. The first opposing magnetic layer 11o has a first opposing magnetic layer magnetization 11oM. The second magnetic layer 12 has a second magnetic layer magnetization 12M. The second opposing magnetic layer 12o has a second opposing magnetic layer magnetization 12oM.

For example, any of the orientations of these magnetizations change according to a magnetic field applied to the magnetic layers from the outside. In one example, the orientation of the first magnetic layer magnetization 11M and the orientation of the second magnetic layer magnetization 12M change more easily than the orientation of the first opposing magnetic layer magnetization 11oM and the orientation of the second opposing magnetic layer magnetization 12oM. For example, the first magnetic layer 11 and the second magnetic layer 12 are free magnetic layers (e.g., detection layers). The first opposing magnetic layer 11o and the second opposing magnetic layer 12o are pinned magnetic layers (e.g., reference layers).

The electrical resistance of the first element 51 changes according to the angle between the first magnetic layer magnetization 11M and the first opposing magnetic layer magnetization 11oM. For example, the electrical resistance of the first element 51 corresponds to the electrical resistance between the first element end portion 51a and the second element end portion 51b. The electrical resistance of the second element 52 changes according to the angle between the second magnetic layer magnetization 12M and the second opposing magnetic layer magnetization 12oM. For example, the electrical resistance of the second element 52 corresponds to the electrical resistance between the third element end portion 52c and the fourth element end portion 52d.

In the example as shown in FIG. 1A, the second element end portion 51b and the fourth element end portion 52d are electrically connected to each other. For example, the connection is performed by an interconnect 28Lc.

In the example, the second circuit portion 72 is electrically connected to the first element end portion 51a and the third element end portion 52c. For example, the second circuit portion 72 and the first element end portion 51a are electrically connected by an interconnect 28La. For example, the second circuit portion 72 and the third element end portion 52c are electrically connected by an interconnect 28Lb. Any of these interconnects may be a ground.

Thus, in the example, the first element 51 and the second element 52 are electrically connected in series. The second circuit portion 72 supplies a first current Id1 to the first element 51 and the second element 52. The first current Id1 has at least a direct current component. The second circuit portion 72 is, for example, a constant voltage source.

The signal that is obtained when the first current Id1 flows through these elements includes information relating to the changes of the electrical resistances of these elements. For example, the electrical resistances of these elements change when a magnetic field is applied to these elements. For example, as described below, a signal SigA corresponding to the change of the potential of the connection point (the interconnect 28Lc) between the second element end portion 51b and the fourth element end portion 52d may be detected. The information that relates to the magnetic field applied to these elements is obtained using the signal SigA.

The first circuit portion 71 is electrically connected to the first interconnect 61 and the second interconnect 62. Alternating currents are supplied from the first circuit portion 71 to the first interconnect 61 and the second interconnect 62. Alternating-current (AC) magnetic fields are generated from these interconnects. The first interconnect 61 is one example of a first magnetic field generator 61H. The second interconnect 62 is one example of a second magnetic field generator 62H.

As shown in FIG. 1A, the distance between the first interconnect 61 and the first element 51 is shorter than the distance between the first interconnect 61 and the second element 52. The distance between the second interconnect 62 and the second element 52 is shorter than the distance between the second interconnect 62 and the first element 51.

The first interconnect 61 is a magnetic field generator for the first element 51. The second interconnect 62 is a magnetic field generator for the second element 52. For example, the direction from the first element 51 toward the first interconnect 61 is aligned with the first stacking direction Ds1 (e.g., the Z-axis direction). For example, the direction from the second element 52 toward the second interconnect 62 is aligned with the second stacking direction Ds2 (e.g., the Z-axis direction).

For example, the first interconnect 61 includes a first interconnect end portion 61a and a second interconnect end portion 61b. The second interconnect 62 includes a third interconnect end portion 62c and a fourth interconnect end portion 62d. These end portions are electrically connected to the first circuit portion 71. The electrical connections include electrical connections to ground.

As shown in FIG. 1A, the orientation from the third interconnect end portion 62c toward the fourth interconnect end portion 62d is aligned with the orientation from the first interconnect end portion 61a toward the second interconnect end portion 61b. For example, these orientations are aligned with the X-axis direction.

For example, the first circuit portion 71 supplies a first alternating current Ia1 to the first interconnect 61. A first AC magnetic field Ha1 is generated from the first interconnect 61. The first AC magnetic field Ha1 is applied to the first element 51. For example, the first alternating current Ia1 has a first frequency f1. For example, the first AC magnetic field Ha1 has the first frequency f1.

For example, the first circuit portion 71 supplies a second alternating current Ia2 to the second interconnect 62. A second AC magnetic field Ha2 is generated from the second interconnect 62. The second AC magnetic field Ha2 is applied to the second element 52. For example, the second alternating current Ia2 has the first frequency f1. For example, the second AC magnetic field Ha2 has the first frequency f1.

In addition to the magnetic field from a detection object, the first AC magnetic field Ha1 recited above is applied to the first element 51. In addition to the magnetic field from the detection object, the second AC magnetic field Ha2 recited above is applied to the second element 52. The phases of the first AC magnetic field Ha1 and the second AC magnetic field Ha2 are opposite to each other.

Thus, in the embodiment, the first circuit portion 71 supplies the first alternating current Ia1 to the first interconnect 61 and supplies the second alternating current Ia2 to the second interconnect 62. On the other hand, the second circuit portion 72 supplies a first element current Ie1 to the first element 51 and supplies a second element current Ie2 to the second element 52 (referring to FIG. 1A). At the first time, the first alternating current Ia1 has a first alternating current orientation (e.g., the orientation illustrated in FIG. 1A); and the second alternating current Ia2 has a second alternating current orientation (e.g., the orientation illustrated in FIG. 1A). The first time recited above is any one time and is, for example, a time corresponding to the state illustrated in FIG. 1A.

At the second time, the first alternating current Ia1 has the opposite orientation to the first alternating current orientation; and the second alternating current Ia2 has the opposite orientation to the second alternating current orientation. The second time is any time at which the polarities of the alternating currents are opposite to those at the first time.

In such a case, at the first time recited above, the first element current Ie1 has a first element current orientation (e.g., the orientation illustrated in FIG. 1A); and the second element current Ie2 has a second element current orientation (e.g., the orientation illustrated in FIG. 1A). At the second time as well, the first element current Ie1 has the first element current orientation recited above; and the second element current Ie2 has the second element current orientation recited above. In the embodiment, the first alternating current orientation recited above has a component in the orientation of the first element current Ie1. The second alternating current orientation recited above has a component in the opposite orientation to the orientation of the second element current Ie2.

Thus, in the embodiment, the first magnetic field generator 61H and the second magnetic field generator 62H that generate AC magnetic fields having phases opposite to each other are provided.

Examples of the first magnetic field generator 61H and the second magnetic field generator 62H, that supply the first alternating current Ia1 and the second alternating current Ia2 respectively to the first interconnect 61 and the second interconnect 62 will now be described.

FIG. 2A to FIG. 2F are schematic views illustrating an operation of the magnetic sensor according to the first embodiment.

In these figures, the horizontal axis is a time tm. The vertical axis of FIG. 2A corresponds to the first alternating current Ia1 supplied to the first interconnect 61. For the first alternating current Ia1, for example, the orientation from the first interconnect end portion 61a toward the second interconnect end portion 61b is defined as positive. The vertical axis of FIG. 2B corresponds to the second alternating current Ia2 supplied to the second interconnect 62. For the second alternating current Ia2, the orientation from the third interconnect end portion 62c toward the fourth interconnect end portion 62d is defined as positive.

Figure 2A:
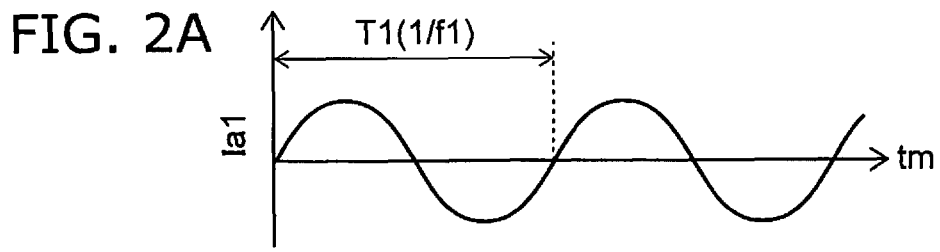
FIG. 2A to FIG. 2F are schematic views illustrating an operation of the magnetic sensor according to the first embodiment.
Figure 2B:
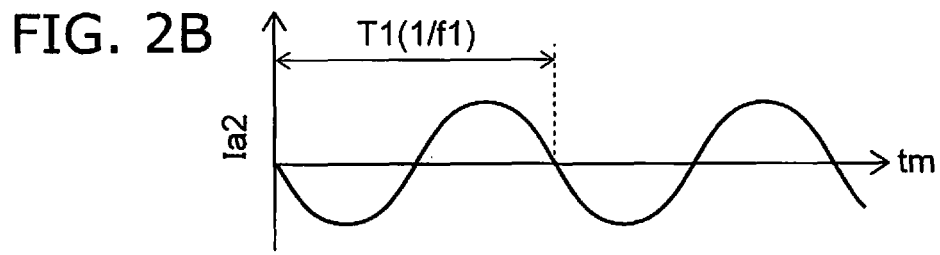
Figure 2C:
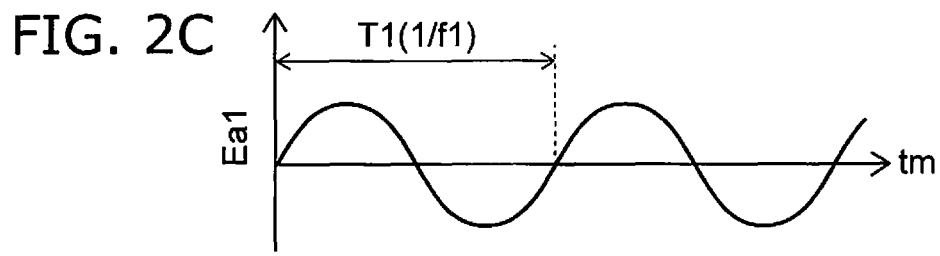

The vertical axis of FIG. 2C corresponds to a first electric potential Ea1 of the first interconnect end portion 61a of the first interconnect 61. In the example, the first potential Ea1 is defined as positive when the potential of the first interconnect end portion 61a is higher than the potential of the second interconnect end portion 61b. The vertical axis of FIG. 2D corresponds to a second electric potential Ea2 of the third interconnect end portion 62c of the second interconnect 62. In the example, the second potential Ea2 is defined as positive when the potential of the third interconnect end portion 62c is higher than the potential of the fourth interconnect end portion 62d.

Figure 2D:
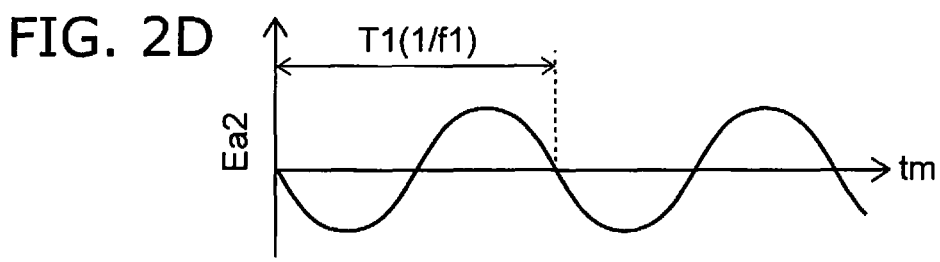
Figure 2E:
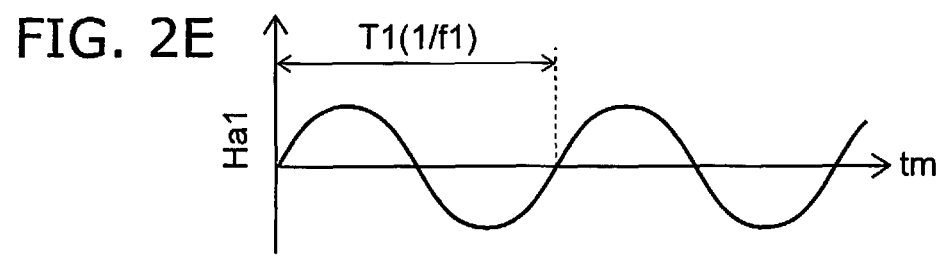

The vertical axis of FIG. 2E corresponds to the intensity of the first AC magnetic field Ha1 generated by the first interconnect 61. The vertical axis of FIG. 2F corresponds to the intensity of the second AC magnetic field Ha2 generated by the second interconnect 62.

Figure 2F:
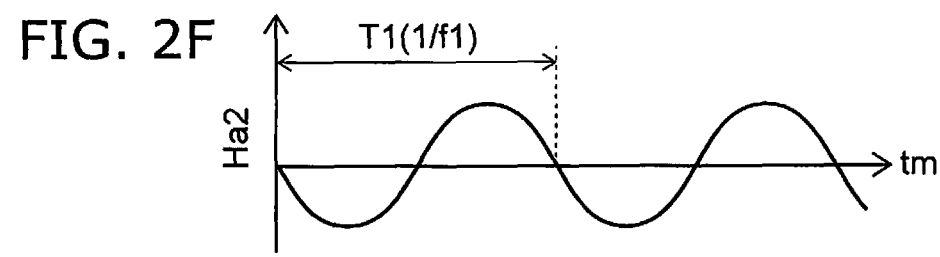

As shown in FIG. 2A and FIG. 2B, the first alternating current Ia1 and the second alternating current Ia2 change with a period T1. The first alternating current Ia1 and the second alternating current Ia2 have a first frequency f1. The period T1 is expressed by 1/f1. As shown in FIG. 2C and FIG. 2D, the first potential Ea1 and the second potential Eat change with the period T1. As shown in FIG. 2E and FIG. 2F, the first AC magnetic field Ha1 and the second AC magnetic field Ha2 change with the period T1. In the embodiment, for example, the first frequency f1 is higher than the frequency of the magnetic field from the detection object. The first frequency f1 is, for example, not less than 1 kHz and not more than 1 MHz. The first frequency f1 may be, for example, not less than 10 kHz and not more than 100 MHz.

In the embodiment as shown in these figures, the phases of the currents, the potentials, and the magnetic fields are opposite to each other between the two interconnects (the two AC magnetic field generators).

For example, the first alternating current Ia1 is positive at the first time (any one time tm). At this time, the first alternating current Ia1 has the orientation from the first interconnect end portion 61a toward the second interconnect end portion 61b (referring to FIG. 2A and FIG. 1A).

For example, the second alternating current Ia2 is negative at the first time recited above. At this time, the second alternating current Ia2 has the orientation from the fourth interconnect end portion 62d toward the third interconnect end portion 62c (referring to FIG. 2B and FIG. 1A).

Thus, at least at some time, the phase of the alternating current of the first interconnect 61 is opposite to the phase of the alternating current of the second interconnect 62.

For example, the first electric potential Ea1 is positive at the first time (any one time tm) (referring to FIG. 2C). At this time, the potential of the first interconnect end portion 61a is higher than the potential of the second interconnect end portion 61b. The second electric potential Ea2 is negative at the first time (referring to FIG. 2D). At this time, the potential of the fourth interconnect end portion 62d is higher than the potential of the third interconnect end portion 62c.

For example, the first AC magnetic field Ha1 is positive at the first time (any one time tm) (referring to FIG. 2E). The second AC magnetic field Ha2 is negative at the first time (referring to FIG. 2F). Thus, at least at some time, the phase of the first AC magnetic field Ha1 from to the first magnetic field generator 61H (e.g., the first interconnect 61) is opposite to the phase of the second AC magnetic field Ha2 from to the second magnetic field generator 62H (e.g., the second interconnect 62).

Such alternating currents are used in the embodiment. Thereby, as described below, unnecessary components are suppressed from the detecting signal. Thereby, the sensitivity of a magnetic sensor can be increased.

Figure 3:
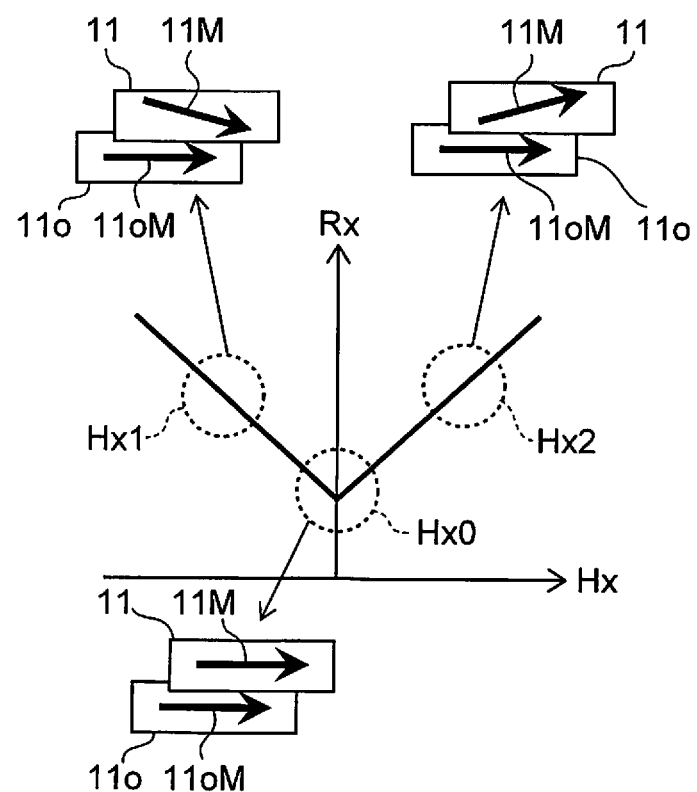
FIG. 3 is a graph illustrating a characteristic of the magnetic sensor.

FIG. 3 is a graph illustrating a characteristic of the magnetic sensor.

The horizontal axis of FIG. 3 corresponds to a magnetic field Hx applied to the element (e.g., the first element 51, the second element 52, or the like). The vertical axis corresponds to a resistance Rx of the element. For example, the magnetic field Hx from the outside has a component in a direction (e.g., the Y-axis direction) crossing the major-axis direction of the element. As shown in FIG. 3, the magnetic field Hx may be a magnetic field Hx0, a magnetic field Hx1, or a magnetic field Hx2. The absolute value of the magnetic field Hx0 is less than the absolute value of the magnetic field Hx1 and the absolute value of the magnetic field Hx2. The magnetic field Hx0 is, for example, 0. The magnetic field Hx1 is negative; and the magnetic field Hx2 is positive. The resistance Rx for the magnetic field Hx0 is smaller than the resistance Rx for the magnetic field Hx1 and smaller than the resistance Rx for the magnetic field Hx2. The resistance Rx is an even function with respect to the magnetic field Hx.

The first magnetic layer magnetization 11M of the first magnetic layer 11 and the first opposing magnetic layer magnetization 11oM of the first opposing magnetic layer 11o are shown schematically in FIG. 3. For example, the absolute value of the angle between the first magnetic layer magnetization 11M and the first opposing magnetic layer magnetization 11oM for the magnetic field Hx0 is less than the absolute value of the angle between the first magnetic layer magnetization 11M and the first opposing magnetic layer magnetization 11oM for the magnetic field Hx1 and less than the absolute value of the angle between the first magnetic layer magnetization 11M and the first opposing magnetic layer magnetization 11oM for the magnetic field Hx2. Changes of the orientations of the magnetizations such as those recited above are generated by applying the magnetic field Hx having a component in a direction crossing the major-axis direction of the element. Accordingly, changes of the resistance Rx such as those recited above occur.

An example of the characteristics of the element when an even-function characteristic such as that illustrated in FIG. 3 is utilized will now be described.

Figure 4:
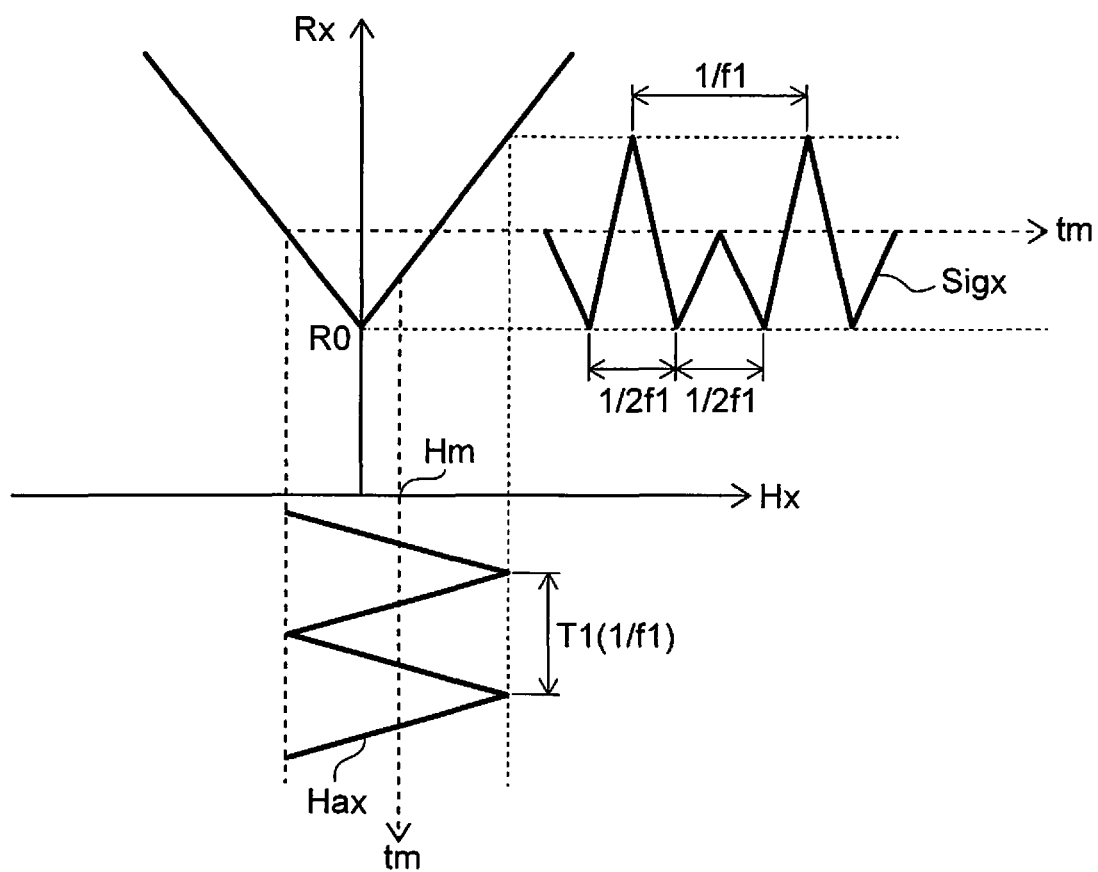
FIG. 4 is a graph illustrating the characteristics of the magnetic sensor.

FIG. 4 is a graph illustrating the characteristics of the magnetic sensor.

FIG. 4 illustrates the characteristics when an AC magnetic field Hax and a magnetic field Hm are applied as the magnetic field Hx to the element (e.g., the first element 51, the second element 52, or the like). The magnetic field Hm is the magnetic field from the measurement object (the detection object). The horizontal axis corresponds to the magnetic field Hx. The vertical axis corresponds to the resistance Rx of the element. In the example of FIG. 4, the AC magnetic field is a triangle wave. The AC magnetic field may be a sine wave, an alternating pulse wave, etc. The frequency of the AC magnetic field Hax is taken to be the first frequency f1.

As shown in FIG. 4, for example, a signal Sigx is obtained from the element when the AC magnetic field Hax and the magnetic field Hm are applied. The signal Sigx corresponds to the change of the resistance Rx. The signal Sigx has two components with different frequency with an offset corresponds to a resistance R0.

The signal Sigx (the resistance Rx) has a component of the first frequency f1 and a component of a doubled frequency 2f1. The signal component that corresponds to the first frequency f1 is caused by the magnetic field Hm. When the magnetic field Hm is 0, signal that corresponds to the first frequency f1 is substantially disappeared and the component of the double frequency 2f1 remains. For example, the component that corresponds to the first frequency f1 can be extracted using a filter, etc. The magnetic field Hm from the detection object can be known by measuring the intensity of the signal corresponding to the first frequency f1. The signal that has the double frequency 2f1 is, for example, an unnecessary signal (e.g., noise).

The magnetic field Hm may be a direct-current (DC) magnetic field or an AC magnetic field. In the case where the magnetic field Hm is an AC magnetic field, the frequency of the magnetic field Hm is lower than the frequency of the AC magnetic field Hax (the first frequency f1).

FIG. 4 illustrates the case where one AC magnetic field Hax is applied to one element. In the embodiment, the first AC magnetic field Ha1 is applied to the first element 51 from the first magnetic field generator 61H (e.g., the first interconnect 61); and the second AC magnetic field Ha2 is applied to the second element 52 from the second magnetic field generator 62H (e.g., the second interconnect 62).

Figure 5:
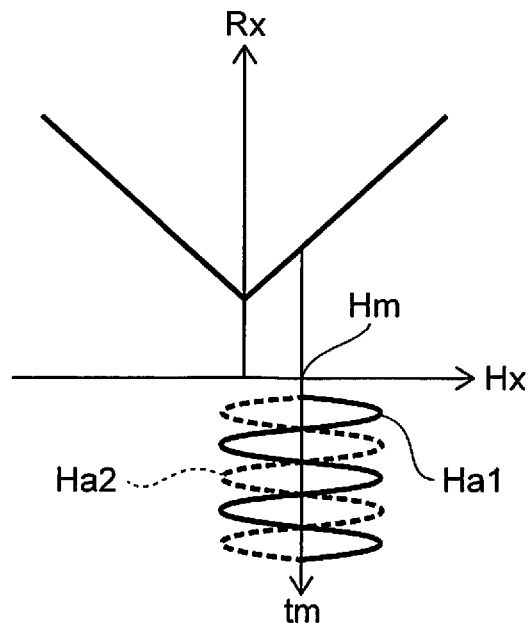
FIG. 5 is a graph illustrating a characteristic of the magnetic sensor.

FIG. 5 is a graph illustrating a characteristic of the magnetic sensor.

The horizontal axis of FIG. 5 corresponds to the magnetic field Hx. The vertical axis of FIG. 5 corresponds to the resistance Rx. As illustrated in FIG. 5, the phase of the first AC magnetic field Ha1 is opposite to the phase of the second AC magnetic field Ha2. Two types of signals Sigx corresponding respectively to the first AC magnetic field Ha1 and the second AC magnetic field Ha2 are generated (referring to FIG. 4). The phases are shifted by a period of ½f1 between the two types of signals Sigx. Therefore, for example, when the two types of signals Sigx are subtracted, the components that have the double frequency 2f1 is substantially removed. A signal that corresponds to the first frequency f1 remains. The magnetic field Hm of the detection object can be known by measuring the intensity of the signal (e.g., the peak) corresponding to the first frequency f1. By using such AC magnetic fields having opposite phases, the component of the double frequency 2f1 (e.g., the unnecessary signal) can be suppressed. According to the embodiment, a magnetic sensor can be provided in which the detection sensitivity can be increased.

For example, the signal SigA that corresponds to the change of the electric potential of the connection point between the second element end portion 51b and the fourth element end portion 52d illustrated in FIG. 1A is detected. Information on the magnetic field Hm which comes from the detection object is obtained by measuring the signal intensity of the signal SigA corresponding to the first frequency f1. For example, the signal intensity of the signal SigA corresponding to the double frequency 2f1 is smaller than the signal intensity of the signal SigA corresponding to the first frequency f1. For example, the component of the signal SigA corresponding to the double frequency 2f1 is substantially not generated.

In the embodiment, a component that corresponds to the double frequency 2f1 may remained by deviation of the magnetic characteristics in the multiple elements (the first element 51 and the second element 52), or due to the electric characteristics of the interconnects electrically connected to these elements, etc. Even in such a case, the unnecessary signal corresponding to the double frequency 2f1 can be suppressed markedly. The detection sensitivity can be increased. For example, amplification is easy. For example, an amplifier that has a high amplification factor can be used since the unnecessary component is markedly reduced.

For example, as shown in FIG. 1A, a third circuit portion 73 may be further provided. For example, the third circuit portion 73 is electrically connected to the connection point (the interconnect 28Lc) between the second element end portion 51b and the fourth element end portion 52d. For example, the third circuit portion 73 outputs the signal SigA corresponding to the change of the electric potential of the second element end portion 51b and the fourth element end portion 52d. In the embodiment, for example, the signal SigA is detected.

For example, the first alternating current Ia1 and the second alternating current Ia2 have the first frequency f1. The signal SigA recited above corresponds to the component of the first frequency f1 recited above of the change of the electric potential of the second element end portion 51b and the fourth element end portion 52d. By detecting the signal SigA, the information that corresponds to the magnetic field Hm from the detection object is obtained.

Figure 6:
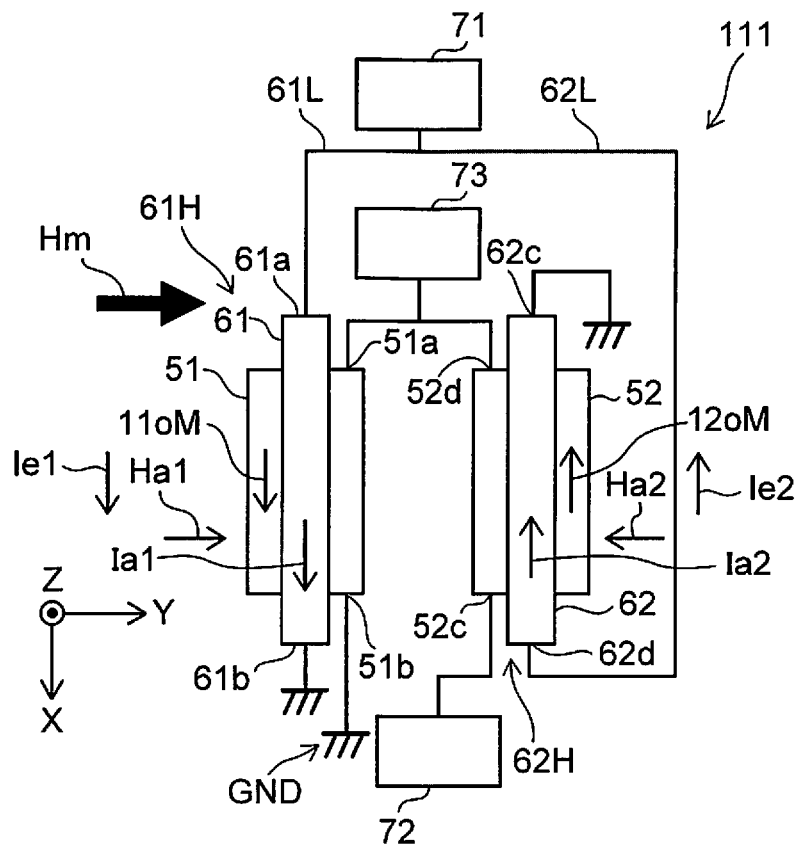
FIG. 6 is a schematic view illustrating a magnetic sensor according to the first embodiment.

FIG. 6 is a schematic view illustrating a magnetic sensor according to the first embodiment.

As shown in FIG. 6, the magnetic sensor 111 according to the embodiment also includes the first element 51, the second element 52, the first interconnect 61, the second interconnect 62, and the first circuit portion 71. In the example, the magnetic sensor 111 further includes the second circuit portion 72 and the third circuit portion 73.

In the example, the first element 51 includes the first element end portion 51a and the second element end portion 51b. The second element 52 includes the third element end portion 52c and the fourth element end portion 52d. In the example, the second circuit portion 72 is electrically connected to the third element end portion 52c. The first element end portion 51a and the fourth element end portion 52d are electrically connected. For example, the second element end portion 51b is electrically connected to a ground GND. The third circuit portion 73 is electrically connected to the connection point between the first element end portion 51a and the fourth element end portion 52d.

As shown in FIG. 6, the first interconnect 61 includes the first interconnect end portion 61a and the second interconnect end portion 61b. The second interconnect 62 includes the third interconnect end portion 62c and the fourth interconnect end portion 62d. The orientation from the third interconnect end portion 62c toward the fourth interconnect end portion 62d is aligned with the orientation from the first interconnect end portion 61a toward the second interconnect end portion 61b.

The first circuit portion 71 is electrically connected to the first interconnect end portion 61a by an interconnect 61L. The first circuit portion 71 is electrically connected to the fourth interconnect end portion 62d by an interconnect 62L. On the other hand, the second interconnect end portion 61b and the third interconnect end portion 62c are electrically connected to ground (e.g., the ground conductive portion GND).

One alternating current from the first circuit portion 71 is supplied to the first interconnect 61 and the second interconnect 62. This alternating current is the first alternating current Ia1 in the first interconnect 61. This alternating current is the second alternating current Ia2 in the second interconnect 62. In such a case, the second alternating current Ia2 has the orientation from the fourth interconnect end portion 62d toward the third interconnect end portion 62c at the time when the first alternating current Ia1 has the orientation from the first interconnect end portion 61a toward the second interconnect end portion 61b. The second alternating current Ia2 has the orientation from the third interconnect end portion 62c toward the fourth interconnect end portion 62d at the time when the first alternating current Ia1 has the orientation from the second interconnect end portion 61b toward the first interconnect end portion 61a.

Thus, the phases of the supplied alternating currents are opposite between the first interconnect 61 and the second interconnect 62.

Thus, in the magnetic sensor 111, at least at some time, the phase of the first alternating current Ia1 is opposite to the phase of the second alternating current Ia2 with respect to the orientation of the external magnetic field (which may be, for example, the magnetic field Hm) applied to the first element 51 and the second element 52.

The magnetic field Hm from the detection object and the first AC magnetic field Ha1 generated from the first magnetic field generator 61H (e.g., the first interconnect 61) are applied to the first element 51. The magnetic field Hm from the detection object and the second AC magnetic field Ha2 generated from the second magnetic field generator 62H (e.g., the second interconnect 62) are applied to the second element 52.

Figure 7A:
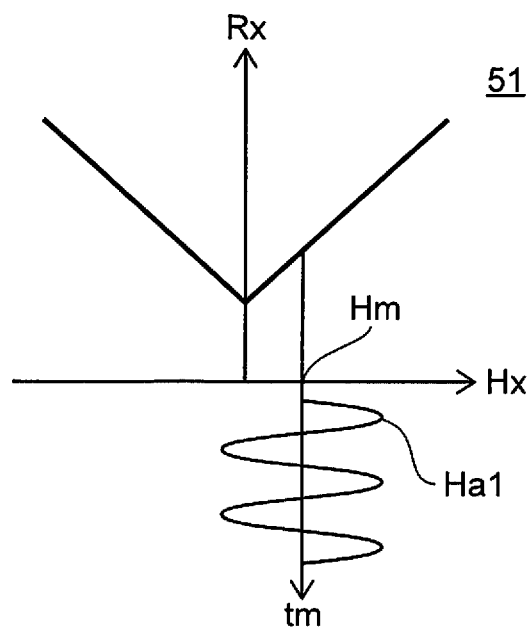
FIG. 7A and FIG. 7B are graphs illustrating characteristics of the magnetic sensor according to the first embodiment.
Figure 7B:
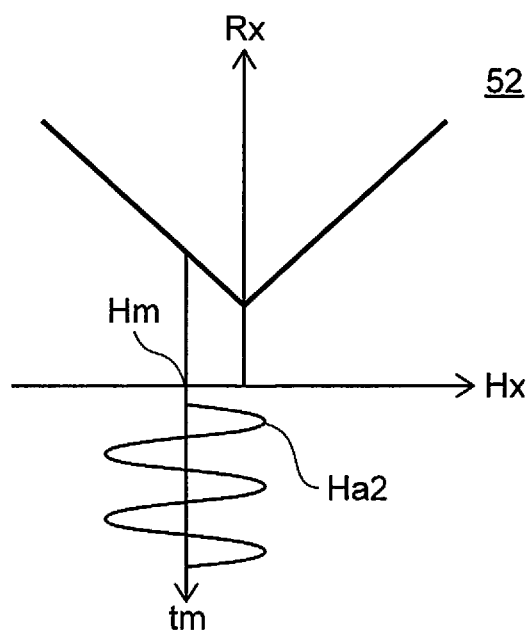

FIG. 7A and FIG. 7B are graphs illustrating characteristics of the magnetic sensor according to the first embodiment.

These figures illustrate the characteristics of the magnetic sensor 111 illustrated in FIG. 6. In FIG. 7A and FIG. 7B, the horizontal axis corresponds to the magnetic field Hx. The vertical axis corresponds to the resistance Rx. FIG. 7A corresponds to the first element 51 of the magnetic sensor 111. FIG. 7B corresponds to the second element 52 of the magnetic sensor 111.

As shown in FIG. 7A, the magnetic field Hm from the detection object and the first AC magnetic field Ha1 are applied to the first element 51. As shown in FIG. 7B, the magnetic field Hm from the detection object and the second AC magnetic field Ha2 are applied to the second element 52. As shown in FIG. 6, the first element 51 and the second element 52 have opposite orientations to each other with respect to the magnetic field Hm from the outside. Accordingly, as in FIG. 7A and FIG. 7B, in the case where the characteristics of the first element 51 and the second element 52 are shown so that the orientations are the same, the characteristics are such that the polarities of the magnetic field Hm are reversed (positive and negative).

Such a first AC magnetic field Ha1 and such a second AC magnetic field Ha2 are applied respectively to the first element 51 and the second element 52. Therefore, the phase of the change of the resistance Rx of the first element 51 is opposite to the phase of the change of the resistance Rx of the second element 52. Therefore, as described above, the intensity of the component corresponding to the double frequency 2f1 is smaller than the intensity of the component corresponding to the first frequency f1 for the signal of the connection point between the first element 51 and the second element 52 which are connected to each other. Thereby, the detection sensitivity can be increased.

Figure 8A:
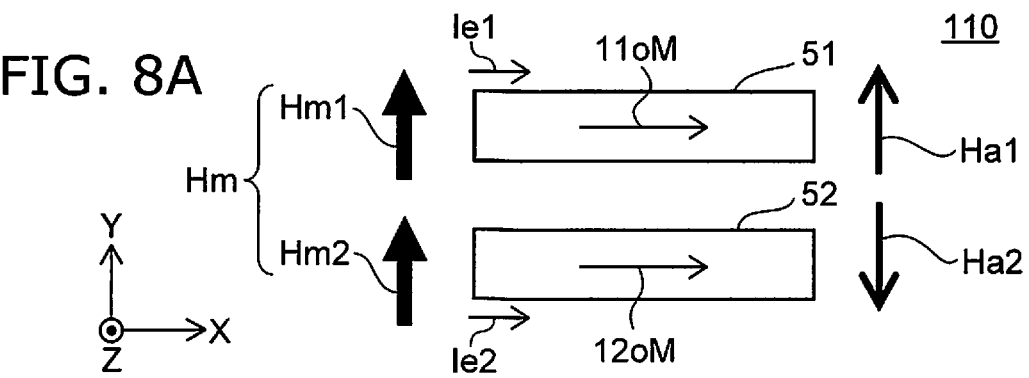
FIG. 8A and FIG. 8B are schematic views illustrating portions of the magnetic sensors according to the first embodiment.
Figure 8B:
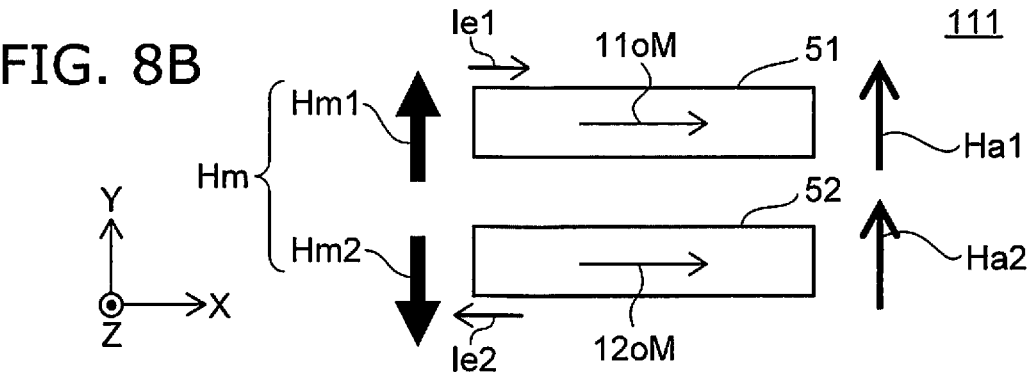

FIG. 8A and FIG. 8B are schematic views illustrating portions of the magnetic sensors according to the first embodiment.

FIG. 8A and FIG. 8B illustrate the orientations of the magnetic field Hm, the first opposing magnetic layer magnetization 11oM, the second opposing magnetic layer magnetization 12oM, the first AC magnetic field Ha1, and the second AC magnetic field Ha2. In the example shown in FIG. 8A, a magnetic field Hm1 (a component of the magnetic field Hm from the detection object) is applied to the first element 51; and a magnetic field Hm2 (a component of the magnetic field Hm from the detection object) is applied to the second element 52. The orientation of the magnetic field Hm1 and the orientation of the magnetic field Hm2 are the same. In such a case, a component of the first AC magnetic field Ha1 that is applied to the first element 51 and a component of the second AC magnetic field Ha2 that is applied to the second element 52 have a phase opposite to each other at some time.

In the example shown in FIG. 8B, the magnetic field Hm1 (a component of the magnetic field Hm from the detection object) that is applied to the first element 51 has opposite orientation to the orientation of the magnetic field Hm2 (a component of the magnetic field Hm from the detection object) that is applied to the second element 52. In such a case, the first AC magnetic field Ha1 that is applied to the first element 51 and the second AC magnetic field Ha2 that is applied to the second element 52 have the same phase (have a component in the same orientation) at some time. In this case, the phase of the first AC magnetic field Ha1 has opposite phase to the phase of the second AC magnetic field Ha2 when referenced to the magnetic field Hm. The configuration of FIG. 8B corresponds to the example shown in FIG. 6, FIG. 7A, and FIG. 7B.

The configuration illustrated in FIG. 8A and the configuration illustrated in FIG. 8B are defined by the configurations of the multiple elements, the multiple interconnects (the magnetic field generators), and the interconnects that connect the multiple elements and the multiple interconnects.

In the examples according to the embodiment as described above, elements that have even-function characteristics are used. For example, the electrical resistance of the first element 51 has an even-function characteristic with respect to the magnetic field applied to the first element 51. The electrical resistance of the second element 52 has an even-function characteristic with respect to the magnetic field applied to the second element 52. In the embodiment, the component of the double frequency 2f1 can be suppressed. Thereby, for example, a high SNR can be obtained.

In one example according to the embodiment, the length L1 of the first magnetic layer 11 along the first magnetic layer direction Dx1 (referring to FIG. 1B) is not less than 10 times the length W1 of the first magnetic layer 11 along the first magnetic layer cross direction Dy1 (referring to FIG. 1B). The length L2 of the second magnetic layer 12 along the second magnetic layer direction Dx2 (referring to FIG. 1C) is not less than 10 times the length W2 of the second magnetic layer 12 along the second magnetic layer cross direction Dy2 (referring to FIG. 1C).

In one example, the length t1 of the first magnetic layer 11 along the first stacking direction Ds1 (referring to FIG. 1B) is not more than ½ times the length W1 of the first magnetic layer 11 along the first magnetic layer cross direction Dy1 (referring to FIG. 1B). The length t2 of the second magnetic layer 12 along the second stacking direction Ds2 (referring to FIG. 1C) is not more than ½ times the length W2 of the second magnetic layer 12 along the second magnetic layer cross direction Dy2 (referring to FIG. 1C).

For example, the first magnetic layer magnetization 11M of the first magnetic layer 11 is aligned with the first magnetic layer direction Dx1 when an external magnetic field is substantially not applied to the first element 51. The second magnetic layer magnetization 12M of the second magnetic layer 12 is aligned with the second magnetic layer direction Dx2 when an external magnetic field is substantially not applied to the second element 52. The first opposing magnetic layer magnetization 11oM of the first opposing magnetic layer 11o is aligned with the first magnetic layer direction Dx1 when an external magnetic field is substantially not applied to the first element 51. The second opposing magnetic layer magnetization 12oM of the second opposing magnetic layer 12o is aligned with the second magnetic layer direction Dx2 when an external magnetic field is substantially not applied to the second element 52.

Figure 9:
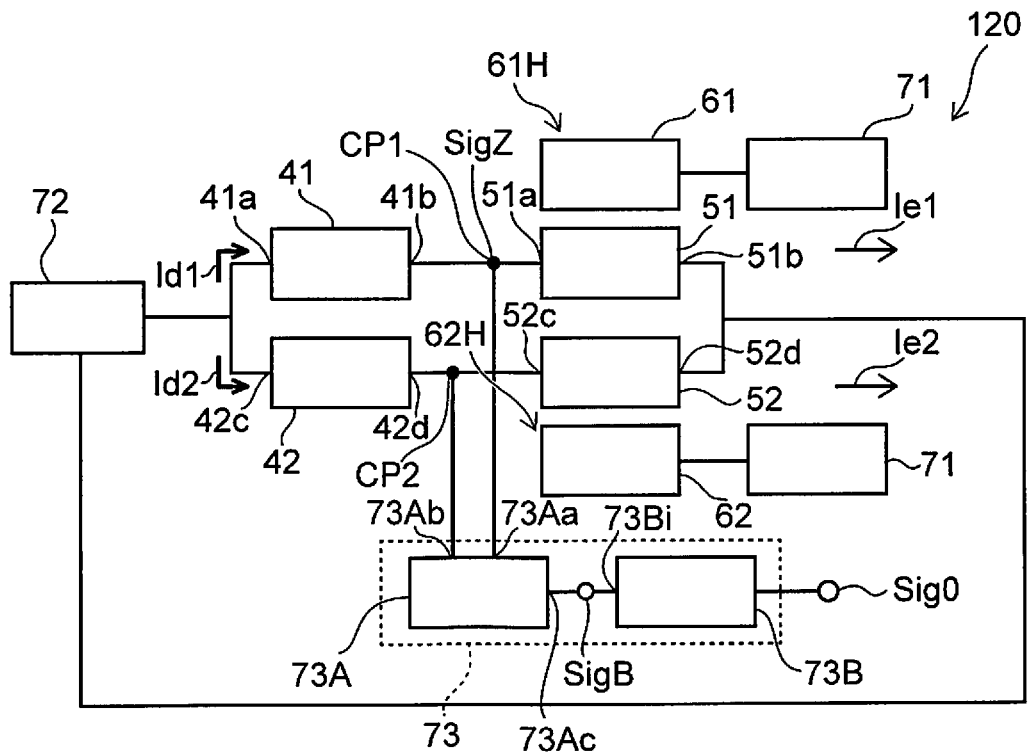
FIG. 9 is a schematic view illustrating a magnetic sensor according to the first embodiment.

FIG. 9 is a schematic view illustrating a magnetic sensor according to the first embodiment.

As shown in FIG. 9, the magnetic sensor 120 according to the embodiment further includes a first resistor 41 and a second resistor 42 in addition to the first element 51, the second element 52, the first interconnect 61, the second interconnect 62, and the first circuit portion 71. In the example, the magnetic sensor 120 further includes the second circuit portion 72 and the third circuit portion 73.

The configurations of the first element 51 and the second element 52 of the magnetic sensor 120 are similar to the configurations of the first element 51 and the second element 52 of the magnetic sensor 110. For example, the first element 51 includes the first magnetic layer 11, the first opposing magnetic layer 11o, and the first nonmagnetic layer 11n provided between the first magnetic layer 11 and the first opposing magnetic layer 11o (referring to FIG. 1B). For example, the second element 52 includes the second magnetic layer 12, the second opposing magnetic layer 12o, and the second nonmagnetic layer 12n provided between the second magnetic layer 12 and the second opposing magnetic layer 12o (referring to FIG. 1C).

As shown in FIG. 9, the first element 51 includes the first element end portion 51a and the second element end portion 51b. The second element 52 includes the third element end portion 52c and the fourth element end portion 52d. In the example, the second element end portion 51b and the fourth element end portion 52d are electrically connected to each other.

The first resistor 41 includes a first resistor end portion 41a and a second resistor end portion 41b. The second resistor 42 includes a third resistor end portion 42c and a fourth resistor end portion 42d. The second resistor end portion 41b and the first element end portion 51a are electrically connected to each other. The fourth resistor end portion 42d and the third element end portion 52c are electrically connected to each other.

The second circuit portion 72 is electrically connected to the first resistor end portion 41a, the third resistor end portion 42c, the second element end portion 51b, and the fourth element end portion 52d. As described below, the second circuit portion 72 may be electrically connected to the first resistor end portion 41a and the third resistor end portion 42c via the ground conductive portion GND. The second circuit portion 72 may be electrically connected to the second element end portion 51b and the fourth element end portion 52d via the ground GND.

The second circuit portion 72 supplies the first current Id1 to a set of the first resistor 41 and the first element 51. The first current Id1 has at least a direct current component. The second circuit portion 72 supplies a second current Id2 to a set of the second resistor 42 and the second element 52. The second current Id2 has at least a direct current component. The magnitude of the first current Id1 may be substantially the same as the magnitude of the second current Id2. For example, the first current Id1 has the orientation from the first resistor 41 toward the first element 51. For example, the second current Id2 has the orientation from the second resistor 42 toward the second element 52. The second circuit portion 72 is, for example, a constant voltage source.

In the magnetic sensor 120 as well, the first circuit portion 71 is connected to the first interconnect 61 (the first magnetic field generator 61H) and the second interconnect 62 (the second magnetic field generator 62H). In the example as well, the distance between the first interconnect 61 and the first element 51 is shorter than the distance between the first interconnect 61 and the second element 52. The distance between the second interconnect 62 and the second element 52 is shorter than the distance between the second interconnect 62 and the first element 51.

In such a case as well, AC magnetic fields are generated from the first magnetic field generator 61H (e.g., the first interconnect 61) and the second magnetic field generator 62H (e.g., the second interconnect 62) by the first circuit portion 71. The phase of the AC magnetic field from the first magnetic field generator 61H is opposite to the phase of the AC magnetic field from the second magnetic field generator 62H.

For example, configurations of the multiple interconnects in the magnetic sensor 120 may be similar to those in the magnetic sensor 110. For example, the first interconnect 61 includes the first interconnect end portion 61a and the second interconnect end portion 61b (referring to FIG. 1A). The second interconnect 62 includes the third interconnect end portion 62c and the fourth interconnect end portion 62d (referring to FIG. 1A). For example, the orientation from the third interconnect end portion 62c toward the fourth interconnect end portion 62d is aligned with the orientation from the first interconnect end portion 61a toward the second interconnect end portion 61b (referring to FIG. 1A).

The first circuit portion 71 supplies the first alternating current Ia1 to the first interconnect 61 (referring to FIG. 1A). The first alternating current Ia1 has the orientation from the first interconnect end portion 61a toward the second interconnect end portion 61b at the first time (any one time tm) (referring to FIG. 1A). The first circuit portion 71 supplies the second alternating current Ia2 to the second interconnect 62 (referring to FIG. 1A). The second alternating current Ia2 has the orientation from the fourth interconnect end portion 62d toward the third interconnect end portion 62c at the first time recited above.

In the magnetic sensor 120 as well, for example, the component of the double frequency 2f1 is suppressed. The detection sensitivity can be increased.

As shown in FIG. 9, for example, a bridge is formed of the first resistor 41, the second resistor 42, the first element 51, and the second element 52. For example, the connection point between the second resistor end portion 41b of the first resistor 41 and the first element end portion 51a of the first element 51 is a first connection point CP1. For example, the connection point between the fourth resistor end portion 42d of the second resistor 42 and the third element end portion 52c of the second element 52 is a second connection point CP2. For example, the electric potential difference between the first connection point CP1 and the second connection point CP2 may be detected. For example, the component of the double frequency 2f1 can be suppressed; further, the DC electric potential by the resistance component R0 in FIG. 4 can be suppressed. For example, the component of the first frequency f1 can be detected more easily. The detection sensitivity can be increased further.

As shown in FIG. 9, the magnetic sensor 120 may further include the third circuit portion 73. The third circuit portion 73 is electrically connected to the first connection point CP1 and the second connection point CP2. For example, the third circuit portion 73 can output a signal Sig0 corresponding to the change of the electric potential difference between the first element end portion 51a and the third element end portion 52c (referring to FIG. 9). For example, the third circuit portion 73 has a differential amplification function.

As described above, the first alternating current Ia1 and the second alternating current Ia2 have the first frequency f1. In such a case, the signal Sig0 recited above has a component of the first frequency f1 of the potential difference recited above between the first element end portion 51a and the third element end portion 52c.

In one example, the third circuit portion 73 includes a differential circuit portion 73A and a filter 73B. The differential circuit portion 73A includes a first input terminal 73Aa, a second input terminal 73Ab, and a differential circuit portion output terminal 73Ac. The first input terminal 73Aa is electrically connected to the first element end portion 51a (e.g., the first connection point CP1). The second input terminal 73Ab is electrically connected to the third element end portion 52c (e.g., the second connection point CP2). The differential circuit portion output terminal 73Ac outputs a signal SigB corresponding to the electric potential difference between the first input terminal 73Aa and the second input terminal 73Ab.

An input terminal 73Bi of the filter 73B is electrically connected to the differential circuit portion output terminal 73Ac. The filter 73B outputs the signal Sig0, that corresponding to a portion of a frequency of the signal SigB from the differential circuit portion output terminal 73Ac (e.g., the component of the first frequency f1).

Figure 10A:
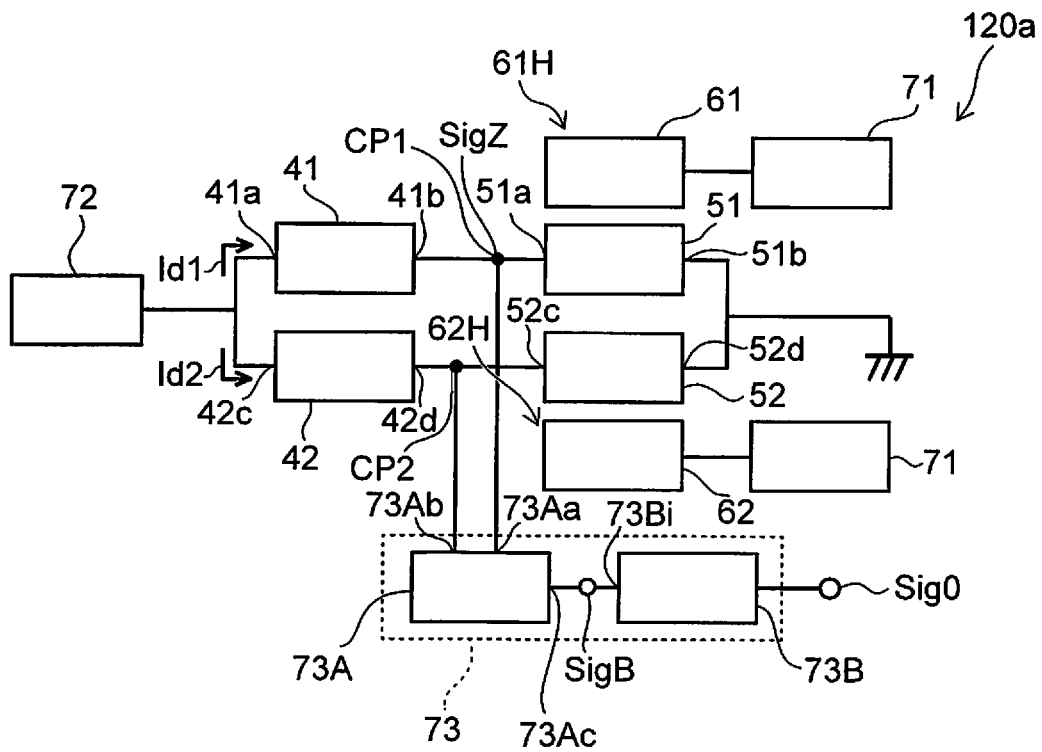
FIG. 10A and FIG. 10B are schematic views illustrating magnetic sensors according to the first embodiment.
Figure 10B:
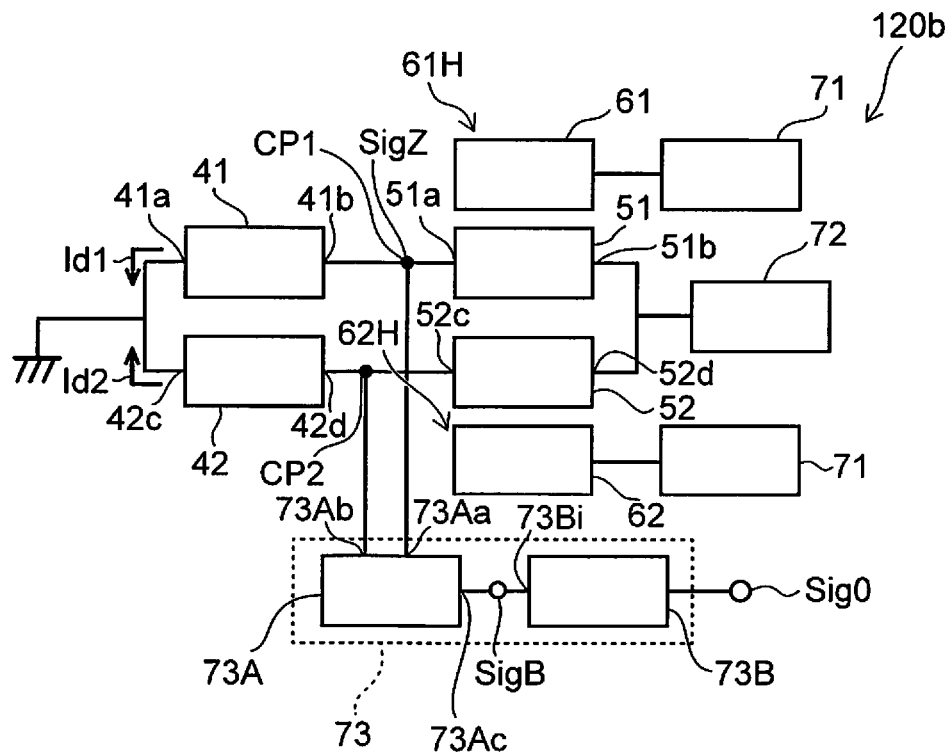

FIG. 10A and FIG. 10B are schematic views illustrating magnetic sensors according to the first embodiment.

In a magnetic sensor 120a according to the embodiment as shown in FIG. 10A, the second circuit portion 72 is electrically connected to the first resistor end portion 41a and the third resistor end portion 42c. The second element end portion 51b and the fourth element end portion 52d are electrically connected to the ground GND. The second circuit portion 72 is electrically connected to the second element end portion 51b and the fourth element end portion 52d via the ground GND.

In a magnetic sensor 120b according to the embodiment as shown in FIG. 10B, the second circuit portion 72 is electrically connected to the second element end portion 51b and the fourth element end portion 52d. The first resistor end portion 41a and the third resistor end portion 42c are electrically connected to the ground GND. The second circuit portion 72 is electrically connected to the first resistor end portion 41a and the third resistor end portion 42c via the ground GND.

For the magnetic sensor 120a and the magnetic sensor 120b as well, operations similar to those described in reference to the magnetic sensor 120 may be performed. In the magnetic sensor 120a and the magnetic sensor 120b as well, the component of the double frequency 2f1 is suppressed. The detection sensitivity can be increased.

An example of the characteristics of the magnetic sensor will now be described.

The sample element (corresponding to the first element 51 or the second element 52) has the following configuration. Hereinbelow, the values inside the parentheses are the thicknesses. The pinned magnetic layer includes an IrMn film (7 nm)/CoFe film (2 nm)/Ru film (0.9 nm)/CoFe film (2 nm). The nonmagnetic layer includes a Cu film (3.4 nm). The detection layer includes a CoFe film (3 nm). In the example, the element further includes a Cu film (3.4 nm)/CoFe film (2 nm)/Ru film (0.9 nm)/CoFe film (2 nm)/IrMn film (7 nm). The element of the experiment sample further includes a Ta under layer, a Ta protective layer, another under layer, and another protective layer. The element is obtained by patterning the stacked film having the structure recited above. Cu interconnects are connected to two end portions of the element. The electrical resistance of the element is measured under the external magnetic field applied to the element obtained as recited above.

Figure 11:
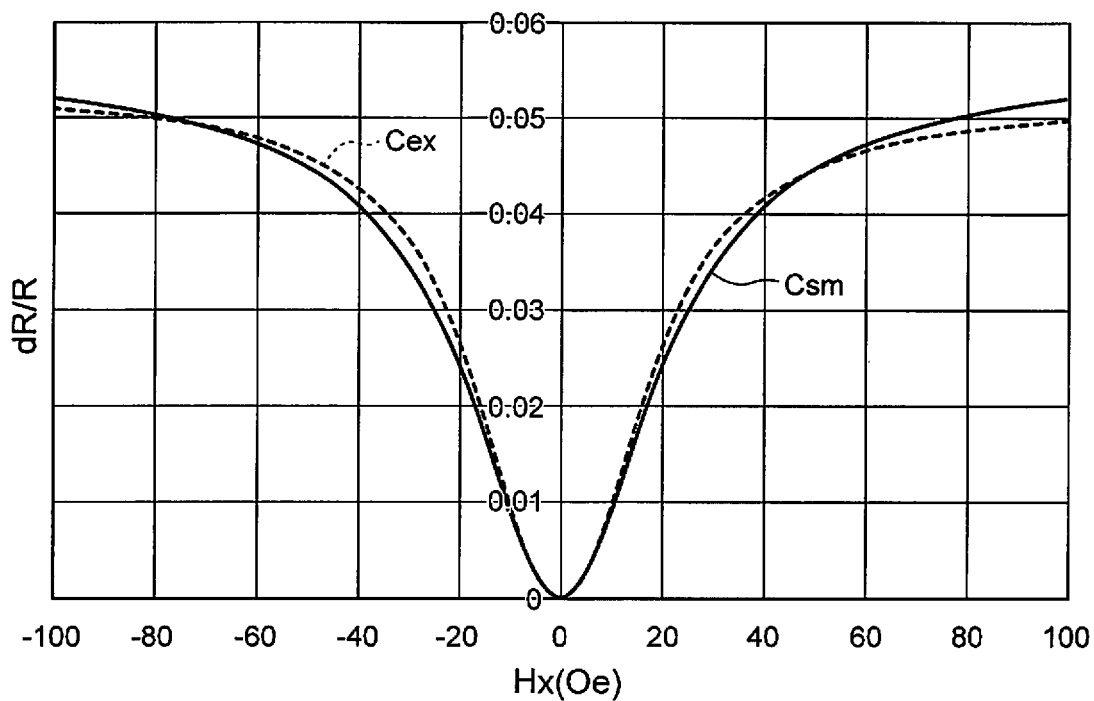
FIG. 11 is a graph illustrating a characteristic of the magnetic sensor.

FIG. 11 is a graph illustrating a characteristic of the magnetic sensor.

FIG. 11 illustrates the magnetic field-electrical resistance characteristic of the element obtained as recited above. The horizontal axis of FIG. 11 corresponds to the magnetic field Hx applied to the element. The vertical axis is a ratio of the electric resistance change dR/R. In FIG. 11, only the resistance change excluding the constant resistance component R0 of FIG. 4 is plotted. R is the electrical resistance when the magnetic field Hx is 0. dR is the difference in the electric resistance between the electrical resistance when the magnetic field is Hx and the electrical resistance when the magnetic field Hx is 0. A characteristic Cex measured for the element example is illustrated in FIG. 11. As shown in FIG. 11, the element has an even-function characteristic.

A characteristic Csm (an approximate characteristic) calculated by the following analytic formula (1) is also shown in FIG. 11.

$$d/dR = 0.055 \times (1 - \{-2|Hx|/30 + ((2Hx/30)^2 + 4)^{1/2} + 4\}^2)^{2.5} \quad (1)$$

As shown in FIG. 11, the characteristic Csm by the analytic formula matches the measured result Cex well. Accordingly, the characteristic of the example element can be simulated with high precision by the analytic formula.

An example of simulation results using the analytic formula will now be described. In the simulation, the magnetic field Hm of the measurement object is assumed to have only a direct current (DC) component Hdc (Hm=Hdc). The orientation of an AC magnetic field Hac is aligned with the orientation of the DC component Hdc. The AC magnetic field Hac is represented by the following Formula (2).

$$Hac = Hac0 \times \{\sin(2\pi \times tmd/64)\} \quad (2)$$

In Formula (2), a time tmd is a dimensionless number. The period of the AC magnetic field Hac is tmd=64. In the simulation, Hac0=10 Oe (oersteds); and Hdc=1 Oe. The electrical resistance is normalized in the simulation. In the simulation model, the phases of the AC magnetic fields (the first AC magnetic field Ha1 and the second AC magnetic field Ha2) applied to the two elements are opposite to each other (the configuration of FIG. 8A).

Figure 12:
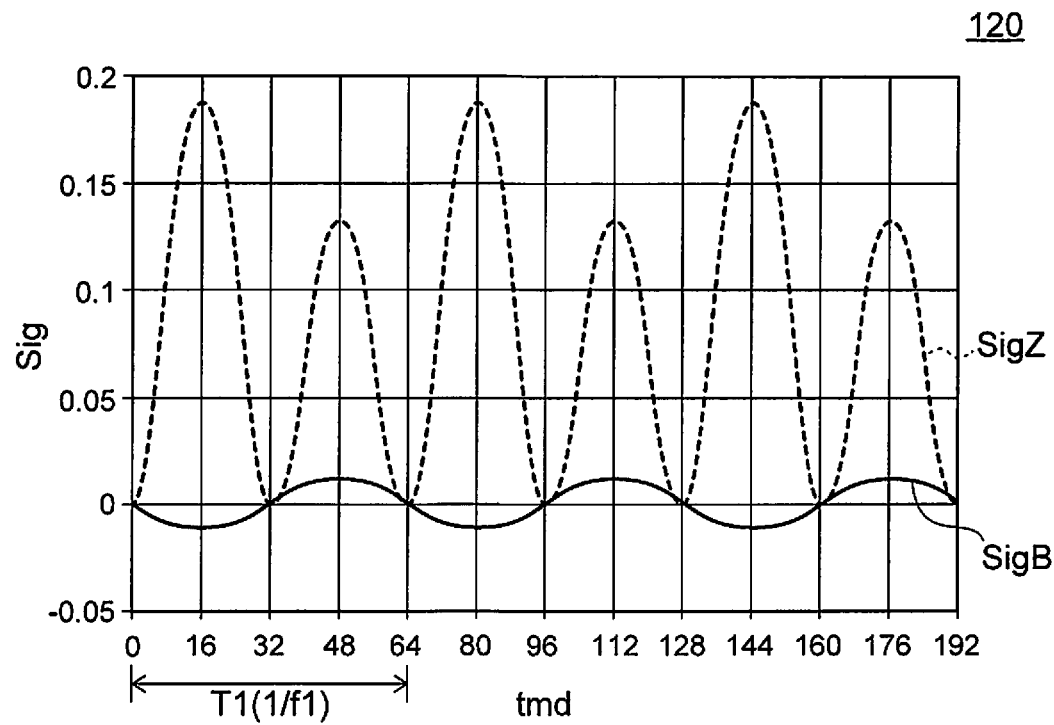
FIG. 12 is a graph illustrating characteristics of the magnetic sensor.

FIG. 12 is a graph illustrating characteristics of the magnetic sensor.

FIG. 12 illustrates simulation results of the characteristics of the magnetic sensor 120 illustrated in FIG. 9. The horizontal axis of FIG. 12 is the time tmd. The time period in which the time tm is 0 to 64 corresponds to the period T1 (1/f1). The vertical axis of FIG. 12 is the signal Sig obtained from the magnetic sensor 120. A signal SigZ that corresponds to the electric potential of the first element end portion 51a of the first element 51 (referring to FIG. 9) is illustrated in FIG. 12. The signal SigZ corresponds to the change in the voltage between the two ends of an element. Further, the signal SigB corresponding to the difference in the electric potential between the first connection point CP1 and the second connection point CP2 (referring to FIG. 9) is illustrated in FIG. 12.

As shown in FIG. 12, two types of frequency components exist in the voltage (the signal SigZ) between the two ends of an element (the first element 51). The signal SigZ has components of the AC magnetic field with the first frequency f1 and the double frequency 2f1.

Conversely, in the signal SigB, the double frequency 2f1 is not observed; and a component of the first frequency f1 is observed.

Figure 13A:
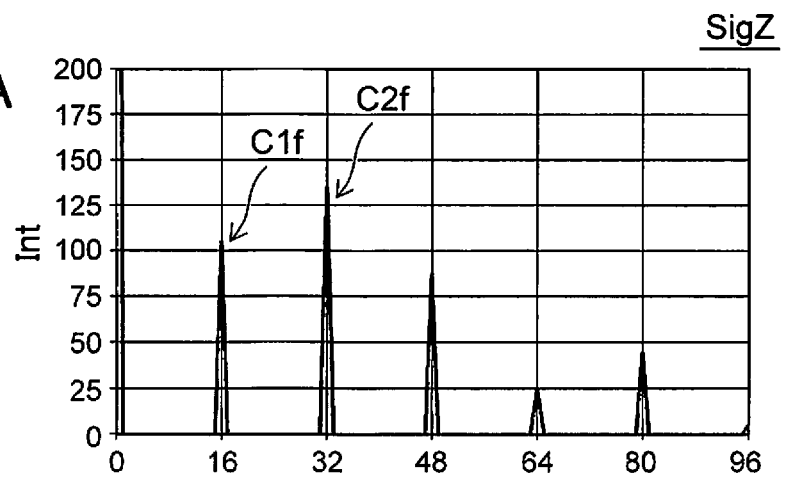
FIG. 13A and FIG. 13B are graphs illustrating characteristics of the magnetic sensor.
Figure 13B:
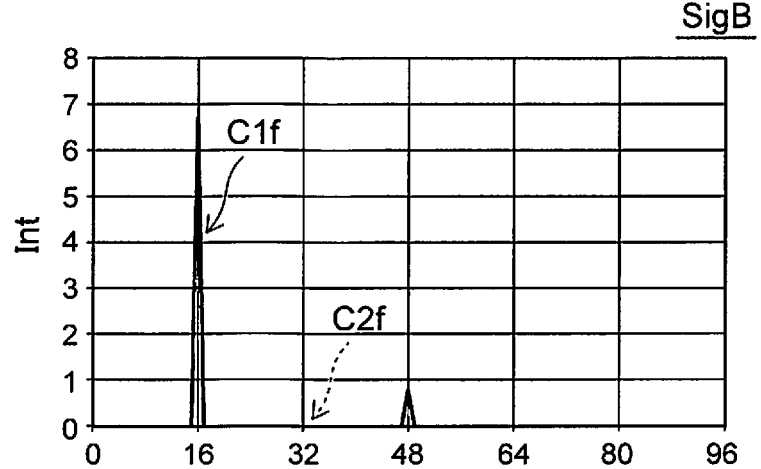

FIG. 13A and FIG. 13B are graphs illustrating characteristics of the magnetic sensor.

These figures illustrate results of FFT analysis of the signals SigZ and SigB illustrated in FIG. 12. In these figures, the horizontal axis corresponds to the frequency component of the time tmd. In these figures, the vertical axis corresponds to the intensity of each frequency components.

As shown in FIG. 13A, the signal SigZ has the double frequency (2f1) component Cf2 as well as the first frequency (f1) component Cf1. The component Cf2 is larger than the component Cf1.

Conversely, as shown in FIG. 13B, the signal SigB does not have the double frequency (2f1) component Cf2; and has large first frequency (f1) component. In the example, a signal corresponds to the frequency of 3 times the first frequency f1 is observed due to the nonlinearity of the magneto-resistance characteristic shown in FIG. 11.

For example, by filtering of the signal SigZ, the component of the double frequency 2f1 can be removed; and the component of the first frequency f1 can be extracted. Conversely, in the case for the signal SigB, the double frequency 2f1 is substantially not generated; therefore, the component of the first frequency f1 is obtained even without the filtering operation.

In the embodiment, the component of the double frequency 2f1 is substantially not generated. For example, amplification of the signal is easy. For example, the design of the amplifier is easy. For example, the influence of the distortion and/or the error are suppressed. It is easy to amplify a signal with high SN ratio. Conversely, in the case when the double frequency (2f1) component exist as illustrated in FIG. 13A, it is difficult to amplify the first frequency (f1) component effectively. For example, the distortion or the noise easily becomes large.

A bridge configuration is applied in the example of the magnetic sensor 120. Thereby, as illustrated in FIG. 12, the DC component of the signal SigB substantially can be removed. For example, a faint detection signal can be largely amplified without applying a DC filtering.

The magnetic field detection sensitivity that is derived from the characteristic of the experiment sample shown in FIG. 11 is about 10 nV/nT. Since the magneto-resistance effect does not have frequency dependence, the sensitivity is kept even in the case of the AC magnetic field with 100 kHz. Considering that the noise of the element is about 1 nT at 100 kHz, the detection limit (the measurable magnetic field strength) is about 90 pT.

FIG. 14A to FIG. 14D are schematic perspective views illustrating portions of a magnetic sensor according to the first embodiment.

Figure 14A:
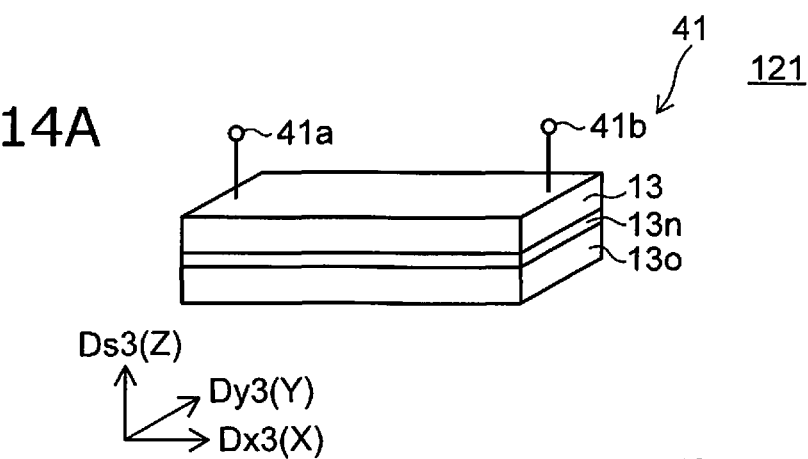
FIG. 14A to FIG. 14D are schematic perspective views illustrating portions of a magnetic sensor according to the first embodiment.

In the magnetic sensor 121 according to the embodiment as shown in FIG. 14A, the first resistor 41 may include a third magnetic layer 13, a third opposing magnetic layer 13o, and a third nonmagnetic layer 13n. The third nonmagnetic layer 13n is provided between the third magnetic layer 13 and the third opposing magnetic layer 13o. The direction from the third opposing magnetic layer 13o toward the third magnetic layer 13 is taken as a third stacking direction Ds3 (e.g., the Z-axis direction).

Figure 14B:
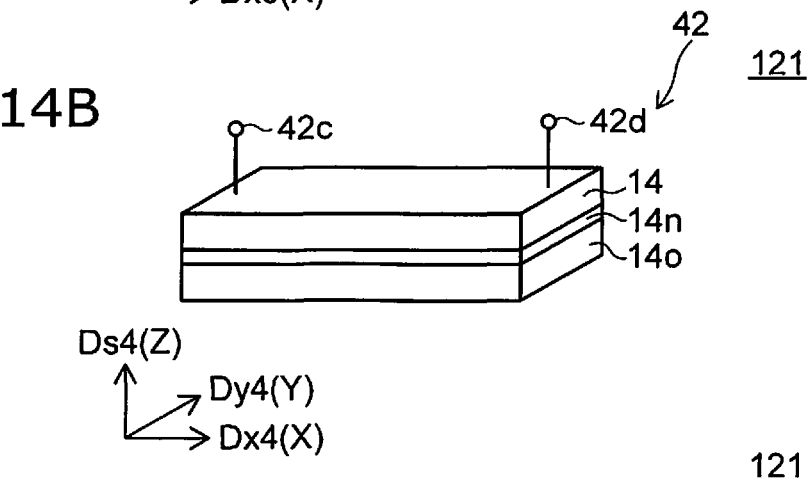
Figure 14C:
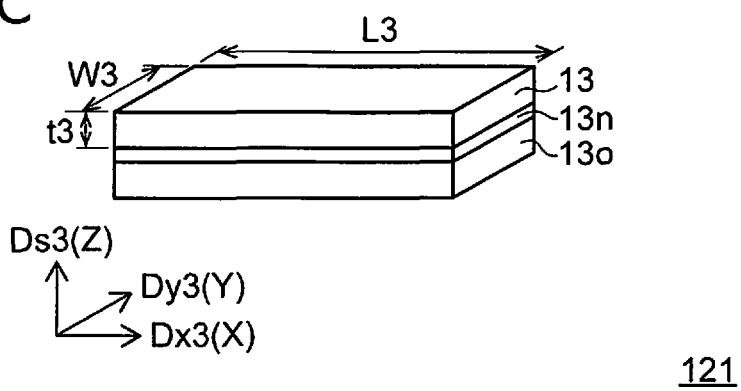

In one example as shown in FIG. 14C, a length L3 of the third magnetic layer 13 along a third magnetic layer direction Dx3 is longer than a length W3 of the third magnetic layer 13 along a third magnetic layer cross direction Dy3. The length W3 is, for example, the width. The length L3 of the third magnetic layer 13 along the third magnetic layer direction Dx3 is longer than a length t3 of the third magnetic layer 13 along the third stacking direction Ds3. The length t3 is, for example, the thickness. The length W3 is longer than the length t3. The third magnetic layer direction Dx3 is, for example, the major-axis direction of the element. The third magnetic layer cross direction Dy3 is, for example, the minor-axis direction of the element. The third stacking direction Ds3 is, for example, the thickness direction of the element.

The lengths along the third magnetic layer direction Dx3 of the third opposing magnetic layer 13o and the third nonmagnetic layer 13n may be substantially the same as the length L3. The lengths along the third magnetic layer cross direction Dy3 of the third opposing magnetic layer 13o and the third nonmagnetic layer 13n may be substantially the same as the length W3. The lengths along the third stacking direction Ds3 of the third opposing magnetic layer 13o and the third nonmagnetic layer 13n may be substantially the same as the length t3.

As shown in FIG. 14A, for example, the direction from the first resistor end portion 41a toward the second resistor end portion 41b is aligned with the third magnetic layer direction Dx3 (e.g., the X-axis direction).

In the magnetic sensor 121 as shown in FIG. 14B, the second resistor 42 may include a fourth magnetic layer 14, a fourth opposing magnetic layer 14o, and a fourth nonmagnetic layer 14n. The fourth nonmagnetic layer 14n is provided between the fourth magnetic layer 14 and the fourth opposing magnetic layer 14o. The direction from the fourth opposing magnetic layer 14o toward the fourth magnetic layer 14 is taken as a fourth stacking direction Ds4 (e.g., the Z-axis direction).

Figure 14D:
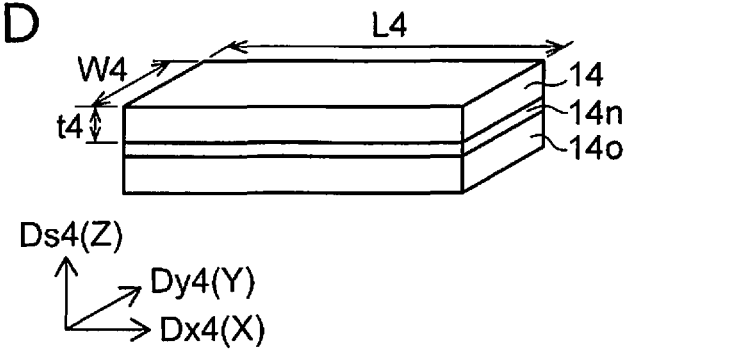

In one example as shown in FIG. 14D, a length L4 of the fourth magnetic layer 14 along a fourth magnetic layer direction Dx4 is longer than a length W4 of the fourth magnetic layer 14 along a fourth magnetic layer cross direction Dy4. The length W4 is, for example, the width. The length L4 of the fourth magnetic layer 14 along the fourth magnetic layer direction Dx4 is longer than a length t4 of the fourth magnetic layer 14 along the fourth stacking direction Ds4. The length t4 is, for example, the thickness. The length W4 is longer than the length t4. The fourth magnetic layer direction Dx4 is, for example, the major-axis direction of the element. The fourth magnetic layer cross direction Dy4 is, for example, the minor-axis direction of the element. The fourth stacking direction Ds4 is, for example, the thickness direction of the element.

The lengths along the fourth magnetic layer direction Dx4 of the fourth opposing magnetic layer 14o and the fourth nonmagnetic layer 14n may be substantially the same as the length L4. The lengths along the fourth magnetic layer cross direction Dy4 of the fourth opposing magnetic layer 14o and the fourth nonmagnetic layer 14n may be substantially the same as the length W4. The lengths along the fourth stacking direction Ds4 of the fourth opposing magnetic layer 14o and the fourth nonmagnetic layer 14n may be substantially the same as the length t4.

As shown in FIG. 14B, for example, the direction from the third resistor end portion 42c toward the fourth resistor end portion 42d is aligned with the fourth magnetic layer direction Dx4 (e.g., the X-axis direction).

The configuration (including the material) of the first magnetic layer 11 is applicable to at least one of the third magnetic layer 13 or the fourth magnetic layer 14. The configuration (including the material) of the first opposing magnetic layer 11o is applicable to at least one of the third opposing magnetic layer 13o or the fourth opposing magnetic layer 14o. The configuration (including the material) of the first nonmagnetic layer 11n is applicable to at least one of the third nonmagnetic layer 13n or the fourth nonmagnetic layer 14n. The manufacturing is easy when using resistors such as those recited above that include magnetic layers.

In the magnetic sensor 121, for example, the magnetization of the third opposing magnetic layer 13o and the magnetization of the fourth opposing magnetic layer 14o may be aligned with the Y-axis direction. Thereby, for example, the change of the electrical resistances of the first resistor 41 and the second resistor 42 with respect to the magnetic field Hm applied from the outside can be suppressed.

In the embodiment, these resistors may not include magnetic layers. These resistors may include, for example, silicon. For example, these resistors may be formed of a metal, etc.

FIG. 15A, FIG. 15B, FIG. 16A, and FIG. 16B are schematic views illustrating portions of a magnetic sensor according to the first embodiment.

Figure 15A:
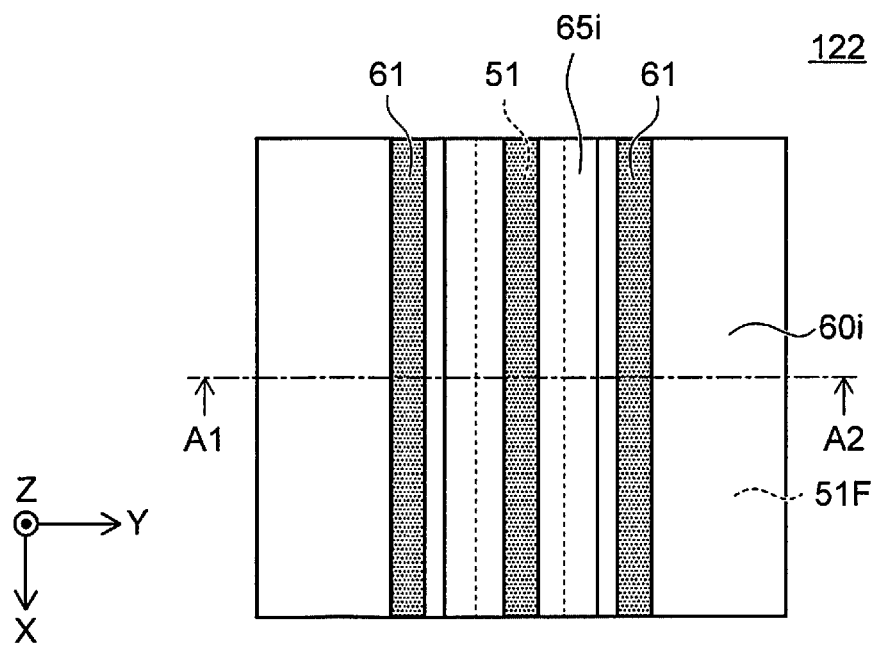
FIG. 15A and FIG. 15B are schematic views illustrating portions of a magnetic sensor according to the first embodiment.
Figure 15B:
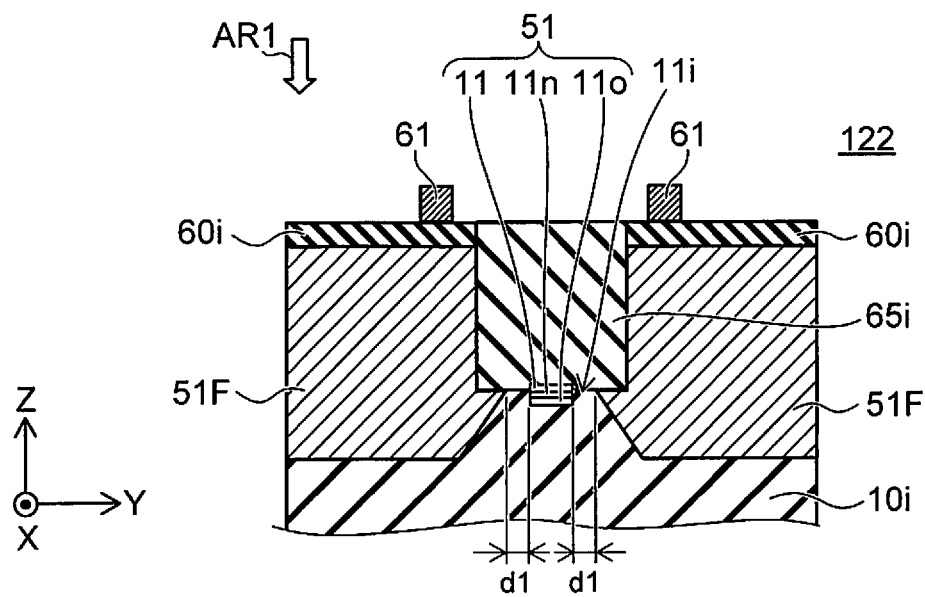
Figure 16A:
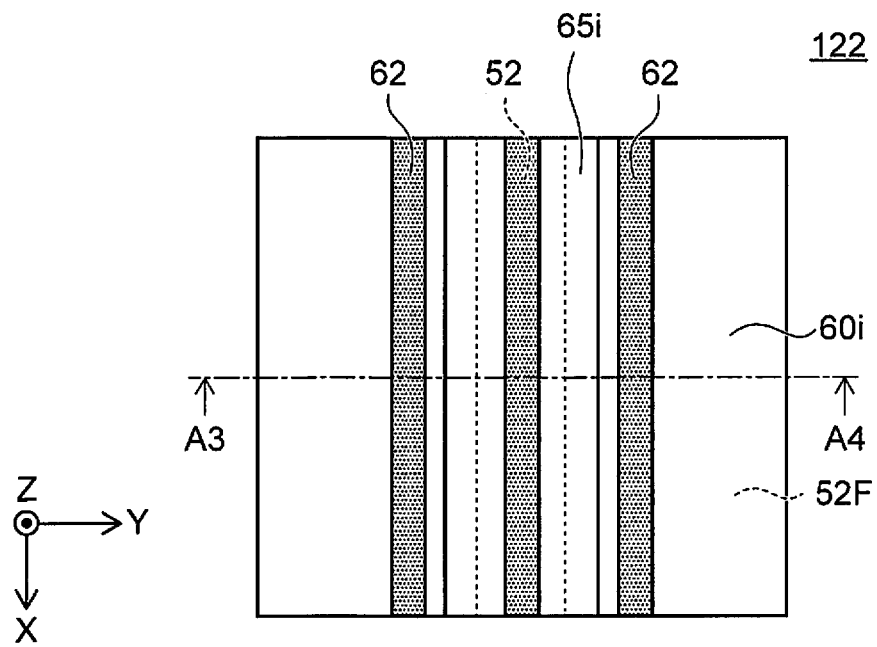
FIG. 16A and FIG. 16B are schematic views illustrating portions of the magnetic sensor according to the first embodiment.
Figure 16B:
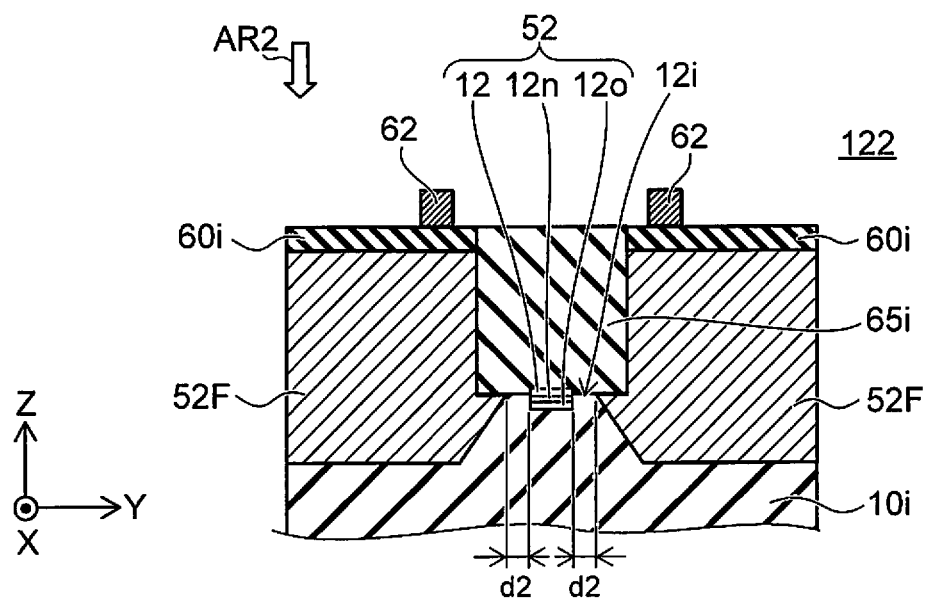

FIG. 15A is a plan view as viewed along arrow AR1 of FIG. 15B. FIG. 15B is a line A1-A2 cross-sectional view of FIG. 15A. FIG. 16A is a plan view as viewed along arrow AR2 of FIG. 16B. FIG. 16B is a line A3-A4 cross-sectional view of FIG. 16A.

As shown in these figures, a first magnetic portion 51F, a first nonmagnetic region 11i, a second magnetic portion 52F, and a second nonmagnetic region 12i are provided in the magnetic sensor 122 according to the embodiment.

As shown in FIG. 15B, the first nonmagnetic region 11i is provided between the first magnetic portion 51F and the first element 51. The thickness (a distance d1) of the first nonmagnetic region 11i along the direction from the first element 51 toward the first magnetic portion 51F is, for example, 10 nm or less.

As shown in FIG. 16B, the second nonmagnetic region 12i is provided between the second magnetic portion 52F and the second element 52. The thickness (a distance d2) of the second nonmagnetic region 12i along the direction from the second element 52 toward the second magnetic portion 52F is, for example, 10 nm or less.

An insulating portion 10i is provided in the example as shown in FIG. 15B and FIG. 16B. The first element 51 and the second element 52 are provided on a portion of the insulating portion 10i. The first magnetic portion 51F and the second magnetic portion 52F are provided on another portion of the insulating portion 10i. The first element 51 is provided between two regions of the first magnetic portion 51F. The second element 52 is provided between two regions of the second magnetic portion 52F. An insulating member 65i is provided on the first element 51 and the second element 52. The insulating member 65i is provided between two regions of the first magnetic portion 51F. The insulating member 65i is provided between two regions of the second magnetic portion 52F.

An insulating layer 60i is provided on the first magnetic portion 51F and on the second magnetic portion 52F. The first interconnect 61 is provided on the insulating layer 60i to correspond to the first element 51. The second interconnect 62 is provided on the insulating layer 60i to correspond to the second element 52.

The first magnetic portion 51F and the second magnetic portion 52F include, for example, at least one selected from the group consisting of a NiFe alloy, an FeCo alloy, and a CoZrNb alloy. The first magnetic portion 51F and the second magnetic portion 52F include, for example, amorphous alloys. The first magnetic portion 51F and the second magnetic portion 52F include, for example, materials having high permeabilities. The first magnetic portion 51F and the second magnetic portion 52F include, for example, soft magnetic materials. Due to the high permeability, for example, the external magnetic fields concentrate easily in the portion of the first element 51 and the second element 52. For example, the first magnetic portion 51F and the second magnetic portion 52F function as MFCs (Magnetic Flux Concentrators). The permeability of the NiFe-based alloy is greater than 1000.

By providing the first magnetic portion 51F and the second magnetic portion 52F, for example, the AC magnetic fields and the magnetic field Hm from the detection object concentrate efficiently in the first element 51 and the second element 52. In the example described in reference to FIG. 14A to FIG. 14D in which magnetic layers are used in the first resistor 41 and the second resistor 42, the magnetic portions (e.g., the MFCs) may not be provided in the first resistor 41 and the second resistor 42. Thereby, the change in the electrical resistances of these resistors can be suppressed.

For example, the magnetic flux that reaches the first magnetic portion 51F and the second magnetic portion 52F concentrated to these magnetic portions. For example, the flux concentrates in the gap between the magnetic portion and the element (the first element 51 or the second element). For example, a magnetic portion (a MFC) having a size that is not less than 10 times and not more than 1000 times the width of the gap is provided. For example, a magnetic field enhancement effect that is not less than 10 times and not more than 1000 times is obtained.

For example, the distances (the distance d1 and the distance d2) between the elements and the magnetic portions are, for example, 10 nm or less. Thereby, the magnetic field concentrating effect is obtained effectively. For example, the distances between the elements and the magnetic portions are long enough that the exchange coupling interaction does not exert.

In the example of the magnetic sensor 122, at least a portion of the first interconnect 61 and the first element 51 does not overlap in the Z-axis direction. At least a portion of the second interconnect 62 and the second element 52 does not overlap in the Z-axis direction. The manufacturing of such a configuration is easy.

The thicknesses in the Z-axis direction of the first magnetic portion 51F and the second magnetic portion 52F are thicker than the thicknesses in the Z-axis direction of the first element 51 and the second element 52. Thereby, for example, the magnetic field concentrating effect is obtained effectively.

FIG. 17A to FIG. 17D are schematic views illustrating portions of the magnetic sensor according to the first embodiment.

Figure 17A:
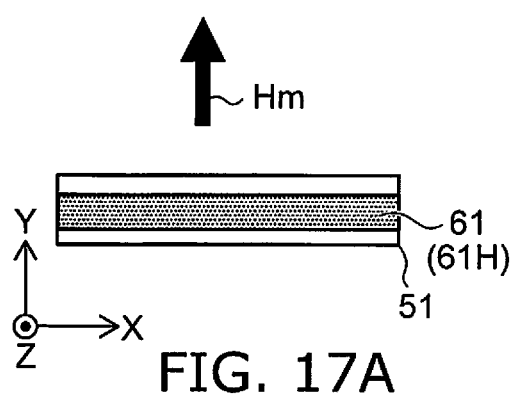
FIG. 17A and FIG. 17D are schematic views illustrating portions of the magnetic sensor according to the first embodiment.
Figure 17B:
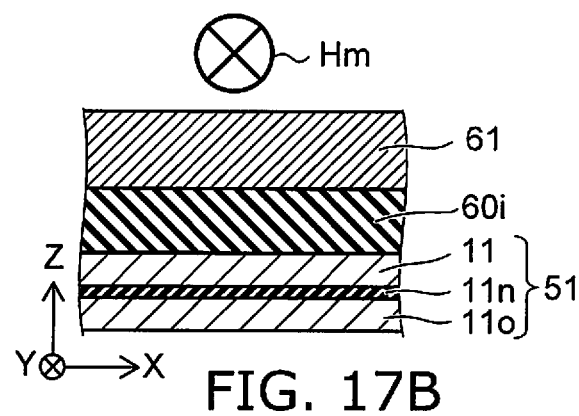
Figure 17C:
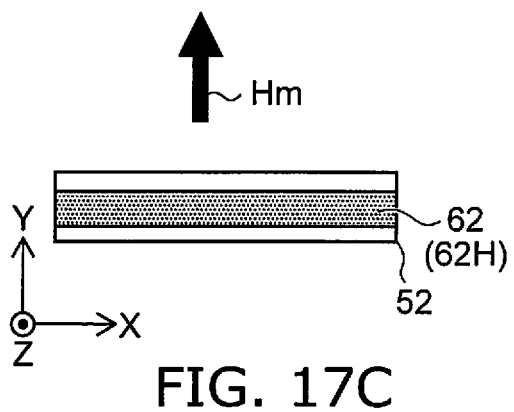
Figure 17D:
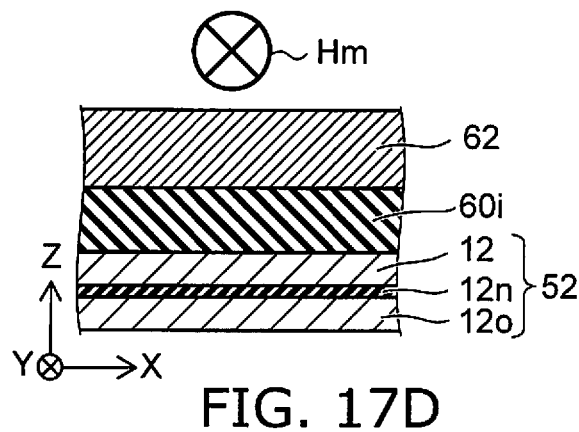

FIG. 17A and FIG. 17C are plan views. FIG. 17B and FIG. 17D are cross-sectional views. As shown in FIG. 17B, the insulating layer 60i may be provided between the first element 51 and the first interconnect 61. As shown in FIG. 17D, the insulating layer 60i may be provided between the second element 52 and the second interconnect 62. As shown in FIG. 17A and FIG. 17C, the length (the width) in the Y-axis direction of the first element 51 and the length (the width) in the Y-axis direction of the second element 52 respectively may be wider than the length (the width) in the Y-axis direction of the first interconnect 61 and the length (the width) in the Y-axis direction of the second interconnect 62.

For example, the magnetic field Hm along the Y-axis direction is applied to these elements. The AC magnetic fields that are generated from the first interconnect 61 (the first magnetic field generator 61H) and the second interconnect 62 (the second magnetic field generator 62H) have components along the direction of the magnetic field Hm.

Figure 18A:
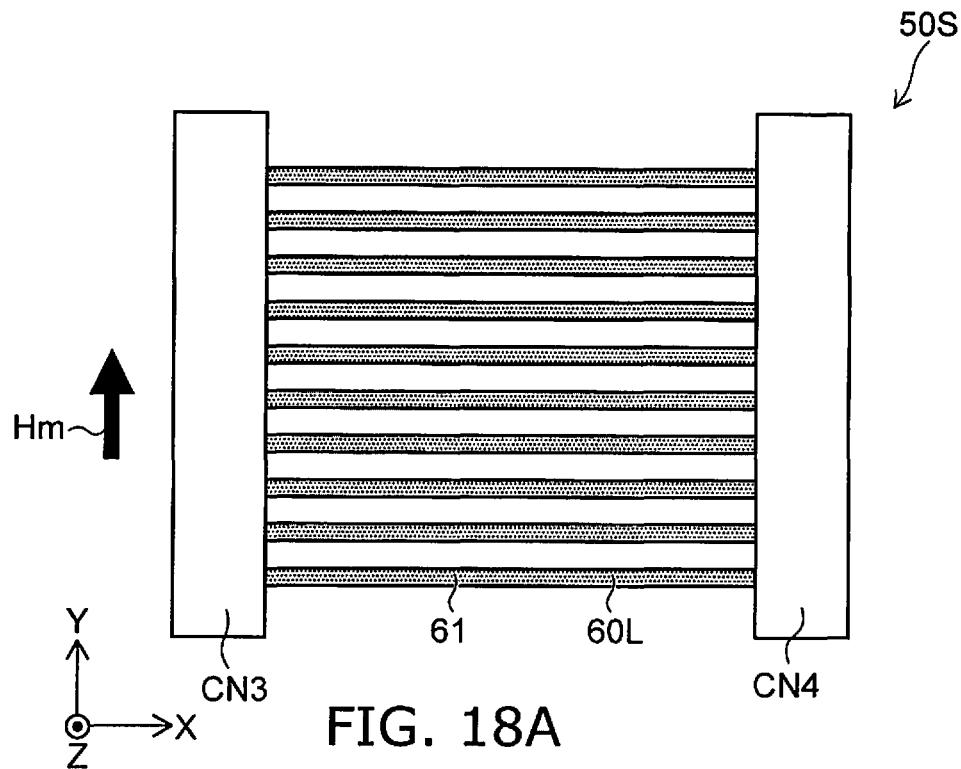
FIG. 18A and FIG. 18B are schematic views illustrating a portion of the magnetic sensor according to the first embodiment.
Figure 18B:
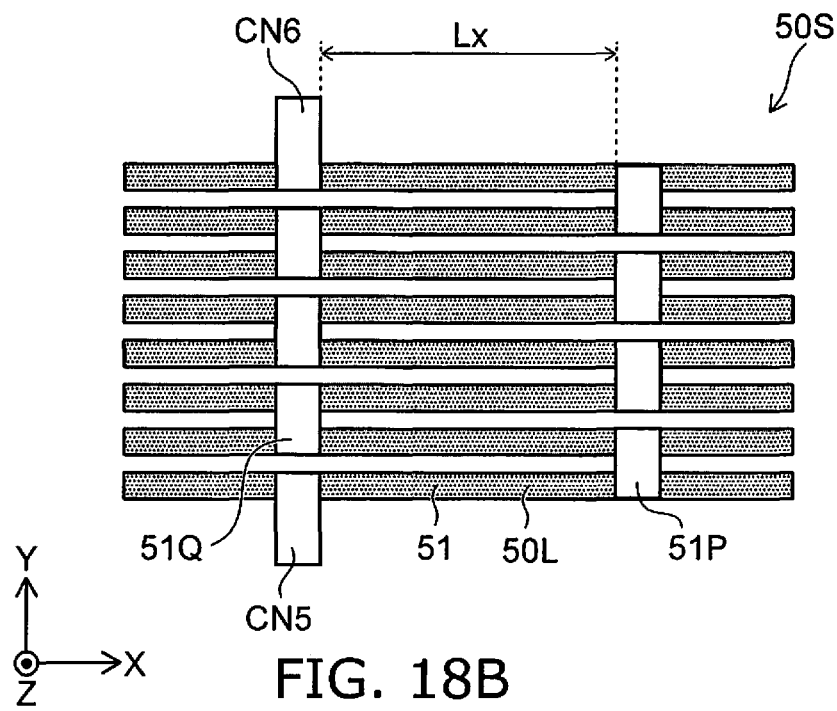

FIG. 18A and FIG. 18B are schematic views illustrating a portion of the magnetic sensor according to the first embodiment.

These figures illustrate the layout of the first interconnects 61 and the first elements 51. For easier viewing in these figures, the first interconnects 61 and the first elements 51 are illustrated separately. FIG. 18A illustrates the first interconnects 61. FIG. 18B illustrates the first elements 51. The structure (a detector 50S) illustrated in FIG. 18A and the structure (the detector 50S) illustrated in FIG. 18B overlap in the Z-axis direction.

As shown in FIG. 18A, conductive portions 60L that have multiple band configurations extending along the X-axis direction are provided. Each of the conductive portions 60L having the multiple band configurations corresponds to at least a portion of the first interconnect 61. In the example, the conductive portions 60L that have the multiple band configurations are electrically connected by a connecting conductive portion CN3 at one end. The conductive portions 60L that have the multiple band configurations are electrically connected by a connecting conductive portion CN4 at another end. For example, a current (an alternating current) is supplied between the connecting conductive portion CN3 and the connecting conductive portion CN4. The current is supplied by the first circuit portion 71. By supplying the current, the current (the alternating current) flows in the conductive portions 60L (e.g., the first interconnects 61) having the multiple band configurations. The multiple first interconnects 61 are arranged alternately in the Y-axis direction.

As shown in FIG. 18B, structure bodies 50L that have multiple band configurations extending along the X-axis direction are provided. One of the structure bodies 50L having the multiple band configurations corresponds to at least a portion of the first element 51. In the example, an end of one of the structure bodies 50L having the multiple band configurations is electrically connected by a connection member 51P to an end of another one of the structure bodies 50L having the multiple band configurations. Another end of the other one of the structure bodies 50L having the multiple band configurations recited above is electrically connected by a connection member 51Q to an end of yet another one of the structure bodies 50L having the multiple band configurations. The multiple first elements 51 are arranged alternately in the Y-axis direction. These elements are arranged in series in a folded zigzag configuration.

For example, a connecting conductive portion CN6 (a terminal) is electrically connected to one end of the first elements 51. A connecting conductive portion CN5 (a terminal) is electrically connected to another end of the first elements 51. For example, a current is supplied between these terminals. For example, the current is supplied by the second circuit portion 72.

The width (e.g., the length in the Y-axis direction) of one of the conductive portions 60L having the multiple band configurations is, for example, about 5 µm. The spacing (e.g., the length in the Y-axis direction) between the conductive portions 60L having the multiple band configurations is, for example, about 8 µm. The length (e.g., the length in the X-axis direction) of one of the conductive portions 60L is about 150 µm. The number of the conductive portions 60L having the multiple band configurations is, for example, 10. The AC magnetic field that is generated by the current (the alternating current) flowing in the conductive portions 60L having the multiple band configurations has a component along the Y-axis direction. For example, the magnetic field Hm from the detection object has a Y-axis direction component.

The width (e.g., the length in the Y-axis direction) of one of the structure bodies 50L having the multiple band configurations is, for example, about 8 µm. The spacing (e.g., the length in the Y-axis direction) between the structure bodies 50L having the multiple band configurations is, for example, about 3 µm. An effective length Lx of the structure bodies 50L having the multiple band configurations is about 100 µm. For example, the first elements 51 and the second elements 52 are formed from the structure bodies 50L having the multiple band configurations. The electrical resistances of the first elements 51 and the second element 52 are about 680Ω.

Figure 19:
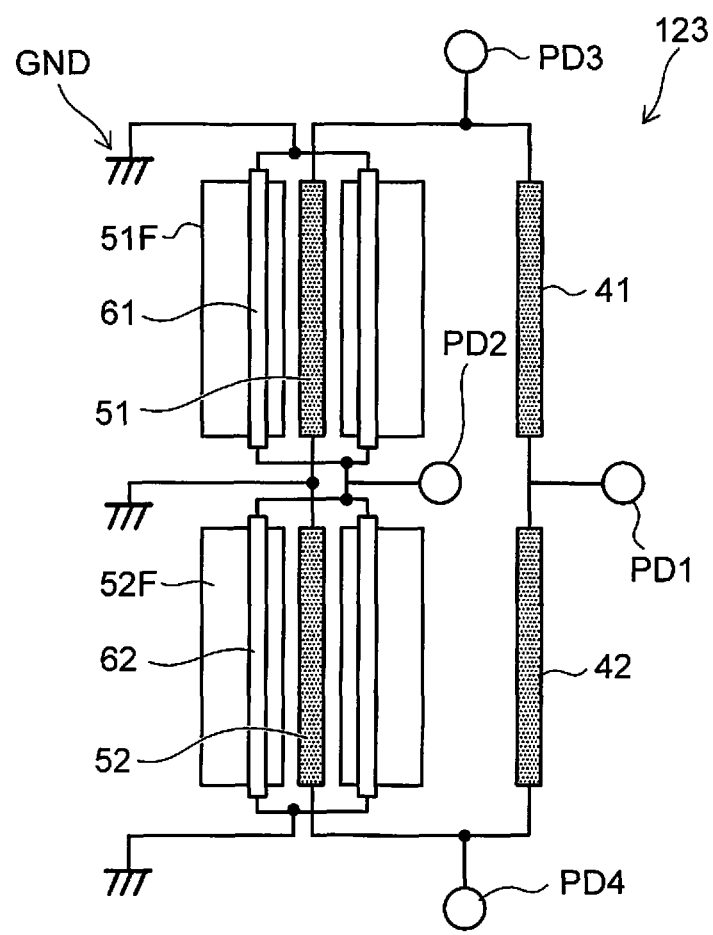
FIG. 19 is a schematic view illustrating a portion of a magnetic sensor according to the first embodiment.

FIG. 19 is a schematic view illustrating a portion of a magnetic sensor according to the first embodiment.

As shown in FIG. 19, the first interconnects 61, the second interconnects 62, the first element 51, the second element 52, the first resistor 41, and the second resistor 42 are provided in the magnetic sensor 123 according to the embodiment. First to fourth pads PD1 to PD4 are provided in the example.

The first interconnects 61 are electrically connected to the second pad PD2 at one end portion. The first interconnects 61 are electrically connected to ground (the ground GND) at another end portion. The second interconnects 62 are electrically connected to the second pad PD2 at one end portion. The second interconnects 62 are electrically connected to ground (the ground GND) at another end portion. The one end portions of the first interconnects 61 recited above and the one end portions of the second interconnects 62 recited above are provided between the other end portions of the first interconnects 61 recited above and the other end portions of the second interconnects 62 recited above.

One end portion of the first element 51 is electrically connected to the third pad PD3. Another end portion of the first element 51 is electrically connected to ground (the ground GND). One end portion of the second element 52 is electrically connected to the fourth pad PD4. Another end portion of the second element 52 is electrically connected to ground (the ground GND). The other end portion of the first element 51 recited above and the other end portion of the second element 52 recited above are provided between the one end portion of the first element 51 recited above and the one end portion of the second element 52 recited above.

One end portion of the first resistor 41 is electrically connected to the third pad PD3. Another end portion of the first resistor 41 is electrically connected to a first pad PD1. One end portion of the second resistor 42 is electrically connected to the fourth pad PD4. Another end portion of the second resistor 42 is electrically connected to the first pad PD1. The other end portion of the first resistor 41 recited above and the other end portion of the second resistor 42 recited above are provided between the one end portion of the first resistor 41 recited above and the one end portion of the second resistor 42 recited above.

For example, the second pad PD2 is electrically connected to the first circuit portion 71. An alternating current is supplied to the second pad PD2. This alternating current becomes the first alternating current Ia1 in the first interconnects 61. This alternating current becomes the second alternating current Ia2 in the second interconnects 62.

One bridge is formed of the first element 51, the second element 52, the first resistor 41, and the second resistor 42. The third pad PD3 and the fourth pad PD4 are electrically connected to the second circuit portion 72. A current is supplied between these pads. The current becomes the first current Id1 in the first element 51. The current becomes the second current Id2 in the second element 52. For example, the second circuit portion 72 is a constant voltage source.

The first pad PD1 and the second pad PD2 are electrically connected to the third circuit portion 73. The first pad PD1 and the second pad PD2 correspond to midpoints of the bridge. A signal is detected by the third circuit portion 73. The component of this signal having the double frequency 2f1 is suppressed. The signal has a component of the first frequency f1.

The first magnetic portion 51F and the second magnetic portion 52F are provided in the magnetic sensor 123. Thereby, the magnetic fields that apply to the first element 51 and the second element 52 are enhanced. The first resistor 41 and the second resistor 42 have configurations including magnetic layers (referring to FIG. 14A to FIG. 14D). In such a case, magnetic portions (e.g., MFCs) are not provided in the first resistor 41 and the second resistor 42. The strengths of the magnetic fields apply to these resistors are smaller than the strengths of the magnetic fields acting on the elements. The electrical resistances of these resistors are stable.

Figure 20A:
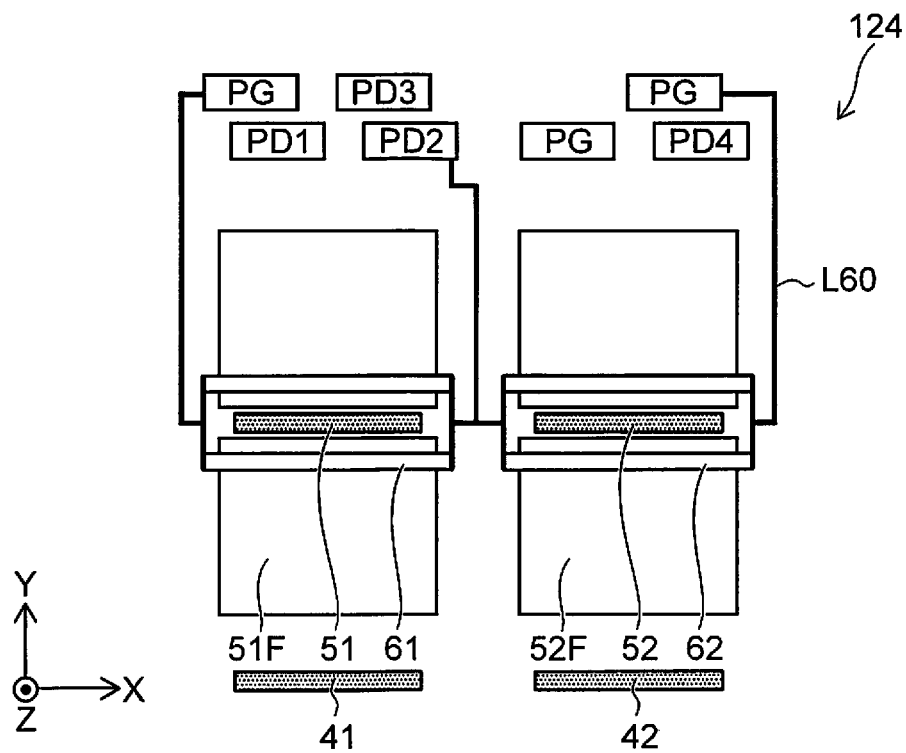
FIG. 20A and FIG. 20B are schematic views illustrating a portion of a magnetic sensor according to the first embodiment.
Figure 20B:
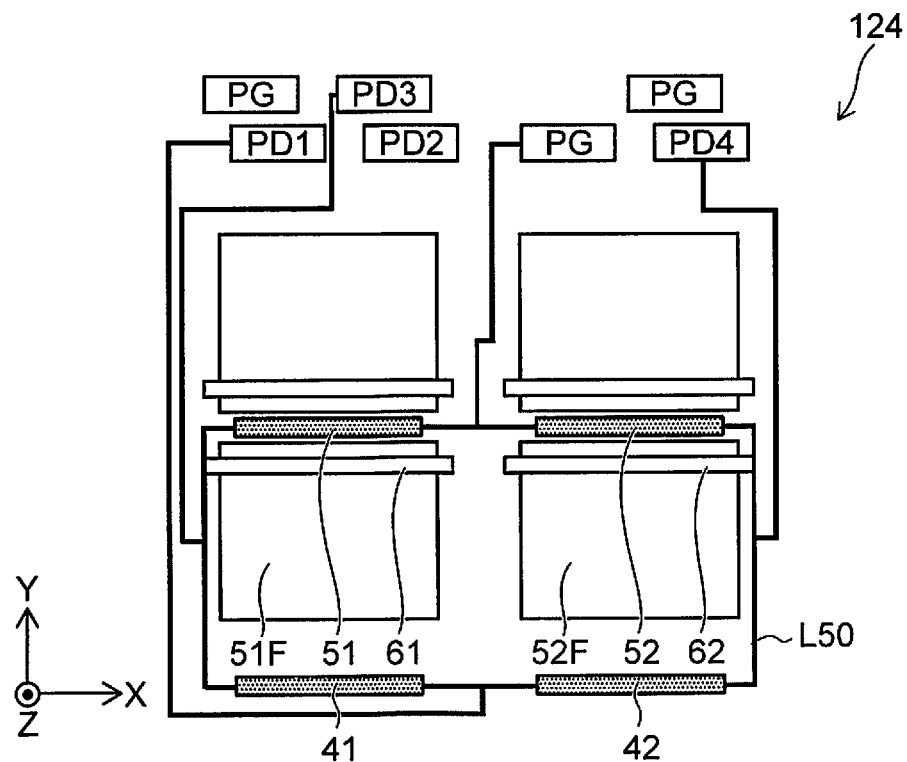

FIG. 20A and FIG. 20B are schematic views illustrating a portion of a magnetic sensor according to the first embodiment.

These figures illustrate the layout of the interconnects of the magnetic sensor 124 according to the embodiment. FIG. 20A illustrates an interconnect L60 electrically connected to the first interconnects 61 and the second interconnects 62. FIG. 20B illustrates an interconnect L50 electrically connected to the first element 51 and the second element 52. For easier viewing in these figures, the structures shown in FIG. 20A and FIG. 20B are illustrated separately. In the actual magnetic sensor 124, the structures shown in FIG. 20A and FIG. 20B overlap along the Z-axis direction with an insulating body interposed.

In these figures, a ground pad PG corresponds to the ground GND and is set to ground. For example, the configuration of the magnetic sensor 123 (referring to FIG. 19) is obtained by the configuration illustrated in FIG. 20A and FIG. 20B.

Second Embodiment

A description is omitted as appropriate for at least a portion of the configuration similar to the configuration described in reference to the first embodiment.

Figure 21:
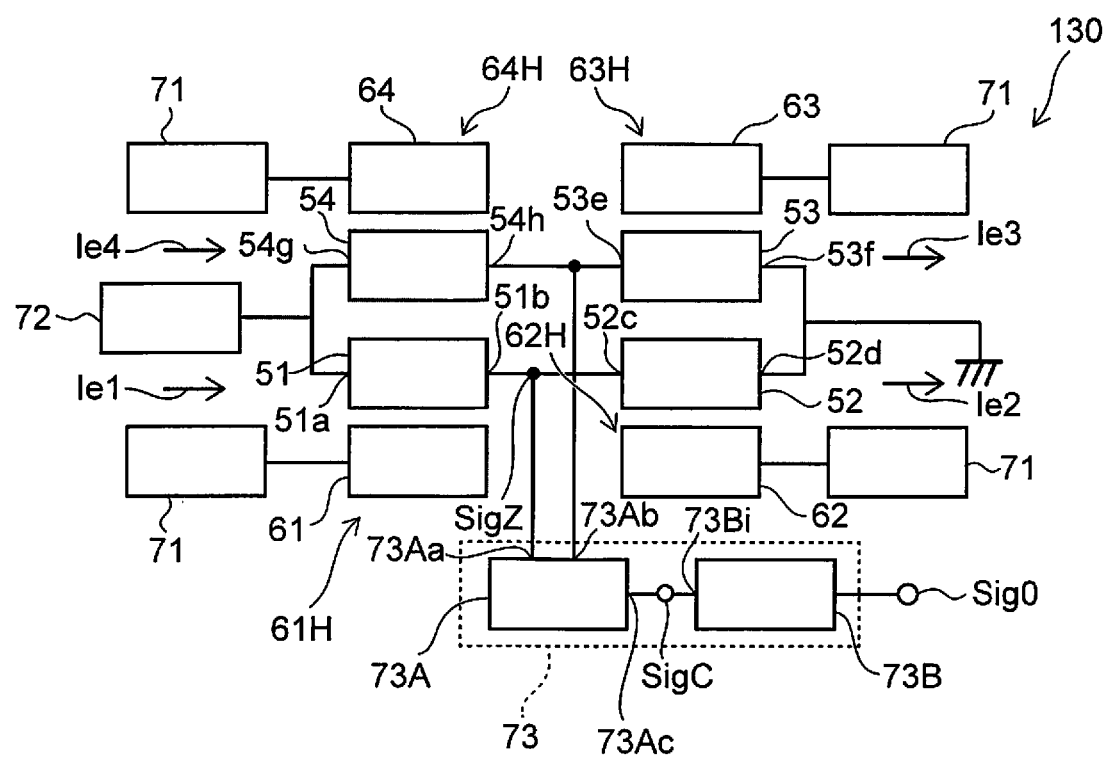
FIG. 21 is a schematic view illustrating a magnetic sensor according to a second embodiment.

FIG. 21 is a schematic view illustrating a magnetic sensor according to a second embodiment.

Figure 22A:
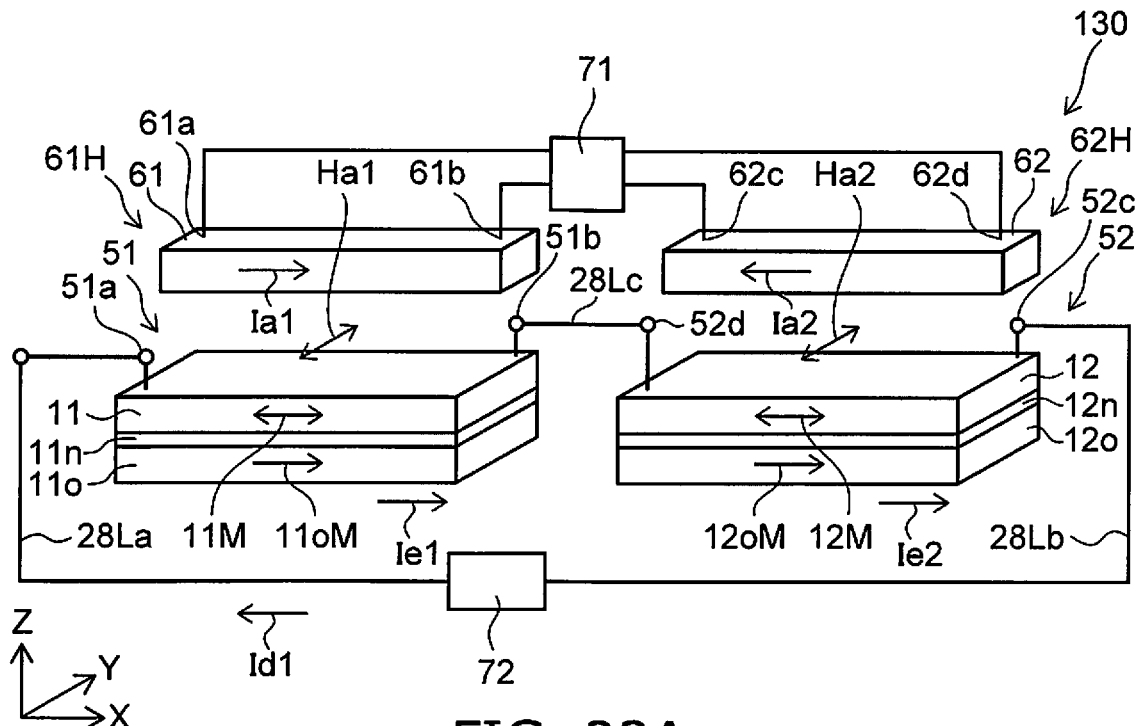
FIG. 22A and FIG. 22B are schematic perspective views illustrating the magnetic sensor.
Figure 22B:
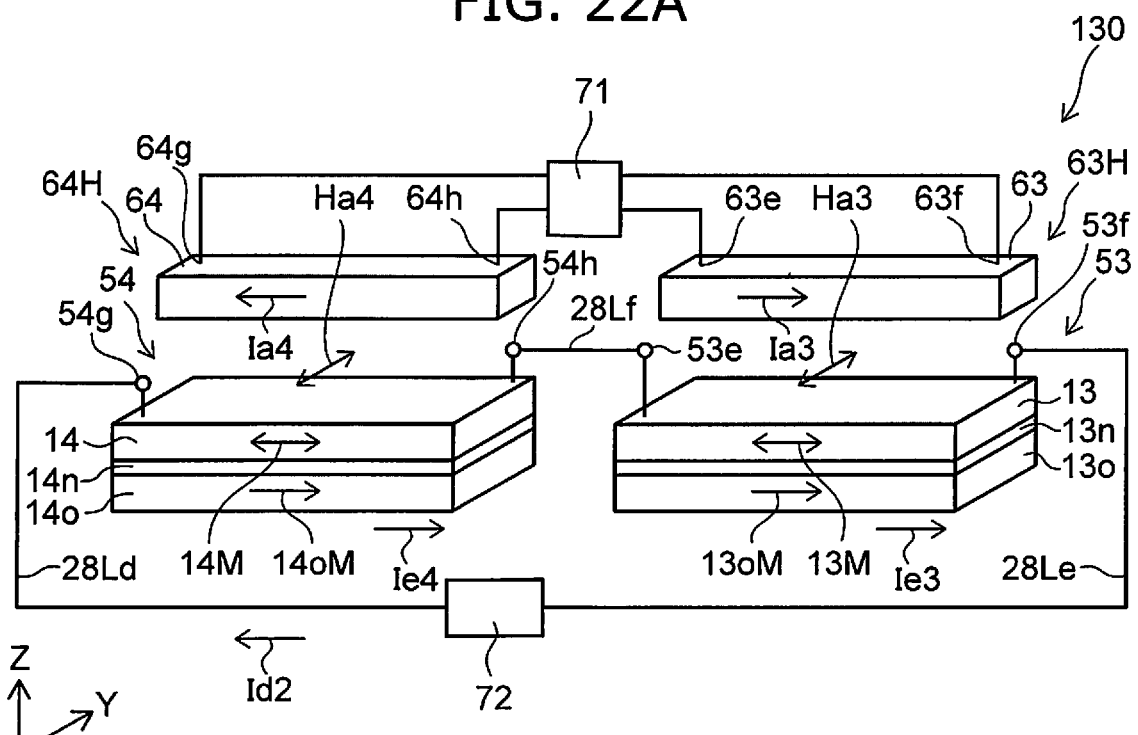
Figure 23A:
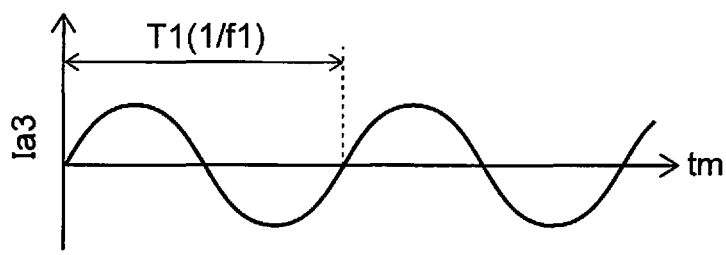
FIG. 23A to FIG. 23F are schematic views illustrating an operation of the magnetic sensor according to the second embodiment.
Figure 23B:
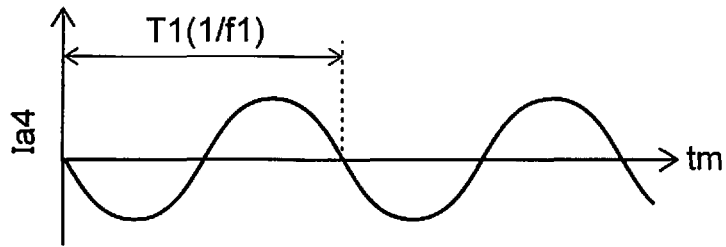
Figure 23C:
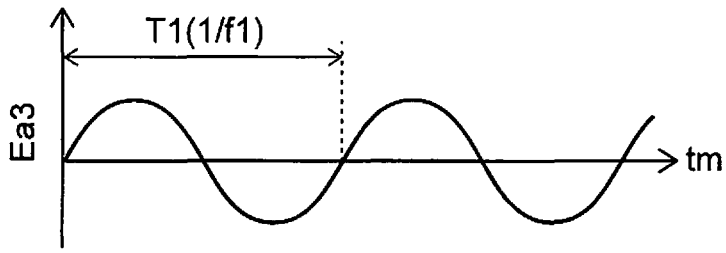
Figure 23D:
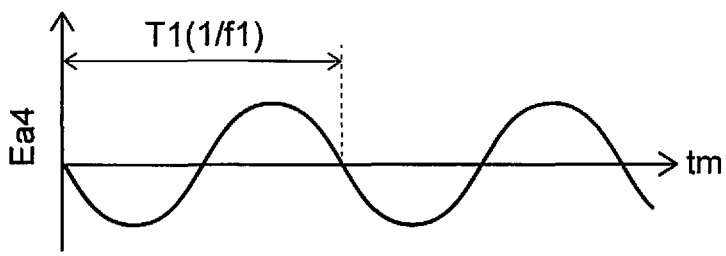
Figure 23E:
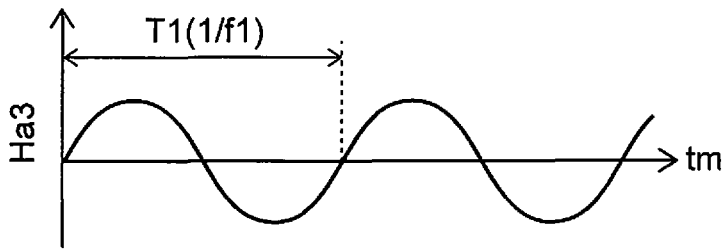
Figure 23F:
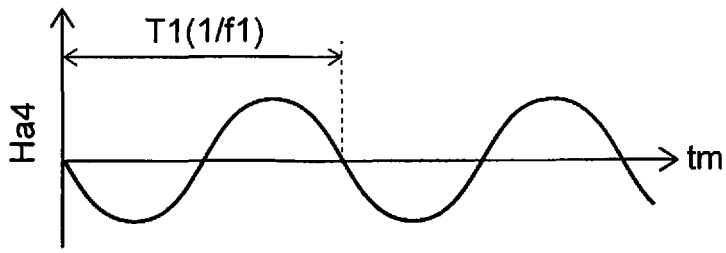

FIG. 22A and FIG. 22B are schematic perspective views illustrating the magnetic sensor.

FIG. 23A to FIG. 23F are schematic views illustrating an operation of the magnetic sensor according to the second embodiment.

As shown in FIG. 21, FIG. 22A, and FIG. 22B, the magnetic sensor 130 according to the embodiment includes the first to fourth elements 51 to 54, the first to fourth interconnects 61 to 64, and the first circuit portion 71. The second circuit portion 72 and the third circuit portion 73 are further provided in the example.

As shown in FIG. 22A, the first element 51 includes the first magnetic layer 11, the first opposing magnetic layer 11o, and the first nonmagnetic layer 11n provided between the first magnetic layer 11 and the first opposing magnetic layer 11o. The second element 52 includes the second magnetic layer 12, the second opposing magnetic layer 12o, and the second nonmagnetic layer 12n provided between the second magnetic layer 12 and the second opposing magnetic layer 12o.

As shown in FIG. 22B, the third element 53 includes the third magnetic layer 13, the third opposing magnetic layer 13o, and the third nonmagnetic layer 13n provided between the third magnetic layer 13 and the third opposing magnetic layer 13o. The fourth element 54 includes the fourth magnetic layer 14, the fourth opposing magnetic layer 14o, and the fourth nonmagnetic layer 14n provided between the fourth magnetic layer 14 and the fourth opposing magnetic layer 14o.

The first to fourth magnetic layers 11 to 14 have the first to fourth magnetic layer magnetizations 11M to 14M. The first to fourth opposing magnetic layers 11o to 14o have the first to fourth opposing magnetic layer magnetizations 11oM to 14oM. For example, the first to fourth magnetic layer magnetizations 11M to 14M move more easily than the first to fourth opposing magnetic layer magnetizations 11oM to 14oM.

For example, the electrical resistance of the third element 53 has an even-function characteristic with respect to the magnetic field applied to the third element 53. For example, the electrical resistance of the fourth element 54 has an even-function characteristic with respect to the magnetic field applied to the fourth element 54. As described above, for example, the electrical resistance of the first element 51 has an even-function characteristic with respect to the magnetic field applied to the first element 51. The electrical resistance of the second element 52 has an even-function characteristic with respect to the magnetic field applied to the second element 52.

The first circuit portion 71 is electrically connected to the first to fourth interconnects 61 to 64.

As shown in FIG. 21 and FIG. 22A, the distance between the first interconnect 61 and the first element 51 is shorter than the distance between the first interconnect 61 and the second element 52, shorter than the distance between the first interconnect 61 and the third element 53, and shorter than the distance between the first interconnect 61 and the fourth element 54.

The distance between the second interconnect 62 and the second element 52 is shorter than the distance between the second interconnect 62 and the first element 51, shorter than the distance between the second interconnect 62 and the third element 53, and shorter than the distance between the second interconnect 62 and the fourth element 54.

As shown in FIG. 21 and FIG. 22B, the distance between the third interconnect 63 and the third element 53 is shorter than the distance between the third interconnect 63 and the first element 51, shorter than the distance between the third interconnect 63 and the second element 52, and shorter than the distance between the third interconnect 63 and the fourth element 54.

The distance between the fourth interconnect 64 and the fourth element 54 is shorter than the distance between the fourth interconnect 64 and the first element 51, shorter than the distance between the fourth interconnect 64 and the second element 52, and shorter than the distance between the fourth interconnect 64 and the third element 53.

As shown in FIG. 22A, the first interconnect 61 includes the first interconnect end portion 61a and the second interconnect end portion 61b. The second interconnect 62 includes the third interconnect end portion 62c and the fourth interconnect end portion 62d. As shown in FIG. 22B, the third interconnect 63 includes a fifth interconnect end portion 63e and a sixth interconnect end portion 63f. The fourth interconnect 64 includes a seventh interconnect end portion 64g and an eighth interconnect end portion 64h.

As shown in FIG. 22A, the orientation from the third interconnect end portion 62c toward the fourth interconnect end portion 62d is aligned with the orientation from the first interconnect end portion 61a toward the second interconnect end portion 61b. As shown in FIG. 22B, the orientation from the seventh interconnect end portion 64g toward the eighth interconnect end portion 64h is aligned with the orientation from the fifth interconnect end portion 63e toward the sixth interconnect end portion 63f. As shown in FIG. 22A and FIG. 22B, the orientation from the seventh interconnect end portion 64g toward the eighth interconnect end portion 64h is aligned with the orientation from the first interconnect end portion 61a toward the second interconnect end portion 61b.

As shown in FIG. 22A, the first circuit portion 71 supplies the first alternating current Ia1 to the first interconnect 61. The first circuit portion 71 supplies the second alternating current Ia2 to the second interconnect 62. As shown in FIG. 22B, the first circuit portion 71 supplies a third alternating current Ia3 to the third interconnect 63. The first circuit portion 71 supplies a fourth alternating current Ia4 to the fourth interconnect 64.

At the first time (any one time), the first alternating current Ia1 has the orientation from the first interconnect end portion 61a toward the second interconnect end portion 61b. At the first time, the second alternating current Ia2 has the orientation from the fourth interconnect end portion 62d toward the third interconnect end portion 62c. At the first time, the third alternating current Ia3 has the orientation from the fifth interconnect end portion 63e toward the sixth interconnect end portion 63f. At the first time, the fourth alternating current Ia4 has the orientation from the eighth interconnect end portion 64h toward the seventh interconnect end portion 64g.

The first to fourth interconnects 61 to 64 are examples of the first to fourth magnetic field generators 61H to 64H. For example, the first to fourth AC magnetic fields Ha1 to Ha4 are generated from the first to fourth magnetic field generators 61H to 64H (the first to fourth interconnects 61 to 64).

The first alternating current Ia1, the second alternating current Ia2, the first potential Ea1 of the end portion of the first interconnect 61, the second potential Ea2 of the end portion of the second interconnect 62, the first AC magnetic field Ha1, and the second AC magnetic field Ha2 have the characteristics described in reference to FIG. 2A to FIG. 2F.

The third alternating current Ia3, the fourth alternating current Ia4, a third electric potential Ea3 of the end portion of the third interconnect 63, a fourth electric potential Ea4 of the end portion of the fourth interconnect 64, the third AC magnetic field Ha3, and the fourth AC magnetic field Ha4 have the characteristics illustrated in FIG. 23A to FIG. 23F.

The first alternating current Ia1 and the second alternating current Ia2 have opposite phase to each other (referring to FIG. 2A and FIG. 2B). The third alternating current Ia3 and the fourth alternating current Ia4 have opposite phase to each other (referring to FIG. 23A and FIG. 23B). The first alternating current Ia1 and the third alternating current Ia3 have the same phase. The second alternating current Ia2 and the fourth alternating current Ia4 have the same phase.

The first electric potential Ea1 and the second electric potential Ea2 have opposite phases to each other (referring to FIG. 2C and FIG. 2D). The third electric potential Ea3 and the fourth electric potential Ea4 have opposite phases to each other (referring to FIG. 23C and FIG. 23D). The first electric potential Ea1 and the third electric potential Ea3 have the same phase. The second electric potential Ea2 and the fourth electric potential Ea4 have the same phase.

The first AC magnetic field Ha1 and the second AC magnetic field Ha2 have opposite phases to each other (referring to FIG. 2E and FIG. 2F). The third AC magnetic field Ha3 and the fourth AC magnetic field Ha4 have opposite phases to each other (referring to FIG. 23E and FIG. 23F). The first AC magnetic field Ha1 and the third AC magnetic field Ha3 have the same phase. The second AC magnetic field Ha2 and the fourth AC magnetic field Ha4 have the same phase.

The first to fourth alternating currents Ia1 to Ia4 have the first frequency f1. The first to fourth AC magnetic fields Ha1 to Ha4 have the first frequency f1.

Thus, the first circuit portion 71 supplies the first to fourth alternating currents Ia1 to Ia4 respectively to the first to fourth interconnects 61 to 64. The second circuit portion 72 supplies the first to fourth element currents Ie1 to Ie4 respectively to the first to fourth elements 51 to 54 (referring to FIG. 21, FIG. 22A, and FIG. 22B).

At the first time, the first to fourth alternating currents Ia1 to Ia4 respectively have the first to fourth alternating current orientations (the orientations illustrated in FIG. 21, FIG. 22A, and FIG. 22B). At the second time, the first to fourth alternating currents Ia1 to Ia4 respectively have the opposite orientations of the first to fourth alternating current orientations recited above. The second time is a time at which the polarities of the alternating currents are reversed with respect to those of the first time.

At the first time, the first to fourth element currents Ie1 to Ie4 have the first to fourth element current-alternating current orientations (the orientations illustrated in FIG. 21, FIG. 22A, and FIG. 22B). At the second time as well, the first to fourth element currents Ie1 to Ie4 have the same first to fourth element current-alternating current orientations recited above.

As shown in FIG. 22A, the first alternating current orientation has a component in the orientation of the first element current Ie1. The second alternating current orientation has a component in the reverse orientation of the orientation of the second element current Ie2. As shown in FIG. 22B, a third alternating current orientation has a component in the orientation of the third element current Ie3. A fourth alternating current orientation has a component in the opposite orientation to the orientation of the fourth element current Ie4.

The first to fourth elements 51 to 54 form a bridge. By using alternating currents (AC magnetic fields) such as those recited above, a component of the double frequency 2f1 can be suppressed in the signals obtained from the first to fourth elements 51 to 54. The detection of the component of the first frequency f1 is easy. The magnetic field Hm from the detection object can be detected with high precision. In the embodiment as well, the detection sensitivity can be increased.

For example, as shown in FIG. 21, FIG. 22A, and FIG. 22B, the first element 51 and the second element 52 are electrically connected in series. The fourth element 54 and the third element 53 are electrically connected in series. The first element 51 and the second element 52 are electrically connected by the interconnect 28Lc. The third element 53 and the fourth element 54 are electrically connected by an interconnect 28Lf.

The second circuit portion 72 is electrically connected to the first element 51 and the second element 52. For example, the connections are performed by the interconnect 28La and the interconnect 28Lb. The second circuit portion 72 is electrically connected to the third element 53 and the fourth element 54. For example, the connections are performed by an interconnect 28Ld and an interconnect 28Le.

As shown in FIG. 22A, the second circuit portion 72 supplies the first current Id1 to the first element 51 and the second element 52. The first current Id1 has at least a direct current component. As shown in FIG. 22B, the second circuit portion 72 supplies the second current Id2. The second current Id2 has at least a direct current component.

In the example, the first element 51 includes the first element end portion 51a and the second element end portion 51b. The second element 52 includes the third element end portion 52c and the fourth element end portion 52d. The third element 53 includes a fifth element end portion 53e and a sixth element end portion 53f. The fourth element 54 includes a seventh element end portion 54g and an eighth element end portion 54h.

As shown in FIG. 21, for example, the first element end portion 51a and the seventh element end portion 54g are electrically connected to each other. The fourth element end portion 52d and the sixth element end portion 53f are electrically connected to each other. The second element end portion 51b and the third element end portion 52c are electrically connected to each other. The eighth element end portion 54h and the fifth element end portion 53e are electrically connected to each other.

The second circuit portion 72 is electrically connected to the first element end portion 51a, the seventh element end portion 54g, the fourth element end portion 52d, and the sixth element end portion 53f.

As shown in FIG. 22A, the second circuit portion 72 supplies, to a set of the first element 51 and the second element 52, the first current Id1 having at least a direct current component. As shown in FIG. 22B, the second circuit portion 72 supplies, to a set of the fourth element 54 and the third element 53, the second current Id2 having at least a direct current component.

By such currents, signals are generated at the connection point of the set of the first element 51 and the second element 52 and the connection point of the set of the fourth element 54 and the third element 53. These signals have components of the first frequency f1.

As shown in FIG. 21, for example, the third circuit portion 73 outputs a signal corresponding to the difference in the electric potential between the second element end portion 51b and the eighth element end portion 54h. For example, this signal corresponds to a component of the difference between the electric potential of the second element end portion 51b and the electric potential of the eighth element end portion 54h having the first frequency f1. The third circuit portion 73 includes, for example, a differential circuit.

In the example, the third circuit portion 73 includes the differential circuit portion 73A and the filter 73B. The differential circuit portion 73A includes the first input terminal 73Aa, the second input terminal 73Ab, and the differential circuit portion output terminal 73Ac. The first input terminal 73Aa is electrically connected to the second element end portion 51b. The second input terminal 73Ab is electrically connected to the eighth element end portion 54h.

The differential circuit portion output terminal 73Ac outputs a signal SigC corresponding to the difference between the electric potential of the first input terminal 73Aa and the potential of the second input terminal 73Ab.

The input terminal 73Bi of the filter 73B is electrically connected to the differential circuit portion output terminal 73Ac. The filter 73B outputs the signal Sig0 corresponding to a frequency component of a portion of the signal SigC of the differential circuit portion output terminal 73Ac (e.g., a component of the first frequency f1).

An example of simulation results relating to the magnetic sensors will now be described.

Figure 24:
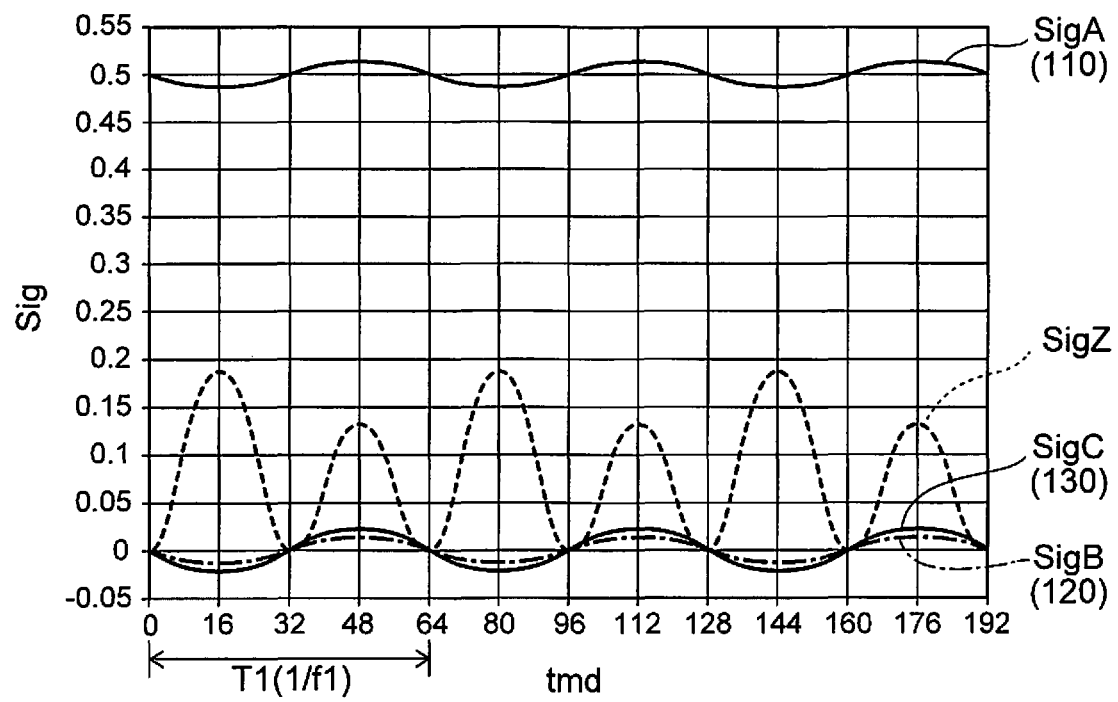
FIG. 24 is a graph illustrating characteristics of the magnetic sensor.

FIG. 24 is a graph illustrating characteristics of the magnetic sensor.

FIG. 24 illustrates simulation results of characteristics of the magnetic sensors 110, 120, and 130 recited above. The horizontal axis of FIG. 24 is the time tmd. The time period in which the time tm is 0 to 64 corresponds to a period T1 (1/f1). The vertical axis of FIG. 24 is the signal Sig obtained from the magnetic sensor 120. The signal SigZ that corresponds to the potential of the first element end portion 51a of the first element 51 (referring to FIG. 21) is illustrated in FIG. 24. The signal SigZ corresponds to the change of the voltage between the two ends of an element. The signal SigA (referring to FIG. 1A), the signal SigB (referring to FIG. 9), and the signal SigC (referring to FIG. 21) are illustrated in FIG. 24.

As shown in FIG. 24, the signal SigZ has a component of the first frequency f1 and a component of the double frequency 2f1. Conversely, for the signals SigA, SigB, and SigC, the double frequency 2f1 is not observed; and components of the first frequency f1 are observed. The signal SigA has a DC component in addition to the component of the first frequency f1. A DC component is substantially not generated in the signals SigB and SigC. This is due to the bridge configuration. The amplitude of the signal SigC is larger than the amplitude of the signal SigB. By using the signal SigC, higher sensitivity is obtained easily.

Figure 25A:
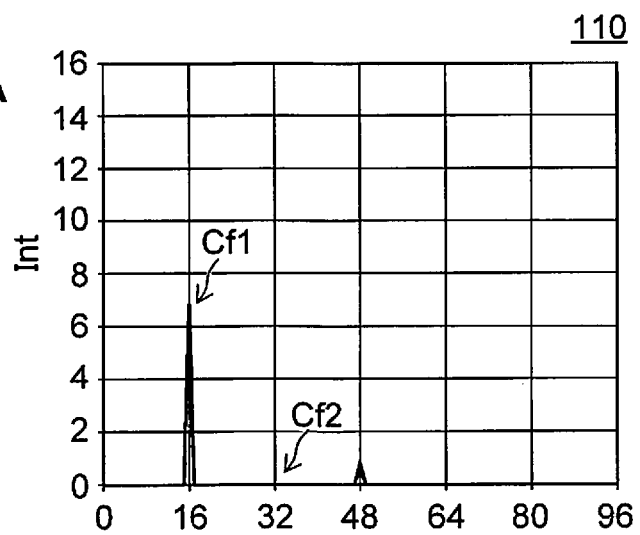
FIG. 25A to FIG. 25C are graphs illustrating characteristics of the magnetic sensor.
Figure 25B:
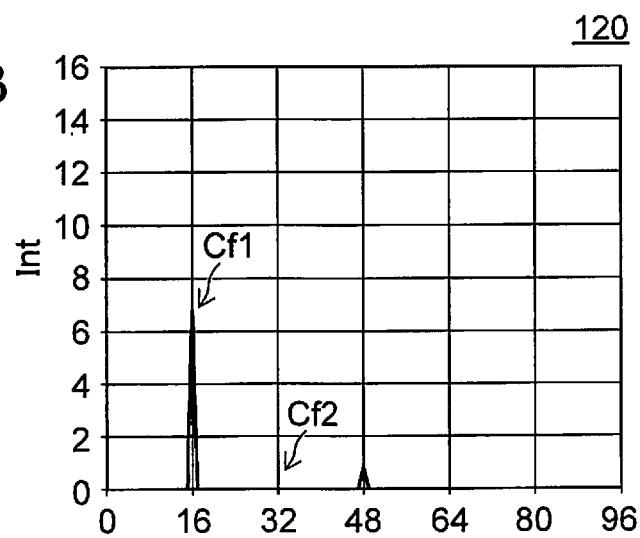
Figure 25C:
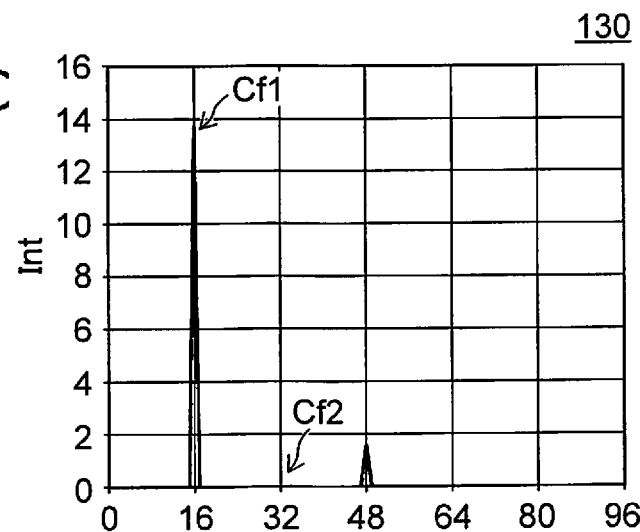

FIG. 25A to FIG. 25C are graphs illustrating characteristics of the magnetic sensor.

These figures illustrate results of the FFT analysis of the signals SigA to SigC illustrated in FIG. 24. In these figures, the horizontal axis corresponds to the frequency of the signals. In these figures, the vertical axis corresponds to the intensity of each frequency components. For the signals SigA to SigC, the component Cf2 of the double frequency 2f1 is not observed; and the component Cf1 of the first frequency f1 is observed. The magnitude of the component Cf1 of the signal SigC is larger than the magnitude of the component Cf1 of the signal SigB. A larger output is obtained by the configuration of the magnetic sensor 130.

Examples of distortions of the output signals for the magnetic sensors 120 and 130 when the characteristics of the multiple elements or the characteristics of the AC magnetic fields fluctuate will now be described. For example, the magneto-resistance ratio may fluctuate when the sizes of the multiple elements, etc., fluctuate. For example, the phases of the AC magnetic fields may shift due to fluctuation in the widths of the interconnects, the distances from the circuit portions to the interconnects, etc.

Figure 26A:
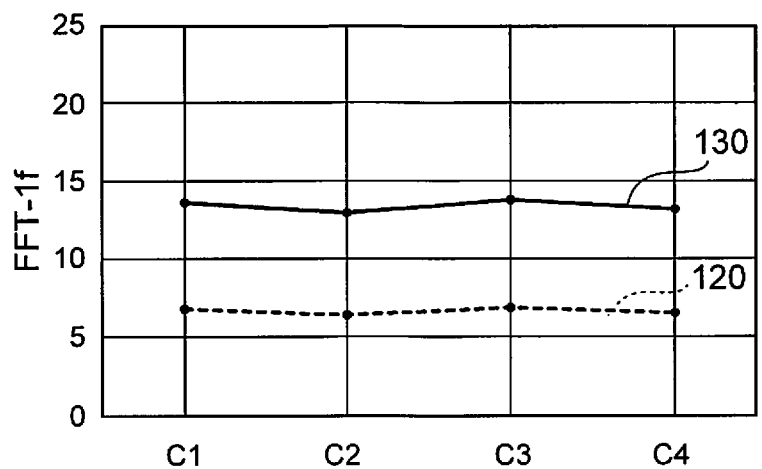
FIG. 26A and FIG. 26B are graphs illustrating the characteristics of the magnetic sensors.
Figure 26B:
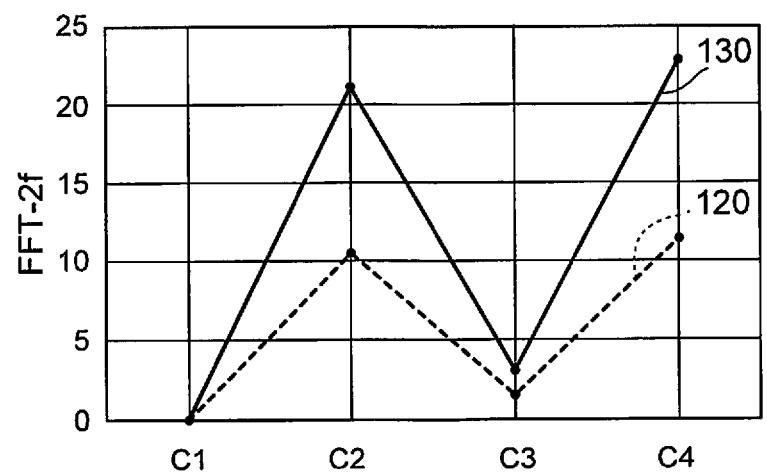

FIG. 26A and FIG. 26B are graphs illustrating the characteristics of the magnetic sensors.

These figures illustrate the characteristics of the magnetic sensors 120 and 130. Simulation results of the characteristics for first to fourth conditions C1 to C4 are illustrated in these figures. For the first condition C1, the magneto-resistance ratios (the amplitudes) of the first element 51, the second element 52, the third element 53, and the fourth element 54 are the same; and the phases of the first AC magnetic field Ha1, the second AC magnetic field Ha2, the third AC magnetic field Ha3, and the fourth AC magnetic field Ha4 match each other. For the second condition C2, the magneto-resistance ratios (the amplitudes) of the first element 51, the second element 52, the third element 53, and the fourth element 54 are the same; and the phases of the first AC magnetic field Ha1 and the third AC magnetic field Ha3 are shifted 10% with respect to the phases of the second AC magnetic field Ha2 and the fourth AC magnetic field Ha4. For the third condition C3, the magneto-resistance ratios (the amplitudes) of the first element 51 and the third element 53 are 10% different from the magneto-resistance ratios (the amplitudes) of the second element 52 and the fourth element 54; and the phases of the first AC magnetic field Ha1, the second AC magnetic field Ha2, the third AC magnetic field Ha3, and the fourth AC magnetic field Ha4 match each other. For the fourth condition C4, the magneto-resistance ratios (the amplitudes) of the first element 51 and the third element 53 are 10% different from the magneto-resistance ratios (the amplitudes) of the second element 52 and the fourth element 54; and the phases of the first AC magnetic field Ha1 and the third AC magnetic field Ha3 are shifted 10% with respect to the phases of the second AC magnetic field Ha2 and the fourth AC magnetic field Ha4.

In these figures, the horizontal axis corresponds to the first to fourth conditions C1 to C4 recited above. The vertical axis of FIG. 26A is a strength FFT-1$f$ of the component of the signal with the first frequency f1 obtained by the FFT analysis. The vertical axis of FIG. 26B is a strength FFT-2$f$ of the component of the signal with the double frequency 2f1 obtained by the FFT analysis.

In the magnetic sensors 120 and 130 as shown in FIG. 26A, the FFT-1$f$ does not change even in the case where the conditions change as in the first to fourth conditions C1 to C4.

In the magnetic sensors 120 and 130 as shown in FIG. 26B, the FFT-2$f$ changes greatly when the conditions change such as in the second condition C2 and the fourth condition C4. Thus, the component of the double frequency 2f1 increases as the shift of the phases of the AC magnetic fields increases. Conversely, as in the third condition C3, the component of the double frequency 2f1 is maintained to be low even when the magneto-resistance ratios (the amplitudes) of the multiple elements fluctuate. Compared to the magnetic sensor 130, the effects when the magneto-resistance ratios (the amplitudes) of the multiple elements fluctuate are small for the magnetic sensor 120. The magnetic sensor 120 or 130 may be selectively used according to the purpose of use.

The first magnetic portion 51F and the second magnetic portion 52F (referring to FIG. 15A, FIG. 15B, FIG. 16A, FIG. 16B, etc.) may be provided in the second embodiment. The magnetic portions described below may be further provided.

FIG. 27A, FIG. 27B, FIG. 28A, and FIG. 28B are schematic views illustrating portions of a magnetic sensor according to the second embodiment.

Figure 27A:
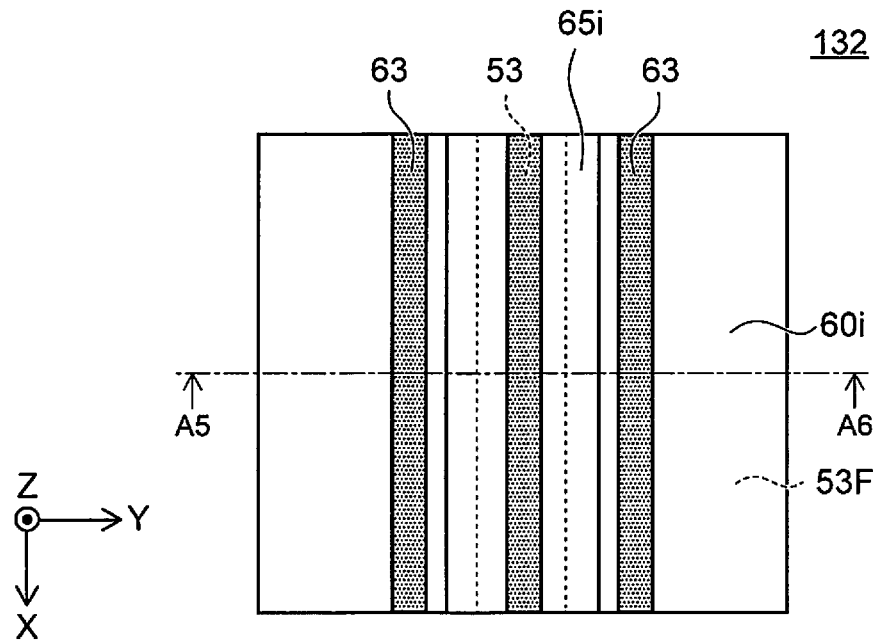
FIG. 27A and FIG. 27B are schematic views illustrating portions of a magnetic sensor according to the second embodiment.
Figure 27B:
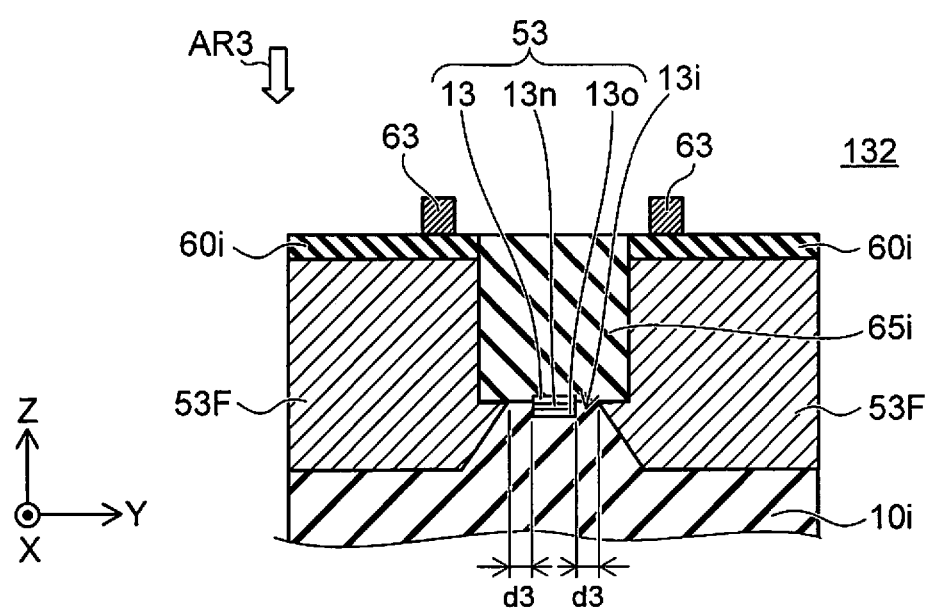
Figure 28A:
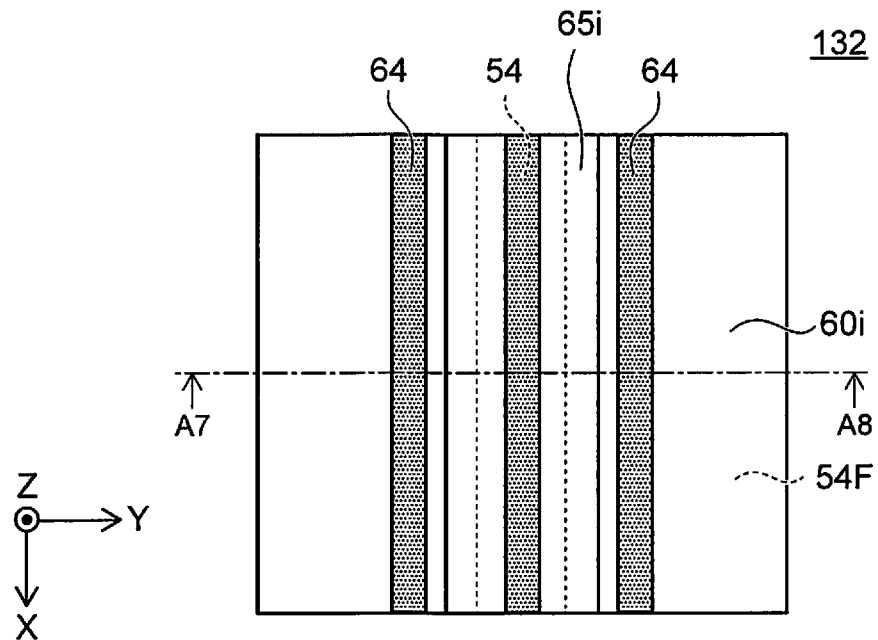
FIG. 28A and FIG. 28B are schematic views illustrating portions of the magnetic sensor according to the second embodiment.
Figure 28B:
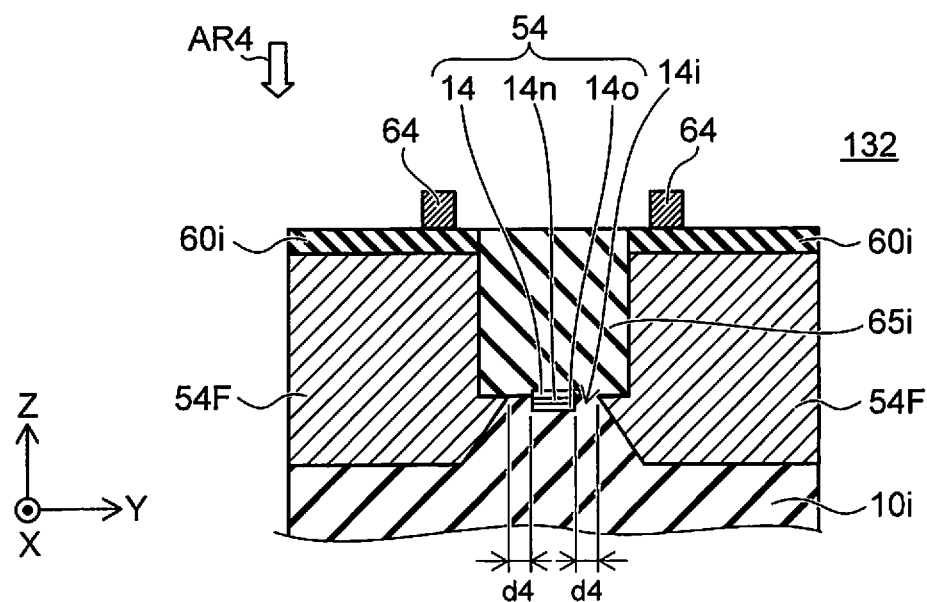
Figure 29A:
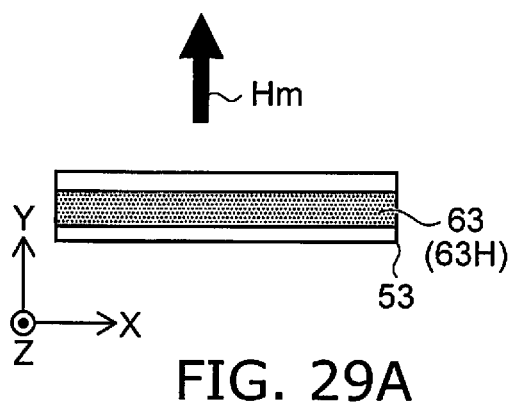
FIG. 29A to FIG. 29D are schematic views illustrating a portion of the magnetic sensor according to the second embodiment.
Figure 29B:
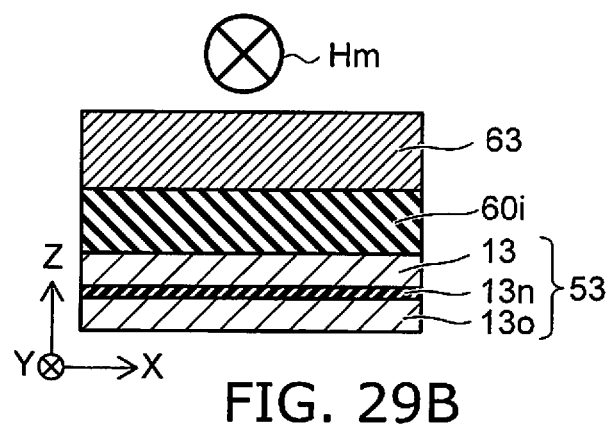
Figure 29C:
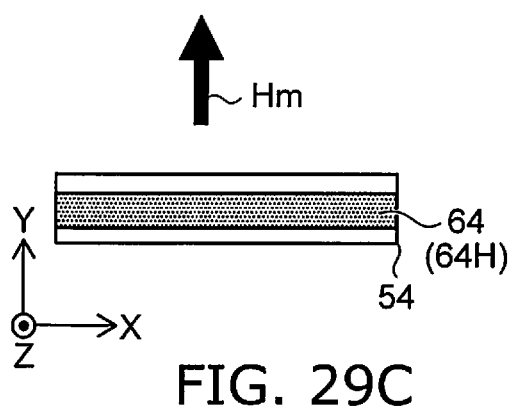
Figure 29D:
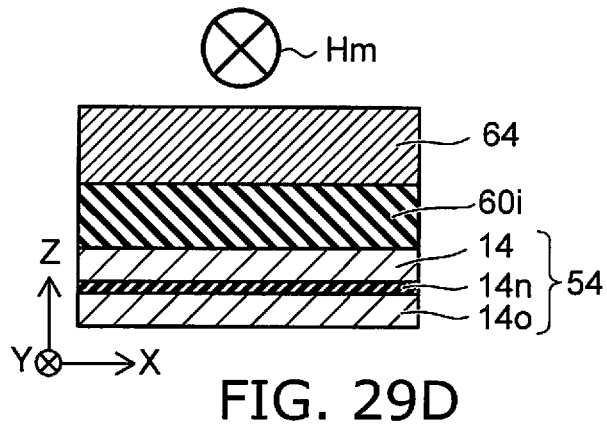

FIG. 27A is a plan view as viewed along arrow AR3 of FIG. 27B. FIG. 27B is a line A5-A6 cross-sectional view of FIG. 27A. FIG. 28A is a plan view as viewed along arrow AR4 of FIG. 28B. FIG. 28B is a line A7-A8 cross-sectional view of FIG. 28A.

As shown in these figures, a third magnetic portion 53F, a third nonmagnetic region 13$i$, a fourth magnetic portion 54F, and a fourth nonmagnetic region 14$i$ are provided in the magnetic sensor 132 according to the embodiment.

As shown in FIG. 27B, the third nonmagnetic region 13$i$ is provided between the third magnetic portion 53F and the third element 53. The thickness (a distance d3) of the third nonmagnetic region 13$i$ along the direction from the third element 53 toward the third magnetic portion 53F is, for example, 10 nm or less.

As shown in FIG. 28B, the fourth nonmagnetic region 14$i$ is provided between the fourth magnetic portion 54F and the fourth element 54. The thickness (a distance d4) of the fourth nonmagnetic region 14$i$ along the direction from the fourth element 54 toward the fourth magnetic portion 54F is, for example, 10 nm or less.

The third magnetic portion 53F and the fourth magnetic portion 54F include, for example, materials similar to the materials of the first magnetic portion 51F and the second magnetic portion 52F. For example, the third magnetic portion 53F and the fourth magnetic portion 54F function as MFCs. By providing the third magnetic portion 53F and the fourth magnetic portion 54F, for example, the AC magnetic fields and the magnetic field Hm from the detection object concentrate efficiently in the third element 53 and the fourth element 54.

The thicknesses in the Z-axis direction of the third magnetic portion 53F and the fourth magnetic portion 54F are thicker than the thicknesses in the Z-axis direction of the third element 53 and the fourth element 54. Thereby, for example, the magnetic field concentration effect is obtained effectively.

FIG. 29A to FIG. 29D are schematic views illustrating a portion of the magnetic sensor according to the second embodiment.

The insulating layer 60$i$ may be provided between the third element 53 and the third interconnect 63. The insulating layer 60$i$ may be provided between the fourth element 54 and the fourth interconnect 64. For example, the magnetic field Hm along the Y-axis direction is applied to these elements. The AC magnetic fields that are generated from the third interconnect 63 (the third magnetic field generator 63H) and the fourth interconnect 64 (the fourth magnetic field generator 64H) have components along the direction of the magnetic field Hm.

Figure 30A:
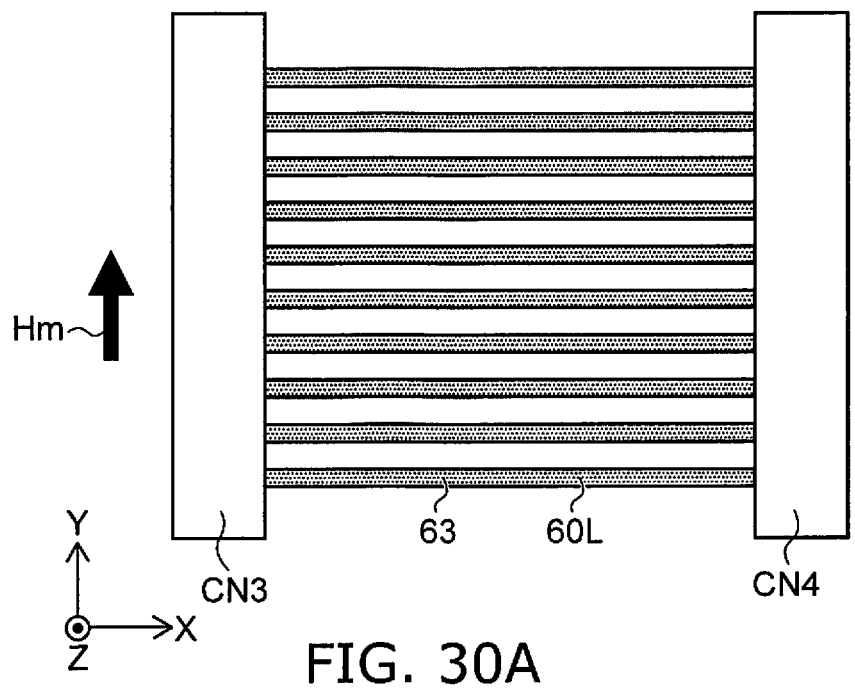
FIG. 30A and FIG. 30B are schematic views illustrating a portion of the magnetic sensor according to the second embodiment.
Figure 30B:
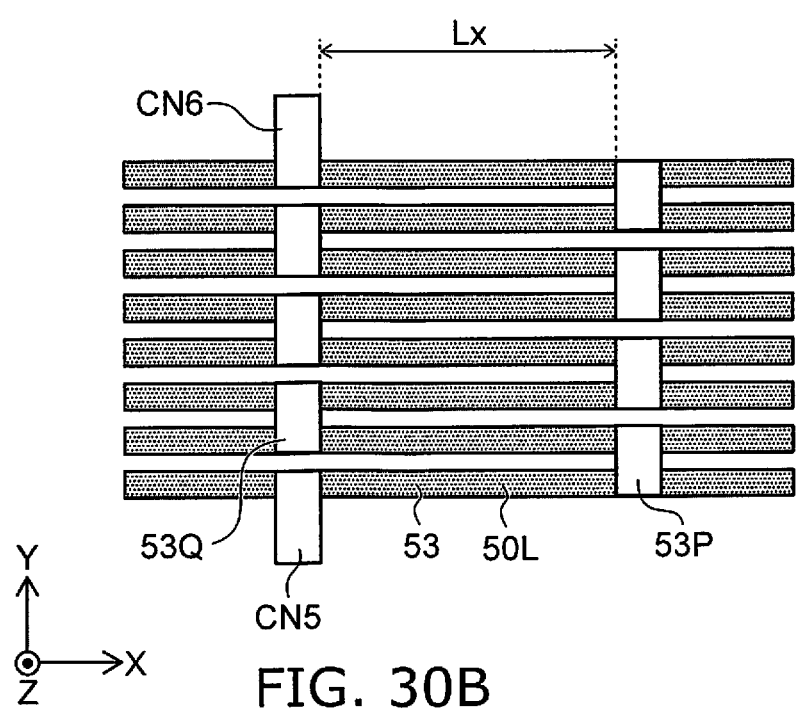

FIG. 30A and FIG. 30B are schematic views illustrating a portion of the magnetic sensor according to the second embodiment.

These figures illustrate the layout of the third interconnects 63 and the third elements 53. For easier viewing in these figures, the interconnects and the elements are illustrated separately. The structure illustrated in FIG. 30A and the structure illustrated in FIG. 30B overlap in the Z-axis direction.

As shown in FIG. 30A, the conductive portions 60L that have multiple band configurations extending along the X-axis direction are provided. One of the conductive portions 60L having the multiple band configurations corresponds to at least a portion of the third interconnect 63.

As shown in FIG. 30B, the structure bodies 50L that have multiple band configurations extending along the X-axis direction are provided. One of the structure bodies 50L having the multiple band configurations corresponds to at least a portion of the third element 53. In the example, an end of one of the structure bodies 50L having the multiple band configurations is electrically connected by a connection member 53P to an end of another one of the structure bodies 50L having the multiple band configurations. Another end of the other one of the structure bodies 50L having the multiple band configurations recited above is electrically connected by a connection member 53Q to an end of yet another one of the structure bodies 50L having the multiple band configurations. The multiple third elements 53 and the multiple fourth elements 54 are arranged alternately in the Y-axis direction. These elements are connected in series in a folded zigzag configuration.

For example, the connecting conductive portion CN6 (the terminal) is electrically connected to one end of the third elements 53. The connecting conductive portion CN5 (the terminal) is electrically connected to another end of the third elements 53. For example, a current is supplied between these terminals. For example, the current is supplied by the second circuit portion 72.

Figure 31:
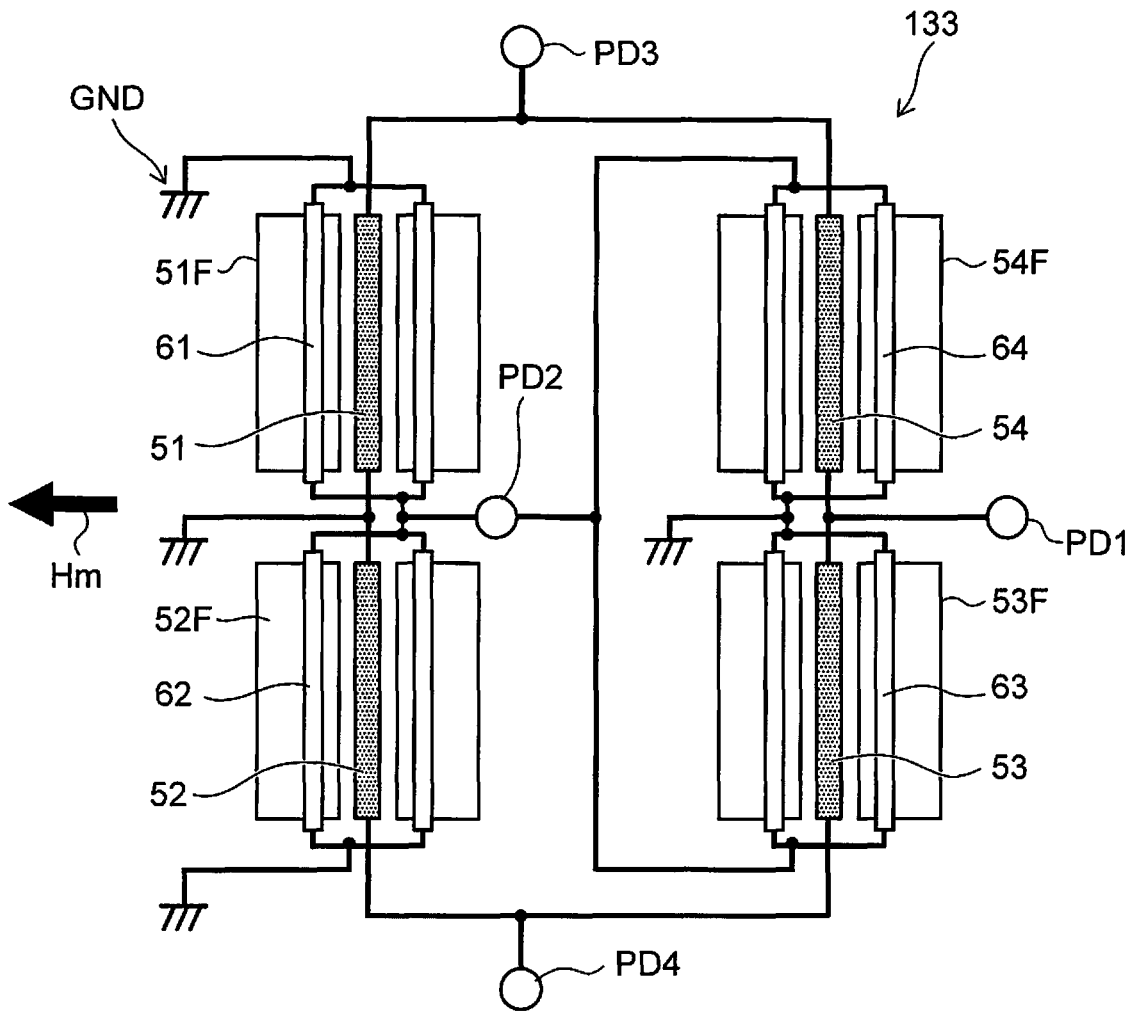
FIG. 31 is a schematic view illustrating a portion of a magnetic sensor according to the second embodiment.

FIG. 31 is a schematic view illustrating a portion of a magnetic sensor according to the second embodiment.

As shown in FIG. 31, the first interconnects 61, the second interconnects 62, the third interconnects 63, the fourth interconnects 64, the first element 51, the second element 52, the third element 53, and the fourth element 54 are provided in the magnetic sensor 133 according to the embodiment. The first to fourth pads PD1 to PD4 are provided in the example.

The first interconnects 61 are electrically connected to the second pad PD2 at one end portion. The first interconnects 61 are electrically connected to ground (the ground GND) at another end portion. The second interconnects 62 are electrically connected to the second pad PD2 at one end portion. The second interconnects 62 are electrically connected to ground (the ground GND) at another end portion. The one end portions of the first interconnects 61 recited above and the one end portions of the second interconnects 62 recited above are provided between the other end portions of the first interconnects 61 recited above and the other end portions of the second interconnects 62 recited above.

The third interconnects 63 are electrically connected to the second pad PD2 at one end portion. The third interconnects 63 are electrically connected to ground (the ground GND) at another end portion. The fourth interconnects 64 are electrically connected to the second pad PD2 at one end portion. The fourth interconnects 64 are electrically connected to ground (the ground GND) at another end portion. The other end portions of the third interconnects 63 recited above and the other end portions of the fourth interconnects 64 recited above are provided between the one end portions of the third interconnects 63 recited above and the one end portions of the fourth interconnects 64 recited above.

One end portion of the first element 51 is electrically connected to the third pad PD3. Another end portion of the first element 51 is electrically connected to ground (the ground GND). One end portion of the second element 52 is electrically connected to the fourth pad PD4. Another end portion of the second element 52 is electrically connected to ground (the ground GND). The other end portion of the first element 51 recited above and the other end portion of the second element 52 recited above are provided between the one end portion of the first element 51 recited above and the one end portion of the second element 52 recited above.

One end portion of the third element 53 is electrically connected to the fourth pad PD4. Another end portion of the third element 53 is electrically connected to the first pad PD1. One end portion of the fourth element 54 is electrically connected to the third pad PD3. Another end portion of the fourth element 54 is electrically connected to the first pad PD1. The other end portion of the third element 53 recited above and the other end portion of the fourth element 54 recited above are provided between the one end portion of the third element 53 recited above and the one end portion of the fourth element 54 recited above.

For example, the second pad PD2 is electrically connected to the first circuit portion 71. An alternating current is supplied to the second pad PD2. This alternating current becomes the first to fourth alternating currents Ia1 to Ia4 in the first to fourth interconnects 61 to 64.

One bridge is formed of the first to fourth elements 51 to 54. The first pad PD1 is electrically connected to the second circuit portion 72. A current is supplied to the first pad PD1. The current becomes the first current Id1 in the first and second elements 51 and 52. The current becomes the second current Id2 in the third element 53 and the fourth element 54.

The third pad PD3 and the fourth pad PD4 are electrically connected to the third circuit portion 73. The third pad PD3 and the fourth pad PD4 correspond to midpoints of the bridge. A signal is detected by the third circuit portion 73. The component of the double frequency 2f1 is suppressed in this signal. The signal has a component of the first frequency f1.

First to fourth magnetic portions 51F to 54F are provided in the magnetic sensor 133.

Figures 32A, 32B:
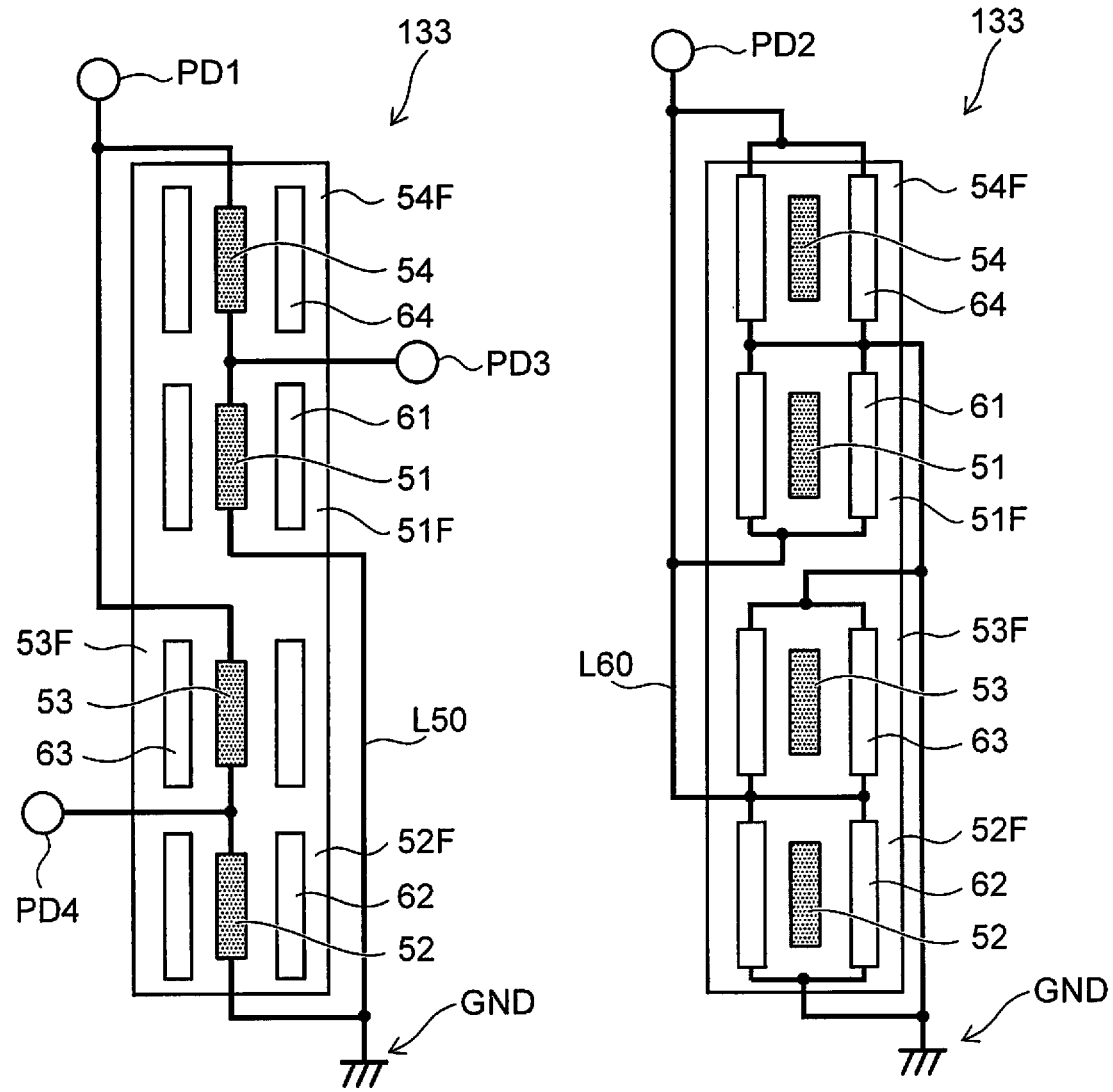
FIG. 32A and FIG. 32B are schematic views illustrating a portion of the magnetic sensor according to the second embodiment.

FIG. 32A and FIG. 32B are schematic views illustrating a portion of the magnetic sensor according to the second embodiment.

These figures illustrate the layout of the interconnects of the magnetic sensor 133 according to the embodiment. FIG. 32B illustrates the interconnect L60 electrically connected to the first to fourth interconnects 61 to 64. FIG. 32A illustrates the interconnect L50 electrically connected to the first to fourth elements 51 to 54. For easier viewing in these figures, the structures shown in FIG. 32A and FIG. 32B are illustrated separately. In the actual magnetic sensor 133, the structures shown in FIG. 32A and FIG. 32B overlap in the Z-axis direction. In the layout, the structures of the first to fourth magnetic portions 51F to 54F are shared as a continuous magnetic body. By using such a structure, the pattern configuration is simple; and it is easy to make the elements.

Figure 33A:
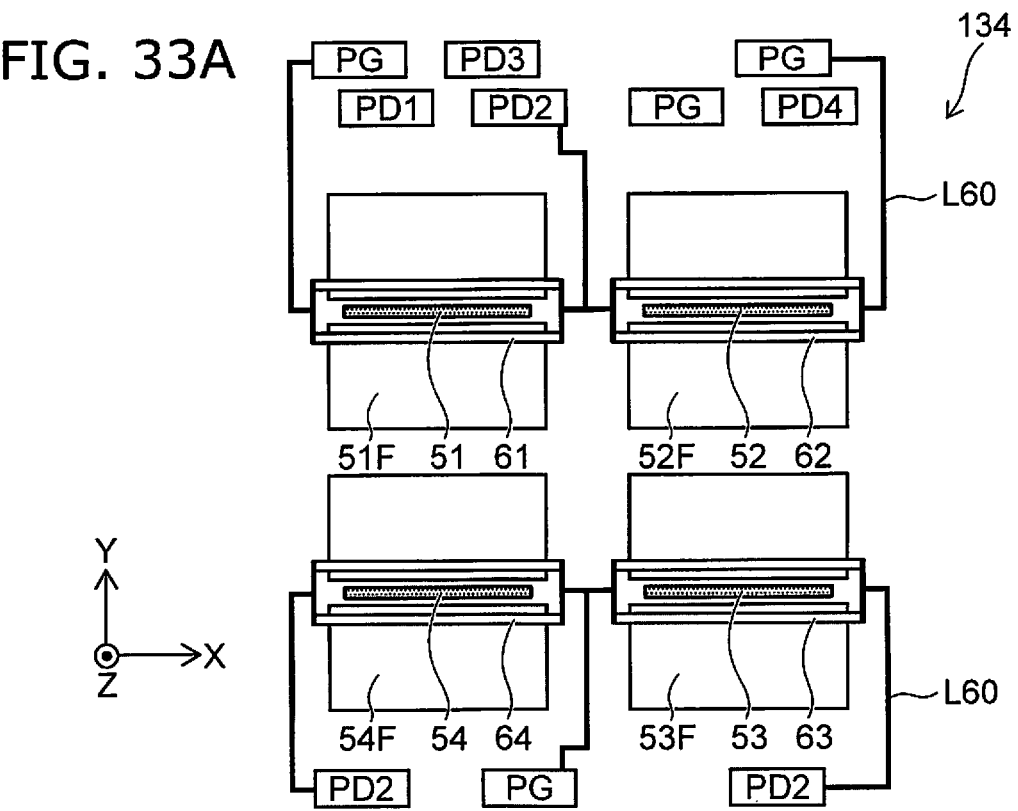
FIG. 33A and FIG. 33B are schematic views illustrating a portion of a magnetic sensor according to the second embodiment.
Figure 33B:
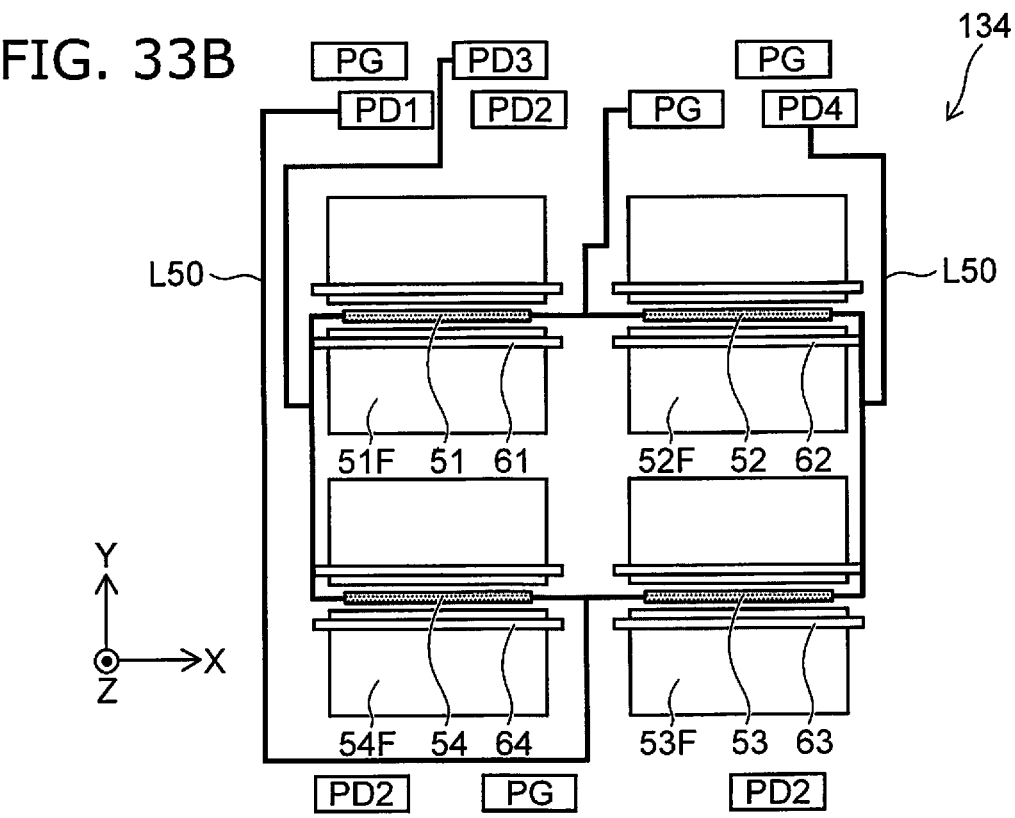

FIG. 33A and FIG. 33B are schematic views illustrating a portion of a magnetic sensor according to the second embodiment.

These figures illustrate the layout of the interconnects of the magnetic sensor 134 according to the embodiment. FIG. 33A illustrates the interconnect L60 electrically connected to the first to fourth interconnects 61 to 64. FIG. 33B illustrates the interconnect L50 electrically connected to the first to fourth elements 51 to 54. For easier viewing in these figures, the structures shown in FIG. 33A and FIG. 33B are illustrated separately. In the actual magnetic sensor 134, the structures shown in FIG. 33A and FIG. 33B overlap in the Z-axis direction.

In the first and second embodiments recited above, the first current Id1 and the second current Id2 may have alternating current components in addition to the direct current components.

Figure 34:
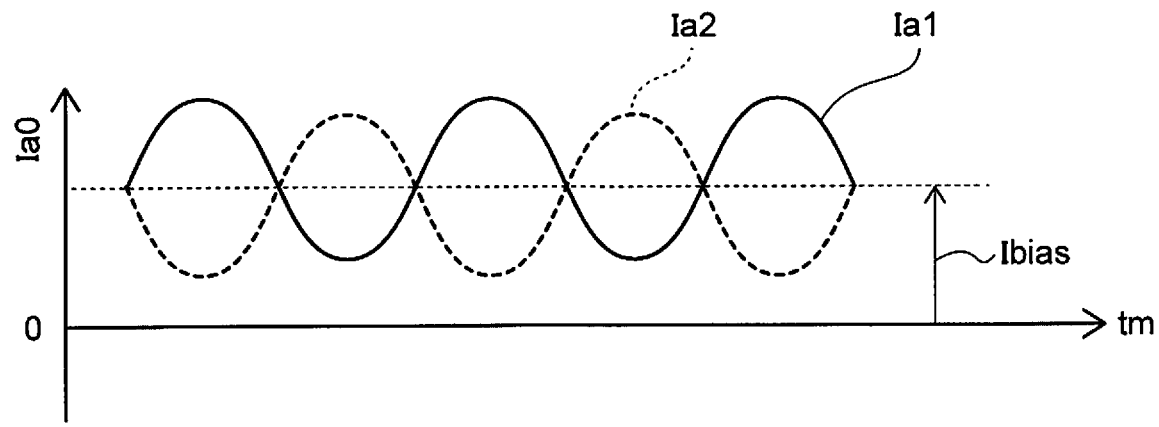
FIG. 34 is a schematic view illustrating an operation of the magnetic sensor according to the embodiment.

FIG. 34 is a schematic view illustrating an operation of the magnetic sensor according to the embodiment.

FIG. 34 illustrates the first alternating current Ia1 and the second alternating current Ia2. The horizontal axis of FIG. 34 is the time tm. The vertical axis is a current Ia0. As shown in FIG. 34, the first alternating current Ia1 and the second alternating current Ia2 may have a bias component Ibias in addition to the alternating current components.

For example, the bias component Ibias is set to suppress external magnetic fields, etc. In one example, the external magnetic field is, for example, geomagnetism or the like. As described below, the external magnetic field may have an alternating current component. For example, a direct-current (DC) magnetic field that substantially cancels geomagnetism is superimposed onto the AC magnetic fields applied to the elements. Thereby, for example, the influence of geomagnetism can be suppressed. In the case where the external magnetic field has an AC component, the bias component Ibias may change with time.

For example, in the case where the bias component Ibias is provided in the magnetic sensor 120 illustrated in FIG. 9, a positive bias may be superimposed onto one of the two first circuit portions 71; and, for example, a negative bias may be superimposed onto the other of the two first circuit portions 71.

The bias component Ibias may be applied to any magnetic sensor according to the first and second embodiments and any modification of the magnetic sensors.

For example, the current (or the voltage) that is output from the first circuit portion 71 may include a bias component Ibias such as that recited above. The first circuit portion 71 may be combined with another circuit portion; and the bias component Ibias may be superimposed by the other circuit portion. For example, the circuit can be simplified by sharing an external alternating current power supply and by forming reverse phases by a contrivance of the circuit.

An example of measurement results of the characteristics of the magnetic sensor will now be described.

The structure (the detector 50S) described in reference to FIG. 18A and FIG. 18B is made. Two detectors 50S are prepared.

Figure 35:
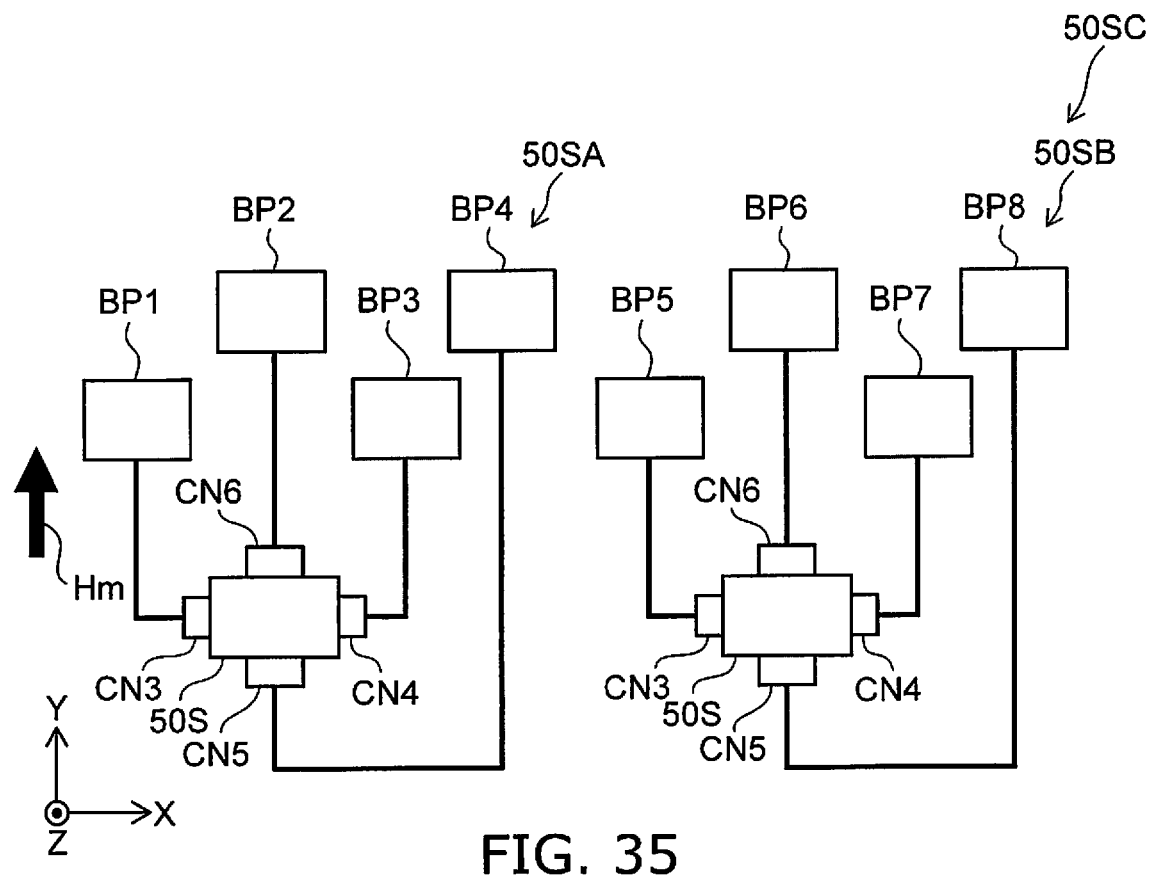
FIG. 35 is a schematic view illustrating a sample of the magnetic sensor.

FIG. 35 is a schematic view illustrating a sample of the magnetic sensor.

An abbreviated illustration of the two detectors 50S is shown in FIG. 35. The connecting conductive portion CN3, the connecting conductive portion CN4, the connecting conductive portion CN5, and the connecting conductive portion CN6 (referring to FIG. 18A and FIG. 18B) are provided in each of the two detectors 50S.

In one of the two detectors 50S (a first evaluation element 50SA), the connecting conductive portion CN3 is connected to a bonding pad BP1. The connecting conductive portion CN4 is connected to a bonding pad BP3. The connecting conductive portion CN5 is connected to a bonding pad BP4. The connecting conductive portion CN6 is connected to a bonding pad BP2.

In the other one of the two detectors 50S (a second evaluation element 50SB), the connecting conductive portion CN3 is connected to a bonding pad BP5. The connecting conductive portion CN4 is connected to a bonding pad BP7. The connecting conductive portion CN5 is connected to a bonding pad BP8. The connecting conductive portion CN6 is connected to a bonding pad BP6.

The first test element 50SA and the second test element 50SB are used as an test element 50SC. The easy axes of the magnetic layers included in the elements are aligned with the X-axis direction. The magnetic field Hm from the measurement object is aligned with the Y-axis direction.

Figure 36:
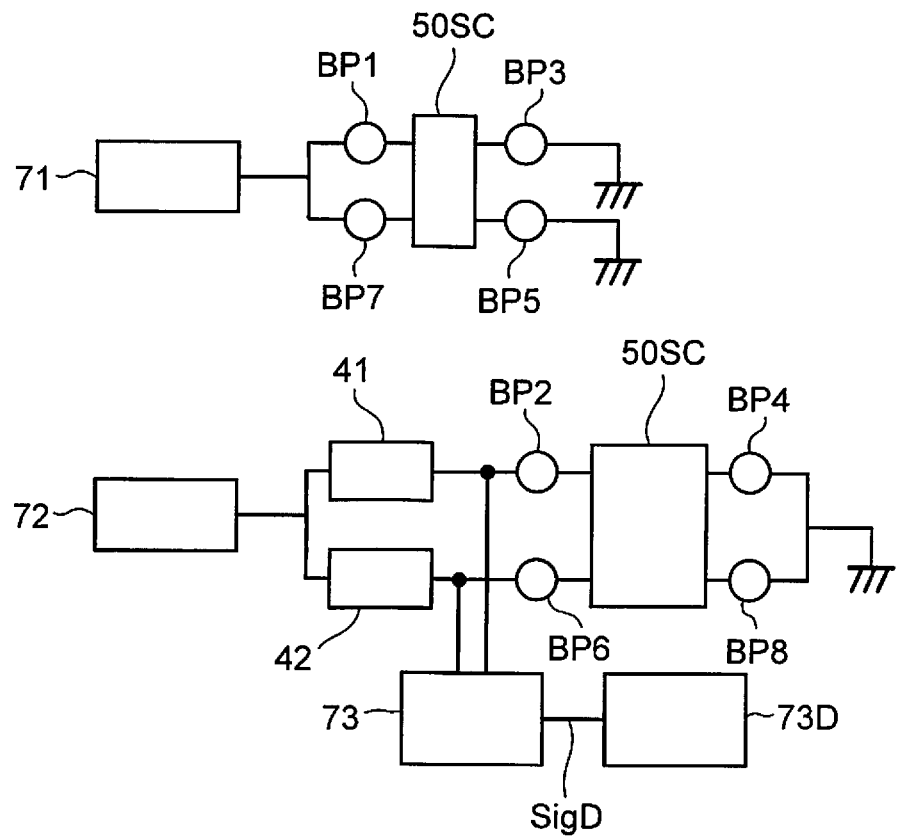
FIG. 36 is a schematic view illustrating a measurement circuit of the characteristics of the sample of the magnetic sensor.

FIG. 36 is a schematic view illustrating a measurement circuit of the characteristics of the sample of the magnetic sensor.

As shown in FIG. 36, the output of the first circuit portion 71 is input to the bonding pad BP1 and the bonding pad BP7. The bonding pad BP3 and the bonding pad BP5 are grounded. The bonding pad BP4 and the bonding pad BP8 are grounded. The bonding pad BP2 and the bonding pad BP6 are electrically connected to the third circuit portion 73. The third circuit portion 73 is, for example, a differential amplifier. The amplification factor of the differential amplifier may be 1. An output SigD of the third circuit portion 73 is supplied to an oscilloscope 73D.

In the example, resistances of 677Ω are used as the first resistor 41 and the second resistor 42. An alternating current of 10 kHz having an amplitude of 9 V is output from the first circuit portion 71. A direct current voltage (a direct current) of 5 V is output from the second circuit portion 72.

Figure 37:
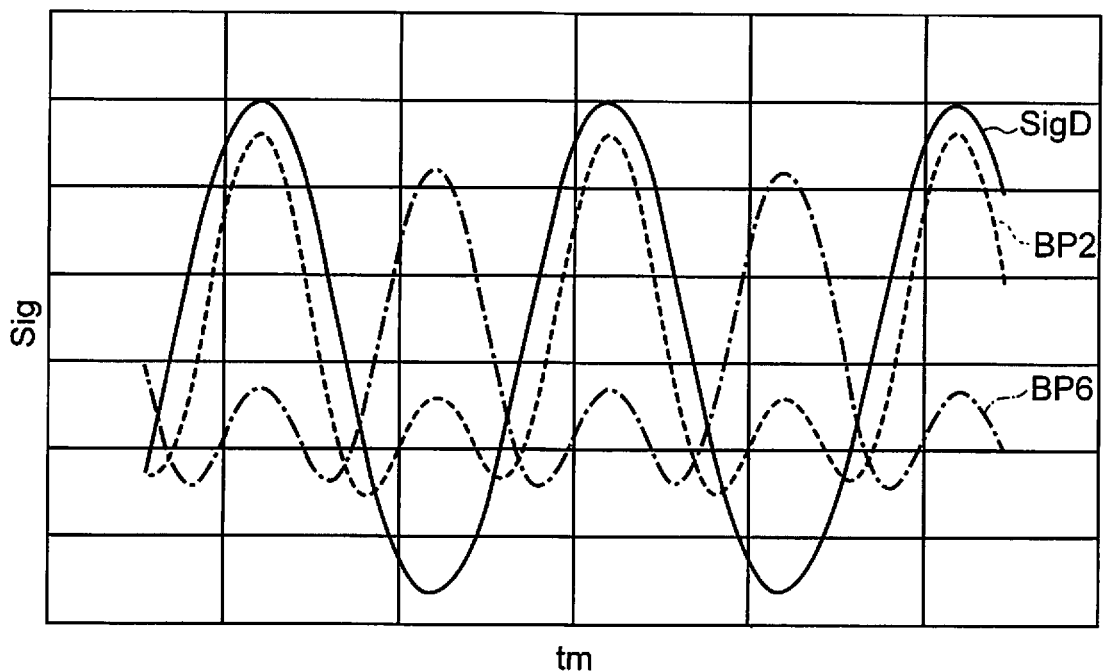
FIG. 37 is a graph illustrating measurement results of the characteristics of the sample of the magnetic sensor.

FIG. 37 is a graph illustrating measurement results of the characteristics of the sample of the magnetic sensor.

FIG. 37 illustrates the signals observed by the oscilloscope 73D. The horizontal axis corresponds to the time tm. The vertical axis corresponds to the strength of the signal Sig. The output SigD of the third circuit portion 73 is illustrated in FIG. 37. Also, the signals of the bonding pad BP2 and the bonding pad BP6 are illustrated in FIG. 37. The signals shown in FIG. 37 are displayed with different magnifications of the vertical axis for ease of comparison.

As shown in FIG. 37, the signals of the bonding pad BP2 and the bonding pad BP6 include components of the first frequency f1 and components of the double frequency 2f1. In the output SigD of the third circuit portion 73, the component of the double frequency 2f1 is substantially not observed; and the component of the first frequency f1 is observed.

Figure 38A:
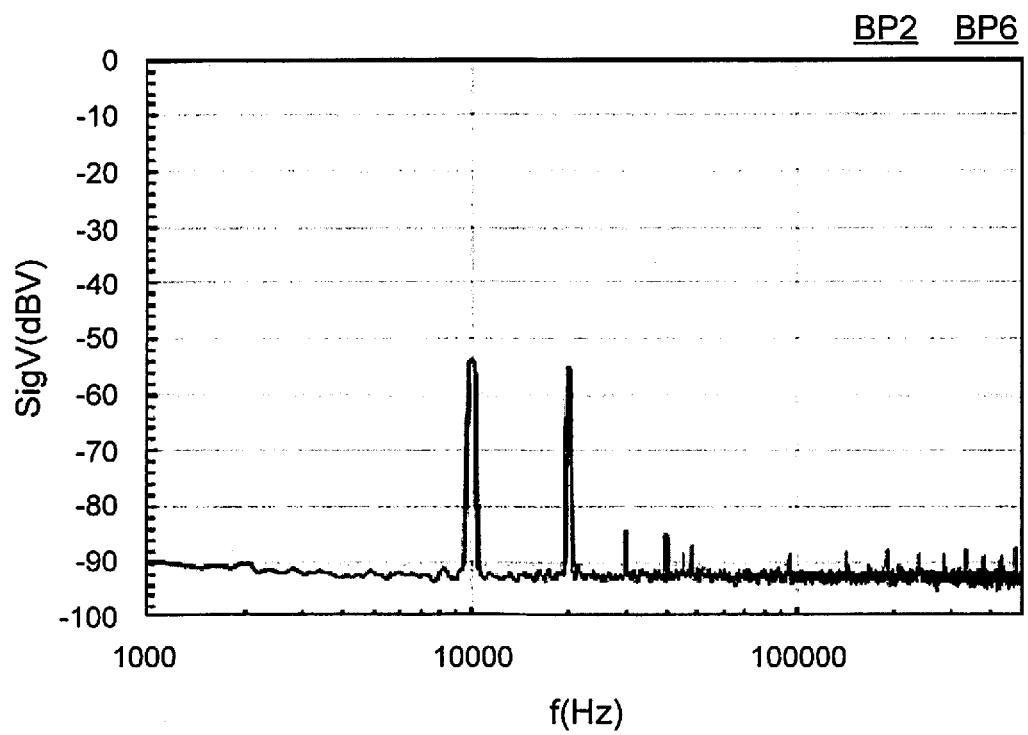
FIG. 38A and FIG. 38B are graphs illustrating the measurement results of the characteristics of the sample of the magnetic sensor.
Figure 38B:
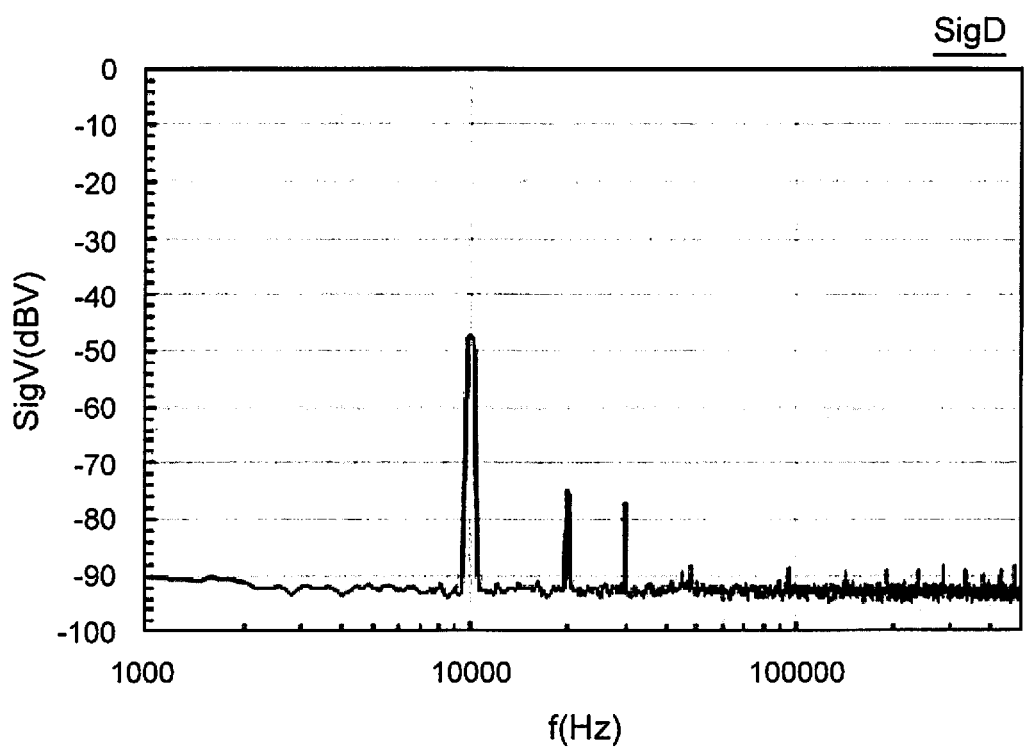

FIG. 38A and FIG. 38B are graphs illustrating the measurement results of the characteristics of the sample of the magnetic sensor.

These figures illustrate the results of FFT analysis of the signals illustrated in FIG. 37. In these figures, the horizontal axis corresponds to a frequency f (Hz). In these figures, the vertical axis corresponds to the strengths of each frequency components of the output signals (displayed in dBV). FIG. 38A corresponds to the signals of the bonding pad BP2 and the bonding pad BP6. FIG. 38B corresponds to the output SigD of the third circuit portion 73.

As shown in FIG. 38A, in the signals of the bonding pad BP2 and the bonding pad BP6, a peak at the first frequency f1 (10 kHz) and a peak at the double frequency 2f1 (20 kHz) are observed. The intensity of the peak at the double frequency 2f1 (20 kHz) is high and is about the same as the peak at the first frequency f1 (10 kHz).

In the output SigD of the third circuit portion 73 as shown in FIG. 38B, the peak at the first frequency f1 (10 kHz) is high; and the peak at the double frequency 2f1 (20 kHz) is low.

In a magnetic sensor utilizing the tunneling magnetoresistance effect (TMR), there is a reference example including a bridge using four TMR elements. In the reference example, the direction of the magnetization of the free magnetic layer is set to cross the direction of the magnetization of the reference layer. It is considered that by using such a configuration, a large change of the resistance with respect to the magnetic field from the outside can be obtained. For the case of the reference example, for example, the magnetic field-resistance characteristic has an odd-function characteristic. When AC magnetic fields with opposite phases to each other are used, it is difficult to remove the signal including the component of the double frequency 2f1.

An application example of the magnetic sensor according to the embodiment will now be described.

Third Embodiment

For example, a magnetic sensor according to the embodiment is applicable to a testing device, etc.

Figure 39:
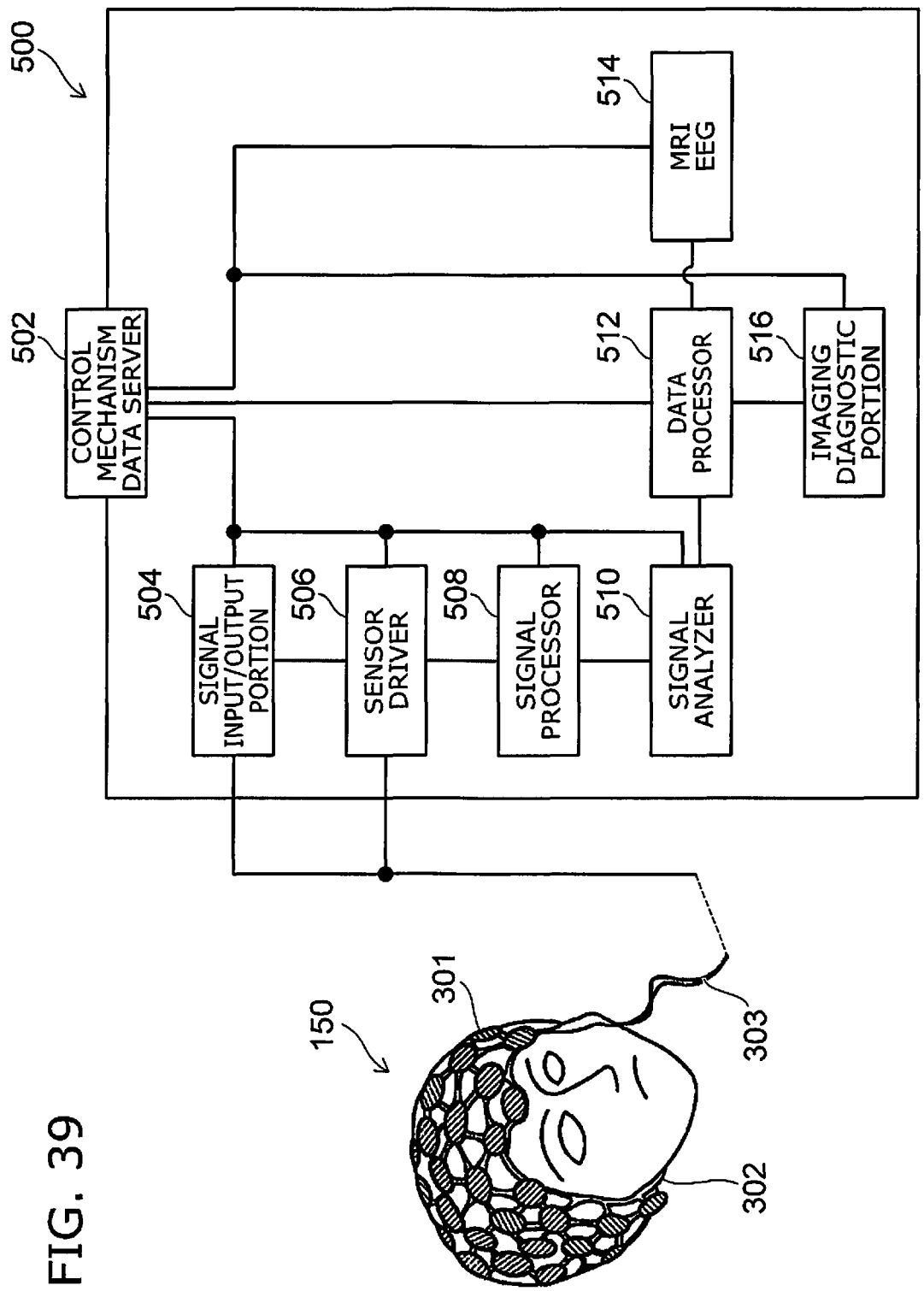
FIG. 39 is a schematic view showing a magnetic sensor and a testing device according to a third embodiment.

FIG. 39 is a schematic view showing the magnetic sensor and the testing device according to the third embodiment.

As shown in FIG. 39, the testing device 500 includes a magnetic sensor 150. The magnetic sensor 150 includes the magnetic sensors (and the magnetic sensor devices) described in reference to the first embodiment and the second embodiment and modifications of the magnetic sensors (and the magnetic sensor devices).

In the testing device 500, the magnetic sensor 150 is, for example, a magnetoencephalograph device. The magnetoencephalograph device detects a magnetic field generated by cranial nerves. In the case where the magnetic sensor 150 is included in a magnetoencephalograph device, the size of the magnetic element included in the magnetic sensor 150 is, for example, not less than 1 mm but less than 10 mm. The size is, for example, the length including the MFC.

As shown in FIG. 39, the magnetic sensor 150 (the magnetoencephalograph device) is mounted to, for example, the head of a human body. The magnetic sensor 150 (the magnetoencephalograph device) includes a sensor portion 301 (a first sensor portion SU1 or the like). The magnetic sensor 150 (the magnetoencephalograph device) may include multiple sensor portions 301 (the first sensor portion SU1, a second sensor portion SU2, etc.). The number of the multiple sensor portions 301 is, for example, about 100 (e.g., not less than 50 and not more than 150). The multiple sensor portions 301 are provided in a base 302 that is flexible.

The magnetic sensor 150 may include, for example, a circuit for differential detection, etc. The magnetic sensor 150 may include a sensor other than a magnetic sensor (e.g., a potential terminal, an acceleration sensor, etc.).

The size of the magnetic sensor 150 (the magnetic sensors described in reference to the first embodiment and the second embodiment) is small compared to the size of a conventional SQUID magnetic sensor. Therefore, the mounting of the multiple sensor portions 301 is easy. The mounting of the multiple sensor portions 301 and the other circuits is easy. It is easy for the multiple sensor portions 301 to coexist with the other sensors.

The base 302 may include, for example, an elastic body such as a silicone resin, etc. For example, the multiple sensor portions 301 are provided in the base 302 by being linked to each other. For example, the base 302 can be closely adhered to the head.

An input/output cord 303 of the sensor portion 301 is connected to a signal input/output portion 504 and a sensor driver 506 of the testing device 500. Magnetic field measurement is performed in the sensor portion 301 using the electrical power from the sensor driver 506 and the control signal from the signal input/output portion 504. The result of the magnetic field measurement is input to the signal input/output portion 504. The signal that is obtained by the signal input/output portion 504 is supplied to a signal processor 508. Processing such as, for example, the removal of noise, filtering, amplification, signal calculation, etc., are performed in the signal processor 508. The signal that is processed by the signal processor 508 is supplied to a signal analyzer 510. For example, the signal analyzer 510 extracts a designated signal for magnetoencephalography. For example, signal analysis with phase matching is performed in the signal analyzer 510.

The output of the signal analyzer 510 (the data for which the signal analysis has ended) is supplied to a data processor 512. Data analysis is performed in the data processor 512. It is possible to include image data such as, for example, MRI (Magnetic Resonance Imaging), etc., in the data analysis. It is possible to include, for example, scalp potential information such as an EEG (Electroencephalogram), etc., in the data analysis. For example, nerve firing point analysis, inverse analysis, or the like is performed by the data analysis.

For example, the result of the data analysis is supplied to an imaging test portion 516. Imaging is performed by the imaging test portion 516. The diagnosis is supported by the imaging.

For example, the series of operations recited above is controlled by a control mechanism 502. For example, necessary data such as preliminary signal data, metadata partway through the data processing, or the like is stored in a data server. The data server and the control mechanism may be integrated.

The testing device 500 according to the embodiment includes the magnetic sensor 150, and a processor that processes the signal obtained from the magnetic sensor 150. The processor includes, for example, at least one of the signal processor 508 or the data processor 512. The processor includes, for example, a computer, etc.

In the magnetic sensor 150 shown in FIG. 39, the sensor portion 301 is mounted to the head of a human body. The sensor portion 301 may be mounted to the chest of the human body. Thereby, magnetocardiography is possible. For example, the sensor portion 301 may be mounted to the abdomen of a pregnant woman. Thereby, palmoscopy of the fetus can be performed.

It is favorable for the magnetic sensor device including the participant to be mounted inside a shielded room. Thereby, for example, the influence of geomagnetism or magnetic noise can be suppressed.

For example, a mechanism may be provided to locally shield the sensor portion 301 or the measurement section of the human body. For example, a shield mechanism may be provided in the sensor portion 301. For example, the signal analysis or the data processing may be effectively shielded.

In the embodiment, the base 302 may be flexible or substantially may not be flexible. In the example shown in FIG. 39, the base 302 is a continuous film that is patterned into a hat-like configuration. The base 302 may have a net configuration. Thereby, for example, good wearability is obtained. For example, the adhesion of the base 302 with the human body improves. The base 302 may have a hard helmet-like configuration.

Figure 40:
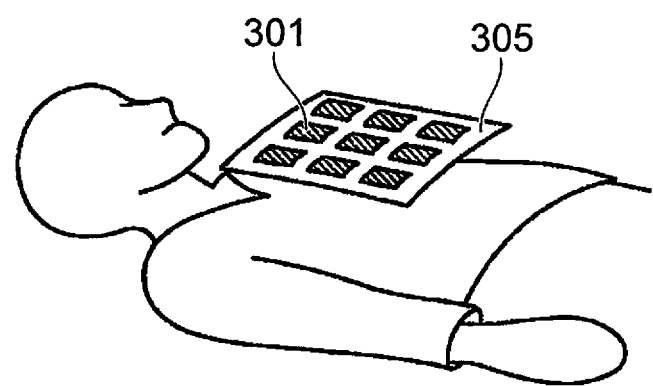
FIG. 40 is a schematic view showing another magnetic sensor according to a fourth embodiment.

FIG. 40 is a schematic view showing another magnetic sensor according to the fourth embodiment.

FIG. 40 is an example of a magnetic detection instrument. In the example shown in FIG. 40, the sensor portion 301 is provided on a hard base 305 having a flat plate configuration.

The input and output of the signal obtained from the sensor portion 301 in the example shown in FIG. 40 is similar to the input and output described in reference to FIG. 39. The processing of the signal obtained from the sensor portion 301 in the example shown in FIG. 40 is similar to the processing described in reference to FIG. 39.

There is a reference example in which a SQUID (Superconducting Quantum Interference Device) magnetic sensor is used as a device to measure a faint magnetic field such as a magnetic field generated from a living body, etc. Because superconductivity is used in the reference example, the device is large; and the power consumption is large. The burden on the measurement object (the patient) is large.

According to the embodiment, the device can be small. The power consumption can be suppressed. The burden on the measurement object (the patient) can be reduced.

According to the embodiment, the SN ratio of the magnetic field detection can be improved. The detection sensitivity can be increased.

The embodiments may include the following configurations (e.g., technological proposals).

Configuration 1

A magnetic sensor, comprising:
a first element including a first magnetic layer;
a second element including a second magnetic layer;
a first interconnect;
a second interconnect;
a first circuit portion electrically connected to the first interconnect and the second interconnect; and
a second circuit portion electrically connected to the first element and the second element,
the first circuit portion being configured to supply a first alternating current to the first interconnect and to supply a second alternating current to the second interconnect,
the second circuit portion being configured to supply a first element current to the first element and to supply a second element current to the second element,
at a first time, the first alternating current having a first alternating current orientation, and the second alternating current having a second alternating current orientation,
at a second time, the first alternating current having a reverse orientation of the first alternating current orientation, and the second alternating current having a reverse orientation of the second alternating current orientation,
at the first time, the first element current having a first element current orientation, and the second element current having a second element current orientation,
at the second time, the first element current having the first element current orientation, and the second element current having the second element current orientation,
the first alternating current orientation having a component in an orientation of the first element current,
the second alternating current orientation having a component in an opposite orientation to an orientation of the second element current.

Configuration 2

The magnetic sensor according to Configuration 1, wherein
a distance between the first interconnect and the first element is shorter than a distance between the first interconnect and the second element,
a distance between the second interconnect and the second element is shorter than a distance between the second interconnect and the first element,
the first interconnect includes a first interconnect end portion and a second interconnect end portion,
the second interconnect includes a third interconnect end portion and a fourth interconnect end portion,
an orientation from the third interconnect end portion toward the fourth interconnect end portion is aligned with an orientation from the first interconnect end portion toward the second interconnect end portion,
at the first time, the first alternating current has the orientation from the first interconnect end portion toward the second interconnect end portion,
at the first time, the second alternating current has an orientation from the fourth interconnect end portion toward the third interconnect end portion.

Configuration 3

The magnetic sensor according to Configuration 1, wherein the first element and the second element are electrically connected in series.

Configuration 4

The magnetic sensor according to Configuration 3, further comprising a third circuit portion,
the first element including a first element end portion and a second element end portion,
the second element including a third element end portion and a fourth element end portion,
the second element end portion and the fourth element end portion being electrically connected to each other,
the second circuit portion being electrically connected to the first element end portion and the third element end portion,
the third circuit portion being electrically connected to the second element end portion and the fourth element end portion,
the third circuit portion outputting a signal corresponding to a change of an electric potential of the second element end portion and the fourth element end portion.

Configuration 5

The magnetic sensor according to Configuration 4, wherein
the first alternating current and the second alternating current have a first frequency, and
the signal corresponds to a component of the first frequency of the change of the electric potential of the second element end portion and the fourth element end portion.

Configuration 6

The magnetic sensor according to Configuration 1 or 2, further comprising:
a first resistor; and
a second resistor,
the first element including a first element end portion and a second element end portion,
the second element including a third element end portion and a fourth element end portion,
the second element end portion and the fourth element end portion being electrically connected to each other,
the first resistor including a first resistor end portion and a second resistor end portion,
the second resistor including a third resistor end portion and a fourth resistor end portion,
the second resistor end portion and the first element end portion being electrically connected to each other,
the fourth resistor end portion and the third element end portion being electrically connected to each other,
the second circuit portion being electrically connected to the first resistor end portion, the third resistor end portion, the second element end portion, and the fourth element end portion,
the second circuit portion is configured to supply the first element current to a set of the first resistor and the first element and to supply the second element current to a set of the second resistor and the second element.

Configuration 7

The magnetic sensor according to Configuration 6, further comprising a third circuit portion,
the third circuit portion outputting a signal corresponding to a difference between an electric potential of the first element end portion and an electric potential of the third element end portion.

Configuration 8

The magnetic sensor according to Configuration 7, wherein the first resistor includes a third magnetic layer, a third opposing magnetic layer, and a third nonmagnetic layer provided between the third magnetic layer and the third opposing magnetic layer, and the second resistor includes a fourth magnetic layer, a fourth opposing magnetic layer, and a fourth nonmagnetic layer provided between the fourth magnetic layer and the fourth opposing magnetic layer.

Configuration 9

A magnetic sensor, comprising:

a first element including a first magnetic layer;

a second element including a second magnetic layer;

a first interconnect;

a second interconnect;

a first circuit portion electrically connected to the first interconnect and the second interconnect; and a second circuit portion electrically connected to the first element and the second element, the first circuit portion being configured to supply a first alternating current to the first interconnect and to supply a second alternating current to the second interconnect, the second circuit portion being configured to supply a first element current to the first element and to supply a second element current to the second element, at least for some time, a phase of the first alternating current being opposite to a phase of the second alternating current with respect to an orientation of an external magnetic field applied to the first element and the second element.

Configuration 10

The magnetic sensor according to any one of Configurations 1 to 9, further comprising:

a first magnetic portion;

a first nonmagnetic region provided between the first magnetic portion and the first element;

a second magnetic portion; and a second nonmagnetic region provided between the second magnetic portion and the second element.

Configuration 11

A magnetic sensor, comprising:

a first element including a first magnetic layer;

a second element including a second magnetic layer;

a third element including a third magnetic layer;

a fourth element including a fourth magnetic layer;

first to fourth interconnects;

a first circuit portion electrically connected to the first to fourth interconnects; and a second circuit portion electrically connected to the first to fourth elements, the first circuit portion being configured to supply first to fourth alternating currents respectively to the first to fourth interconnects, the second circuit portion being configured to supply first to fourth element currents respectively to the first to fourth elements, at a first time, the first to fourth alternating currents respectively having first to fourth alternating current orientations, at a second time, the first to fourth alternating currents respectively having opposite orientations to the first to fourth alternating current orientations, at the first time, the first to fourth element currents having first to fourth element current-alternating current orientations, at the second time, the first to fourth element currents having the first to fourth element current-alternating current orientations, the first alternating current orientation having a component in an orientation of the first element current, the second alternating current orientation having a component in an opposite orientation to an orientation of the second element current, the third alternating current orientation having a component in an orientation of the third element current, the fourth alternating current orientation having a component in an opposite orientation to an orientation of the fourth element current.

Configuration 12

The magnetic sensor according to Configuration 11, wherein a distance between the first interconnect and the first element is shorter than a distance between the first interconnect and the second element, shorter than a distance between the first interconnect and the third element, and shorter than a distance between the first interconnect and the fourth element, a distance between the second interconnect and the second element is shorter than a distance between the second interconnect and the first element, shorter than a distance between the second interconnect and the third element, and shorter than a distance between the second interconnect and the fourth element, a distance between the third interconnect and the third element is shorter than a distance between the third interconnect and the first element, shorter than a distance between the third interconnect and the second element, and shorter than a distance between the third interconnect and the fourth element, a distance between the fourth interconnect and the fourth element is shorter than a distance between the fourth interconnect and the first element, shorter than a distance between the fourth interconnect and the second element, and shorter than a distance between the fourth interconnect and the third element, the first interconnect includes a first interconnect end portion and a second interconnect end portion, the second interconnect includes a third interconnect end portion and a fourth interconnect end portion, the third interconnect includes a fifth interconnect end portion and a sixth interconnect end portion, the fourth interconnect includes a seventh interconnect end portion and an eighth interconnect end portion, an orientation from the third interconnect end portion toward the fourth interconnect end portion is aligned with an orientation from the first interconnect end portion toward the second interconnect end portion, an orientation from the seventh interconnect end portion toward the eighth interconnect end portion is aligned with an orientation from the fifth interconnect end portion toward the sixth interconnect end portion, the orientation from the seventh interconnect end portion toward the eighth interconnect end portion is aligned with the orientation from the first interconnect end portion toward the second interconnect end portion, at the first time, the first alternating current has the orientation from the first interconnect end portion toward the second interconnect end portion, at the first time, the second alternating current has an orientation from the fourth interconnect end portion toward the third interconnect end portion, at the first time, the third alternating current has the orientation from the fifth interconnect end portion toward the sixth interconnect end portion, at the first time, the fourth alternating current has an orientation from the eighth interconnect end portion toward the seventh interconnect end portion.

Configuration 13

The magnetic sensor according to Configuration 12, wherein the first element and the second element are electrically connected in series, and the fourth element and the third element are electrically connected in series.

Configuration 14

The magnetic sensor according to Configuration 13, wherein the first element includes a first element end portion and a second element end portion, the second element includes a third element end portion and a fourth element end portion, the third element includes a fifth element end portion and a sixth element end portion, the fourth element includes a seventh element end portion and an eighth element end portion, the first element end portion and the seventh element end portion are electrically connected to each other, the fourth element end portion and the sixth element end portion are electrically connected to each other, the second element end portion and the third element end portion are electrically connected to each other, the eighth element end portion and the fifth element end portion are electrically connected to each other, and the second circuit portion is electrically connected to the first element end portion, the seventh element end portion, the fourth element end portion, and the sixth element end portion.

Configuration 15

The magnetic sensor according to Configuration 14, further comprising a third circuit portion, the third circuit portion outputting a signal corresponding to a difference between a potential of the second element end portion and a potential of the eighth element end portion.

Configuration 16

The magnetic sensor according to any one of Configurations 11 to 15, wherein the third element further includes a third opposing magnetic layer, and a third nonmagnetic layer provided between the third magnetic layer and the third opposing magnetic layer, and the fourth element further includes a fourth opposing magnetic layer, and a fourth nonmagnetic layer provided between the fourth magnetic layer and the fourth opposing magnetic layer.

Configuration 17

The magnetic sensor according to Configuration 16, wherein a length of the third magnetic layer along a third magnetic layer direction crossing a third stacking direction is longer than a length of the third magnetic layer along a third magnetic layer cross direction crossing a plane including the third stacking direction and the third magnetic layer direction, the third stacking direction being from the third opposing magnetic layer toward the third magnetic layer, and a length of the fourth magnetic layer along a fourth magnetic layer direction crossing a fourth stacking direction is longer than a length of the fourth magnetic layer along a fourth magnetic layer cross direction crossing a plane including the fourth stacking direction and the fourth magnetic layer direction, the fourth stacking direction being from the fourth opposing magnetic layer toward the fourth magnetic layer.

Configuration 18

The magnetic sensor according to any one of Configurations 1 to 17, wherein the first element further includes a first opposing magnetic layer, and a first nonmagnetic layer provided between the first magnetic layer and the first opposing magnetic layer, and the second element further includes a second opposing magnetic layer, and a second nonmagnetic layer provided between the second magnetic layer and the second opposing magnetic layer.

Configuration 19

The magnetic sensor according to Configuration 18, wherein a length of the first magnetic layer along a first magnetic layer direction crossing a first stacking direction is longer than a length of the first magnetic layer along a first magnetic layer cross direction crossing a plane including the first stacking direction and the first magnetic layer direction, the first stacking direction being from the first opposing magnetic layer toward the first magnetic layer, and a length of the second magnetic layer along a second magnetic layer direction crossing a second stacking direction is longer than a length of the second magnetic layer along a second magnetic layer cross direction crossing a plane including the second stacking direction and the second magnetic layer direction, the second stacking direction being from the second opposing magnetic layer toward the second magnetic layer.

Configuration 20

The magnetic sensor according to any one of Configurations 1 to 19, wherein an electrical resistance of the first element has an even-function characteristic with respect to a magnetic field applied to the first element, and an electrical resistance of the second element has an even-function characteristic with respect to a magnetic field applied to the second element.

Configuration 21

A testing device, comprising:

the magnetic sensor according to any one of Configurations 1 to 20; and a processor processing a signal obtained from the magnetic sensor.

According to the embodiments, a magnetic sensor and a testing device can be provided in which the detection sensitivity can be increased.

In the specification of the application, "perpendicular" and "parallel" refer to not only strictly perpendicular and strictly parallel but also include, for example, the fluctuation due to manufacturing processes, etc. It is sufficient to be substantially perpendicular and substantially parallel.

Hereinabove, exemplary embodiments of the invention are described with reference to specific examples. However, the embodiments of the invention are not limited to these specific examples. For example, one skilled in the art may similarly practice the invention by appropriately selecting specific configurations of components included in magnetic sensors such as elements, magnetic layers, nonmagnetic layers, interconnects, resistors, circuit portions, etc., from known art. Such practice is included in the scope of the invention to the extent that similar effects thereto are obtained.

Further, any two or more components of the specific examples may be combined within the extent of technical feasibility and are included in the scope of the invention to the extent that the purport of the invention is included.

Moreover, all magnetic sensors, testing devices practicable by an appropriate design modification by one skilled in the art based on the magnetic sensors and the testing devices described above as embodiments of the invention also are within the scope of the invention to the extent that the spirit of the invention is included.

Various other variations and modifications can be conceived by those skilled in the art within the spirit of the invention, and it is understood that such variations and modifications are also encompassed within the scope of the invention.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the invention.

What is claimed is:

1. A magnetic sensor, comprising:
   a first element including a first magnetic layer;
   a second element including a second magnetic layer;
   a first interconnect;
   a second interconnect;
   a first circuit portion electrically connected to the first interconnect and the second interconnect; and
   a second circuit portion electrically connected to the first element and the second element,
   the first circuit portion being configured to supply a first alternating current to the first interconnect and to supply a second alternating current to the second interconnect,
   the second circuit portion being configured to supply a first element current to the first element and to supply a second element current to the second element,
   at a first time, the first alternating current having a first alternating current orientation, and the second alternating current having a second alternating current orientation,
   at a second time, the first alternating current having an opposite orientation to the first alternating current orientation, and the second alternating current having an opposite orientation to the second alternating current orientation,
   at the first time, the first element current having a first element current orientation, and the second element current having a second element current orientation,
   at the second time, the first element current having the first element current orientation, and the second element current having the second element current orientation,
   the first alternating current orientation having a component in an orientation of the first element current,
   the second alternating current orientation having a component in an opposite orientation to an orientation of the second element current.

2. The sensor according to claim 1, wherein
   a distance between the first interconnect and the first element is shorter than a distance between the first interconnect and the second element,
   a distance between the second interconnect and the second element is shorter than a distance between the second interconnect and the first element,
   the first interconnect includes a first interconnect end portion and a second interconnect end portion,
   the second interconnect includes a third interconnect end portion and a fourth interconnect end portion,
   an orientation from the third interconnect end portion toward the fourth interconnect end portion is aligned with an orientation from the first interconnect end portion toward the second interconnect end portion,
   at the first time, the first alternating current has the orientation from the first interconnect end portion toward the second interconnect end portion,
   at the first time, the second alternating current has an orientation from the fourth interconnect end portion toward the third interconnect end portion.

3. The sensor according to claim 1, wherein the first element and the second element are electrically connected in series.

4. The sensor according to claim 3, further comprising a third circuit portion,
   the first element including a first element end portion and a second element end portion,
   the second element including a third element end portion and a fourth element end portion,
   the second element end portion and the fourth element end portion being electrically connected to each other,
   the second circuit portion being electrically connected to the first element end portion and the third element end portion,
   the third circuit portion being electrically connected to the second element end portion and the fourth element end portion,
   the third circuit portion outputting a signal corresponding to a change of a potential of the second element end portion and the fourth element end portion.

5. The sensor according to claim 4, wherein
   the first alternating current and the second alternating current have a first frequency, and
   the signal corresponds to a component of the first frequency of the change of the potential of the second element end portion and the fourth element end portion.

6. The sensor according to claim 1, further comprising:
   a first resistor; and
   a second resistor,
   the first element including a first element end portion and a second element end portion,
   the second element including a third element end portion and a fourth element end portion,
   the second element end portion and the fourth element end portion being electrically connected to each other,
   the first resistor including a first resistor end portion and a second resistor end portion,
   the second resistor including a third resistor end portion and a fourth resistor end portion,
   the second resistor end portion and the first element end portion being electrically connected to each other, the fourth resistor end portion and the third element end portion being electrically connected to each other, the second circuit portion being electrically connected to the first resistor end portion, the third resistor end portion, the second element end portion, and the fourth element end portion, the second circuit portion being configured to supply the first element current to a set of the first resistor and the first element and to supply the second element current to a set of the second resistor and the second element.

7. The sensor according to claim 6, further comprising a third circuit portion, the third circuit portion outputting a signal corresponding to a difference between an electric potential of the first element end portion and an electric potential of the third element end portion.

8. The sensor according to claim 7, wherein the first resistor includes a third magnetic layer, a third opposing magnetic layer, and a third nonmagnetic layer provided between the third magnetic layer and the third opposing magnetic layer, and the second resistor includes a fourth magnetic layer, a fourth opposing magnetic layer, and a fourth nonmagnetic layer provided between the fourth magnetic layer and the fourth opposing magnetic layer.

9. The magnetic sensor according to claim 1, wherein an electrical resistance of the first element has an even-function characteristic with respect to a magnetic field applied to the first element, and an electrical resistance of the second element has an even-function characteristic with respect to a magnetic field applied to the second element.

10. A testing device, comprising:

the magnetic sensor according to claim 1; and a processor processing a signal obtained from the magnetic sensor.

11. A magnetic sensor, comprising:

a first element including a first magnetic layer;

a second element including a second magnetic layer;

a first interconnect;

a second interconnect;

a first circuit portion electrically connected to the first interconnect and the second interconnect; and a second circuit portion electrically connected to the first element and the second element, the first circuit portion being configured to supply a first alternating current to the first interconnect and to supply a second alternating current to the second interconnect, the second circuit portion being configured to supply a first element current to the first element and to supply a second element current to the second element, at least for some time, a phase of the first alternating current being opposite to a phase of the second alternating current with respect to an orientation of an external magnetic field applied to the first element and the second element.

12. The sensor according to claim 1, further comprising:

a first magnetic portion;

a first nonmagnetic region provided between the first magnetic portion and the first element;

a second magnetic portion; and a second nonmagnetic region provided between the second magnetic portion and the second element.

13. A magnetic sensor, comprising:

a first element including a first magnetic layer;

a second element including a second magnetic layer;

a third element including a third magnetic layer;

a fourth element including a fourth magnetic layer;

first to fourth interconnects;

a first circuit portion electrically connected to the first to fourth interconnects; and a second circuit portion electrically connected to the first to fourth elements, the first circuit portion being configured to supply first to fourth alternating currents respectively to the first to fourth interconnects, the second circuit portion being configured to supply first to fourth element currents respectively to the first to fourth elements, at a first time, the first to fourth alternating currents respectively having first to fourth alternating current orientations, at a second time, the first to fourth alternating currents respectively having opposite orientations to the first to fourth alternating current orientations, at the first time, the first to fourth element currents having first to fourth element current-alternating current orientations, at the second time, the first to fourth element currents having the first to fourth element current-alternating current orientations, the first alternating current orientation having a component in an orientation of the first element current, the second alternating current orientation having a component in an opposite orientation to an orientation of the second element current, the third alternating current orientation having a component in an orientation of the third element current, the fourth alternating current orientation having a component in an opposite orientation to an orientation of the fourth element current.

14. The sensor according to claim 13, wherein a distance between the first interconnect and the first element is shorter than a distance between the first interconnect and the second element, shorter than a distance between the first interconnect and the third element, and shorter than a distance between the first interconnect and the fourth element, a distance between the second interconnect and the second element is shorter than a distance between the second interconnect and the first element, shorter than a distance between the second interconnect and the third element, and shorter than a distance between the second interconnect and the fourth element, a distance between the third interconnect and the third element is shorter than a distance between the third interconnect and the first element, shorter than a distance between the third interconnect and the second element, and shorter than a distance between the third interconnect and the fourth element, a distance between the fourth interconnect and the fourth element is shorter than a distance between the fourth interconnect and the first element, shorter than a distance between the fourth interconnect and the second element, and shorter than a distance between the fourth interconnect and the third element, the first interconnect includes a first interconnect end portion and a second interconnect end portion, the second interconnect includes a third interconnect end portion and a fourth interconnect end portion, the third interconnect includes a fifth interconnect end portion and a sixth interconnect end portion, the fourth interconnect includes a seventh interconnect end portion and an eighth interconnect end portion, an orientation from the third interconnect end portion toward the fourth interconnect end portion is aligned with an orientation from the first interconnect end portion toward the second interconnect end portion, an orientation from the seventh interconnect end portion toward the eighth interconnect end portion is aligned with an orientation from the fifth interconnect end portion toward the sixth interconnect end portion, the orientation from the seventh interconnect end portion toward the eighth interconnect end portion is aligned with the orientation from the first interconnect end portion toward the second interconnect end portion, at the first time, the first alternating current has the orientation from the first interconnect end portion toward the second interconnect end portion, at the first time, the second alternating current has an orientation from the fourth interconnect end portion toward the third interconnect end portion, at the first time, the third alternating current has the orientation from the fifth interconnect end portion toward the sixth interconnect end portion, at the first time, the fourth alternating current has an orientation from the eighth interconnect end portion toward the seventh interconnect end portion.

15. The sensor according to claim 14, wherein
the first element and the second element are electrically connected in series, and
the fourth element and the third element are electrically connected in series.

16. The sensor according to claim 15, wherein
the first element includes a first element end portion and a second element end portion,
the second element includes a third element end portion and a fourth element end portion,
the third element includes a fifth element end portion and a sixth element end portion,
the fourth element includes a seventh element end portion and an eighth element end portion,
the first element end portion and the seventh element end portion are electrically connected to each other,
the fourth element end portion and the sixth element end portion are electrically connected to each other,
the second element end portion and the third element end portion are electrically connected to each other,
the eighth element end portion and the fifth element end portion are electrically connected to each other, and
the second circuit portion is electrically connected to the first element end portion, the seventh element end portion, the fourth element end portion, and the sixth element end portion.

17. The sensor according to claim 13, wherein
the third element further includes a third opposing magnetic layer, and a third nonmagnetic layer provided between the third magnetic layer and the third opposing magnetic layer, and
the fourth element further includes a fourth opposing magnetic layer, and a fourth nonmagnetic layer provided between the fourth magnetic layer and the fourth opposing magnetic layer.

18. The sensor according to claim 17, wherein
a length of the third magnetic layer along a third magnetic layer direction crossing a third stacking direction is longer than a length of the third magnetic layer along a third magnetic layer cross direction crossing a plane including the third stacking direction and the third magnetic layer direction, the third stacking direction being from the third opposing magnetic layer toward the third magnetic layer, and
a length of the fourth magnetic layer along a fourth magnetic layer direction crossing a fourth stacking direction is longer than a length of the fourth magnetic layer along a fourth magnetic layer cross direction crossing a plane including the fourth stacking direction and the fourth magnetic layer direction, the fourth stacking direction being from the fourth opposing magnetic layer toward the fourth magnetic layer.

19. The sensor according to claim 1, wherein
the first element further includes a first opposing magnetic layer, and a first nonmagnetic layer provided between the first magnetic layer and the first opposing magnetic layer, and
the second element further includes a second opposing magnetic layer, and a second nonmagnetic layer provided between the second magnetic layer and the second opposing magnetic layer.

20. The sensor according to claim 19, wherein
a length of the first magnetic layer along a first magnetic layer direction crossing a first stacking direction is longer than a length of the first magnetic layer along a first magnetic layer cross direction crossing a plane including the first stacking direction and the first magnetic layer direction, the first stacking direction being from the first opposing magnetic layer toward the first magnetic layer, and
a length of the second magnetic layer along a second magnetic layer direction crossing a second stacking direction is longer than a length of the second magnetic layer along a second magnetic layer cross direction crossing a plane including the second stacking direction and the second magnetic layer direction, the second stacking direction being from the second opposing magnetic layer toward the second magnetic layer.

\* \* \* \* \*